(12) United States Patent
Holman et al.

(10) Patent No.: US 9,600,850 B2
(45) Date of Patent: Mar. 21, 2017

(54) CONTROLLED SUBSTANCE AUTHORIZATION SYSTEM AND METHOD FOR INGESTIBLE PRODUCT PREPARATION SYSTEM AND METHOD

(75) Inventors: Paul Holman, Seattle, WA (US); Royce A. Levien, Lexington, MA (US); Mark A. Malamud, Seattle, WA (US); Neal Stephenson, Seattle, WA (US); Christopher Charles Young, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 13/199,481

(22) Filed: Aug. 30, 2011

(65) Prior Publication Data
US 2013/0054256 A1    Feb. 28, 2013

Related U.S. Application Data

(63) Continuation of application No. 13/199,361, filed on Aug. 26, 2011.

(51) Int. Cl.
*G07F 17/00* (2006.01)
*G06Q 50/24* (2012.01)
*G06F 19/00* (2011.01)

(52) U.S. Cl.
CPC ........... *G06Q 50/24* (2013.01); *G06F 19/325* (2013.01)

(58) Field of Classification Search
CPC .......................................... G06Q 50/22–50/24
USPC ....................................................... 705/2, 3
See application file for complete search history.

(56) References Cited

U.S. PATENT DOCUMENTS

| | | | |
|---|---|---|---|
| 1,570,405 A | 1/1926 | Salerno |
| 3,702,583 A | 11/1972 | Rullman |
| 3,859,904 A | 1/1975 | Carriazo |
| 4,076,846 A | 2/1978 | Nakatsuka et al. |
| 4,135,077 A | 1/1979 | Wills |
| 4,293,296 A | 10/1981 | Caiello et al. |
| 4,452,132 A | 6/1984 | Miller et al. |
| 4,634,597 A | 1/1987 | Spiel et al. |

(Continued)

FOREIGN PATENT DOCUMENTS

| | | |
|---|---|---|
| NL | 2003661 C | 4/2011 |
| WO | WO 03/056493 A1 | 7/2003 |
| WO | WO 2006/095212 A1 | 9/2006 |

OTHER PUBLICATIONS

American Society of Hospital Pharmacists. ASHP Technical Assistance Bulletin on compounding nonsterile products in pharmacies. Am J Hosp Pharm. 1994, 51:1441-8.*

(Continued)

*Primary Examiner* — Jonathan K Ng

(57) ABSTRACT

A computationally implemented system and method that is designed to, but is not limited to: electronically using the electronically received directive information to electronically direct control of the at least partial preparation of the ingestible product designated to be ingested by the particular individual living being upon electronically verifying, thru electronic use of the directive information that the authority is authorized to issue the controlled substance instruction and that the controlled substance instruction has been issued by the authority. In addition to the foregoing, other method aspects are described in the claims, drawings, and text forming a part of the present disclosure.

55 Claims, 38 Drawing Sheets

(56) References Cited

U.S. PATENT DOCUMENTS

| | | |
|---|---|---|
| 4,666,204 A | 5/1987 | Reinholtz |
| 4,681,000 A | 7/1987 | Wolters |
| 4,723,614 A | 2/1988 | Lahti |
| 4,797,818 A | 1/1989 | Cotter |
| 4,974,747 A | 12/1990 | Ahlström |
| 5,121,677 A | 6/1992 | Le Claire et al. |
| 5,132,914 A | 7/1992 | Cahlander et al. |
| 5,176,922 A | 1/1993 | Balsano et al. |
| 5,197,376 A | 3/1993 | Bird et al. |
| 5,228,382 A | 7/1993 | Hayashi et al. |
| 5,261,150 A | 11/1993 | Grube et al. |
| 5,408,443 A | 4/1995 | Weinberger |
| 5,417,989 A | 5/1995 | Atwood et al. |
| 5,511,594 A * | 4/1996 | Brennan et al. ............... 141/98 |
| 5,522,309 A | 6/1996 | Mizobuchi et al. |
| 5,522,310 A | 6/1996 | Black, Sr. et al. |
| 5,540,943 A | 7/1996 | Naramura |
| 5,583,129 A * | 12/1996 | Spona et al. ................. 514/178 |
| 5,598,947 A | 2/1997 | Smith |
| 5,615,778 A | 4/1997 | Kaiser et al. |
| 5,697,043 A | 12/1997 | Baskaran et al. |
| 5,731,020 A | 3/1998 | Russo |
| 5,762,971 A | 6/1998 | Schirmer |
| 5,820,906 A | 10/1998 | Akesson et al. |
| 6,032,574 A | 3/2000 | Brayton et al. |
| 6,048,191 A | 4/2000 | Beltrami |
| 6,105,818 A | 8/2000 | Speranza |
| 6,112,182 A | 8/2000 | Akers et al. |
| 6,194,017 B1 | 2/2001 | Woodward et al. |
| 6,200,125 B1 | 3/2001 | Akutagawa |
| 6,202,923 B1 * | 3/2001 | Boyer et al. ................. 235/375 |
| 6,236,974 B1 | 5/2001 | Kolawa et al. |
| 6,245,556 B1 | 6/2001 | Sako et al. |
| 6,251,456 B1 | 6/2001 | Maul et al. |
| 6,268,004 B1 | 7/2001 | Hayashi |
| 6,280,784 B1 | 8/2001 | Yang et al. |
| 6,280,785 B1 | 8/2001 | Yang et al. |
| 6,280,786 B1 | 8/2001 | Williams et al. |
| 6,376,000 B1 | 4/2002 | Waters |
| 6,415,555 B1 | 7/2002 | Montague |
| 6,490,870 B1 | 12/2002 | Efremkine |
| 6,618,062 B1 | 9/2003 | Brown et al. |
| 6,622,064 B2 | 9/2003 | Bartholomew et al. |
| 6,637,432 B2 | 10/2003 | Wakefield et al. |
| 6,644,359 B1 | 11/2003 | Wertheim |
| 6,646,659 B1 | 11/2003 | Brown et al. |
| 6,658,990 B1 | 12/2003 | Henning et al. |
| 6,660,317 B1 | 12/2003 | Akutagawa |
| 6,660,982 B2 | 12/2003 | Thorneywork |
| 6,711,460 B1 * | 3/2004 | Reese ............................ 700/216 |
| 6,802,433 B2 | 10/2004 | Leykin et al. |
| 6,843,166 B1 | 1/2005 | Li |
| 6,859,215 B1 | 2/2005 | Brown et al. |
| 6,865,261 B1 | 3/2005 | Rao et al. |
| 6,998,087 B1 | 2/2006 | Hanson et al. |
| 7,006,893 B2 | 2/2006 | Hart et al. |
| 7,027,996 B2 | 4/2006 | Levinson |
| 7,054,909 B1 | 5/2006 | Ohkubo et al. |
| 7,080,597 B2 | 7/2006 | Ando |
| 7,098,794 B2 | 8/2006 | Lindsay et al. |
| 7,110,964 B2 | 9/2006 | Tengler et al. |
| 7,183,518 B2 | 2/2007 | Near et al. |
| 7,187,960 B2 | 3/2007 | Abreu |
| 7,188,082 B2 | 3/2007 | Keane et al. |
| 7,200,644 B1 | 4/2007 | Flanagan |
| 7,231,917 B2 | 6/2007 | Frederiksen |
| 7,243,789 B2 | 7/2007 | Discko, Jr. |
| 7,281,468 B2 | 10/2007 | Frem |
| 7,295,889 B2 | 11/2007 | Lähteenmäki |
| 7,299,982 B2 | 11/2007 | Kreiner et al. |
| 7,319,780 B2 | 1/2008 | Fedorovskaya et al. |
| 7,343,174 B2 | 3/2008 | Suryanarayana et al. |
| 7,364,068 B1 | 4/2008 | Strubbe et al. |
| 7,392,193 B2 | 6/2008 | Mault |
| 7,395,134 B2 | 7/2008 | Bartholomew et al. |
| 7,415,375 B2 | 8/2008 | Shakman et al. |
| 7,451,015 B2 | 11/2008 | Mazur et al. |
| 7,457,685 B2 | 11/2008 | D'Silva |
| 7,555,360 B1 | 6/2009 | Green et al. |
| 7,571,586 B1 | 8/2009 | Morales |
| 7,625,198 B2 | 12/2009 | Lipson et al. |
| 7,630,790 B2 | 12/2009 | Handfield et al. |
| 7,680,690 B1 | 3/2010 | Catalano |
| 7,698,566 B1 | 4/2010 | Stone |
| 7,747,345 B2 | 6/2010 | Ohmura et al. |
| 7,762,181 B2 | 7/2010 | Boland et al. |
| 7,783,379 B2 | 8/2010 | Beane et al. |
| 7,818,089 B2 | 10/2010 | Hanna et al. |
| 7,842,323 B1 | 11/2010 | White |
| 7,884,953 B1 | 2/2011 | Willcocks et al. |
| 7,961,916 B2 | 6/2011 | Wang et al. |
| 7,974,873 B2 | 7/2011 | Simmons et al. |
| 8,007,847 B2 | 8/2011 | Biderman et al. |
| 8,027,748 B2 | 9/2011 | Handfield et al. |
| 8,085,135 B2 | 12/2011 | Cohen Alloro et al. |
| 8,173,186 B2 | 5/2012 | Kuwabara et al. |
| 8,190,447 B2 | 5/2012 | Hungerford et al. |
| 8,204,757 B2 | 6/2012 | Carlson et al. |
| 8,249,946 B2 | 8/2012 | Froseth et al. |
| 8,306,655 B2 | 11/2012 | Newman |
| 8,370,176 B2 | 2/2013 | Vespasiani |
| 8,412,369 B2 | 4/2013 | Ames, II et al. |
| 8,504,440 B1 | 8/2013 | Kolawa et al. |
| 8,521,326 B1 | 8/2013 | Holtje |
| 8,583,511 B2 | 11/2013 | Hendrickson |
| 8,594,838 B2 | 11/2013 | Selker et al. |
| 8,594,935 B2 | 11/2013 | Cioffi et al. |
| 8,688,277 B2 | 4/2014 | Studor et al. |
| 8,744,618 B2 | 6/2014 | Peters et al. |
| 2001/0005830 A1 | 6/2001 | Kuroyanagi |
| 2001/0028308 A1 | 10/2001 | De La Huerga |
| 2001/0036495 A1 | 11/2001 | Ganan-Calvo |
| 2002/0029149 A1 | 3/2002 | Nishina |
| 2002/0042726 A1 | 4/2002 | Mayaud |
| 2002/0049652 A1 | 4/2002 | Moore et al. |
| 2002/0069097 A1 | 6/2002 | Conrath |
| 2002/0081356 A1 | 6/2002 | Bebiak et al. |
| 2002/0138201 A1 * | 9/2002 | Greensides ...................... 702/2 |
| 2002/0156682 A1 | 10/2002 | DiPietro |
| 2002/0192572 A1 | 12/2002 | Lau |
| 2003/0017248 A1 | 1/2003 | Gray |
| 2003/0050854 A1 | 3/2003 | Showghi et al. |
| 2003/0051606 A1 | 3/2003 | Cusenza et al. |
| 2003/0069745 A1 | 4/2003 | Zenko |
| 2003/0071806 A1 | 4/2003 | Annand |
| 2003/0079612 A1 | 5/2003 | Con |
| 2003/0099157 A1 | 5/2003 | Quine |
| 2003/0105555 A1 | 6/2003 | Lunak et al. |
| 2003/0121929 A1 | 7/2003 | Liff et al. |
| 2003/0125836 A1 | 7/2003 | Chirnomas |
| 2003/0125963 A1 | 7/2003 | Haken |
| 2003/0125986 A1 | 7/2003 | Collosi |
| 2003/0185948 A1 | 10/2003 | Garwood |
| 2003/0197005 A1 | 10/2003 | Huegerich et al. |
| 2003/0208113 A1 | 11/2003 | Mault et al. |
| 2003/0208409 A1 | 11/2003 | Mault |
| 2003/0219527 A1 | 11/2003 | Sasaki et al. |
| 2003/0236706 A1 | 12/2003 | Weiss |
| 2004/0025701 A1 | 2/2004 | Colston et al. |
| 2004/0045579 A1 | 3/2004 | Miki et al. |
| 2004/0049407 A1 | 3/2004 | Rosenberg |
| 2004/0054554 A1 | 3/2004 | Barts et al. |
| 2004/0073448 A1 | 4/2004 | Barts et al. |
| 2004/0073449 A1 | 4/2004 | Yang |
| 2004/0091843 A1 | 5/2004 | Albro et al. |
| 2004/0093265 A1 | 5/2004 | Ramchandani et al. |
| 2004/0093268 A1 | 5/2004 | Ramchandani et al. |
| 2004/0103033 A1 | 5/2004 | Reade et al. |
| 2004/0117205 A1 * | 6/2004 | Reardan et al. .................. 705/2 |
| 2004/0131659 A1 * | 7/2004 | Gibson et al. ................ 424/439 |
| 2004/0143503 A1 | 7/2004 | Suthar |
| 2004/0151820 A1 | 8/2004 | Harris |
| 2004/0158350 A1 | 8/2004 | Ostergaard et al. |
| 2004/0158499 A1 | 8/2004 | Dev et al. |

(56) References Cited

U.S. PATENT DOCUMENTS

| | | |
|---|---|---|
| 2004/0193495 A1 | 9/2004 | Kim |
| 2004/0214597 A1 | 10/2004 | Suryanarayana et al. |
| 2004/0226775 A1 | 11/2004 | Takatama et al. |
| 2004/0238555 A1 | 12/2004 | Parks |
| 2004/0246819 A1 | 12/2004 | Quine |
| 2004/0250842 A1 | 12/2004 | Adams et al. |
| 2004/0263319 A1 | 12/2004 | Huomo |
| 2005/0023710 A1 | 2/2005 | Brodkin et al. |
| 2005/0038719 A1 | 2/2005 | Young et al. |
| 2005/0048461 A1 | 3/2005 | Lahteenmaki |
| 2005/0059849 A1 | 3/2005 | Liu |
| 2005/0060063 A1 | 3/2005 | Reichelt et al. |
| 2005/0065640 A1 | 3/2005 | Mallett et al. |
| 2005/0079257 A1 | 4/2005 | Neto |
| 2005/0080520 A1 | 4/2005 | Kline et al. |
| 2005/0080650 A1 | 4/2005 | Noel |
| 2005/0098169 A1 | 5/2005 | Frederiksen |
| 2005/0113968 A1 | 5/2005 | Williams et al. |
| 2005/0114149 A1 | 5/2005 | Rodriguez et al. |
| 2005/0131738 A1 | 6/2005 | Morris |
| 2005/0157148 A1 | 7/2005 | Baker et al. |
| 2005/0160052 A1* | 7/2005 | Schneider et al. ............ 705/67 |
| 2005/0171663 A1 | 8/2005 | Mittelsteadt et al. |
| 2005/0193901 A1 | 9/2005 | Buehler |
| 2005/0209915 A1* | 9/2005 | Saluccio ..................... 705/14 |
| 2005/0226975 A1 | 10/2005 | Drouillard |
| 2005/0230472 A1 | 10/2005 | Chang |
| 2005/0233011 A1 | 10/2005 | Beavers |
| 2005/0241497 A1 | 11/2005 | Cantu |
| 2005/0251289 A1 | 11/2005 | Bonney et al. |
| 2005/0267811 A1 | 12/2005 | Almblad |
| 2005/0280544 A1 | 12/2005 | Mishelevich |
| 2006/0015289 A1 | 1/2006 | Shakman et al. |
| 2006/0053184 A1 | 3/2006 | Grana |
| 2006/0064037 A1 | 3/2006 | Shalon et al. |
| 2006/0081653 A1 | 4/2006 | Boland et al. |
| 2006/0108415 A1 | 5/2006 | Thomas et al. |
| 2006/0111976 A1 | 5/2006 | Pompushko |
| 2006/0147581 A1 | 7/2006 | Svendsen et al. |
| 2006/0161453 A1* | 7/2006 | Kost et al. ..................... 705/2 |
| 2006/0178943 A1 | 8/2006 | Rollinson et al. |
| 2006/0191885 A1 | 8/2006 | Near et al. |
| 2006/0224419 A1 | 10/2006 | Servizio et al. |
| 2006/0237523 A1 | 10/2006 | Carlson et al. |
| 2006/0259188 A1 | 11/2006 | Berg |
| 2006/0260601 A1 | 11/2006 | Schedeler et al. |
| 2006/0263501 A1 | 11/2006 | Oghafua et al. |
| 2006/0277066 A1 | 12/2006 | Hungerford et al. |
| 2006/0278093 A1 | 12/2006 | Biderman et al. |
| 2006/0286218 A1 | 12/2006 | Salzman |
| 2007/0027432 A1 | 2/2007 | Radford et al. |
| 2007/0037567 A1 | 2/2007 | Ungless et al. |
| 2007/0038727 A1 | 2/2007 | Bailey et al. |
| 2007/0048407 A1 | 3/2007 | Collins et al. |
| 2007/0055550 A1 | 3/2007 | Courtney et al. |
| 2007/0055694 A1 | 3/2007 | Ruge et al. |
| 2007/0057039 A1 | 3/2007 | Carlson et al. |
| 2007/0061170 A1* | 3/2007 | Lorsch ............................ 705/3 |
| 2007/0061209 A1 | 3/2007 | Jackson |
| 2007/0062156 A1 | 3/2007 | Kim |
| 2007/0083494 A1 | 4/2007 | Carlson et al. |
| 2007/0092614 A1 | 4/2007 | Waldock |
| 2007/0150371 A1 | 6/2007 | Gangji |
| 2007/0150375 A1 | 6/2007 | Yang |
| 2007/0151984 A1 | 7/2007 | Baker et al. |
| 2007/0168205 A1 | 7/2007 | Carlson et al. |
| 2007/0170195 A1 | 7/2007 | Segiet et al. |
| 2007/0185615 A1 | 8/2007 | Bossi et al. |
| 2007/0185785 A1 | 8/2007 | Carlson et al. |
| 2007/0191689 A1 | 8/2007 | Elitok |
| 2007/0192715 A1 | 8/2007 | Kataria et al. |
| 2007/0208454 A1 | 9/2007 | Forrester et al. |
| 2007/0231435 A1 | 10/2007 | Ream et al. |
| 2007/0260487 A1 | 11/2007 | Bartfeld et al. |
| 2007/0267441 A1 | 11/2007 | van Opstal et al. |
| 2007/0275690 A1 | 11/2007 | Hunter et al. |
| 2008/0059226 A1 | 3/2008 | Melker et al. |
| 2008/0077440 A1 | 3/2008 | Doron |
| 2008/0084450 A1 | 4/2008 | Silverbrook |
| 2008/0114678 A1 | 5/2008 | Bennett et al. |
| 2008/0124433 A1 | 5/2008 | Yelden et al. |
| 2008/0125897 A1* | 5/2008 | DiGianfilippo et al. ..... 700/110 |
| 2008/0126220 A1 | 5/2008 | Baril et al. |
| 2008/0126985 A1 | 5/2008 | Baril et al. |
| 2008/0141315 A1 | 6/2008 | Ogilvie |
| 2008/0162181 A1 | 7/2008 | Ben-Haim et al. |
| 2008/0173711 A1 | 7/2008 | Handfield et al. |
| 2008/0195247 A1 | 8/2008 | Mallett et al. |
| 2008/0224823 A1 | 9/2008 | Lawson et al. |
| 2008/0249859 A1 | 10/2008 | Angell et al. |
| 2008/0249865 A1 | 10/2008 | Angell et al. |
| 2008/0260918 A1 | 10/2008 | Lai et al. |
| 2008/0272138 A1 | 11/2008 | Ross et al. |
| 2008/0281915 A1 | 11/2008 | Elad et al. |
| 2008/0288287 A1* | 11/2008 | Stanners ........................... 705/2 |
| 2008/0314918 A1 | 12/2008 | Nuriely |
| 2009/0012433 A1 | 1/2009 | Fernstrom et al. |
| 2009/0029016 A1 | 1/2009 | Pfister et al. |
| 2009/0043176 A1 | 2/2009 | Nakajima et al. |
| 2009/0087819 A1 | 4/2009 | Adachi et al. |
| 2009/0099944 A1 | 4/2009 | Robinson et al. |
| 2009/0105875 A1 | 4/2009 | Wiles |
| 2009/0106313 A1 | 4/2009 | Boldyga |
| 2009/0106316 A1 | 4/2009 | Kubono et al. |
| 2009/0112683 A1 | 4/2009 | Hamilton, II et al. |
| 2009/0112754 A1 | 4/2009 | Seifert et al. |
| 2009/0112782 A1 | 4/2009 | Cross et al. |
| 2009/0130449 A1 | 5/2009 | El-Siblani |
| 2009/0132379 A1 | 5/2009 | Baril et al. |
| 2009/0142223 A1 | 6/2009 | Hyde et al. |
| 2009/0149717 A1 | 6/2009 | Brauer et al. |
| 2009/0161907 A1 | 6/2009 | Healey et al. |
| 2009/0164897 A1 | 6/2009 | Amer-Yahia et al. |
| 2009/0167553 A1 | 7/2009 | Hong et al. |
| 2009/0192898 A1 | 7/2009 | Baril |
| 2009/0198547 A1 | 8/2009 | Sudak |
| 2009/0199105 A1 | 8/2009 | Kamada et al. |
| 2009/0218363 A1 | 9/2009 | Terzini |
| 2009/0234712 A1 | 9/2009 | Kolawa et al. |
| 2009/0236333 A1 | 9/2009 | Ben-Shmuel et al. |
| 2009/0236334 A1 | 9/2009 | Ben-Shmuel et al. |
| 2009/0236335 A1 | 9/2009 | Ben-Shmuel et al. |
| 2009/0242620 A1 | 10/2009 | Sahuguet |
| 2009/0254531 A1 | 10/2009 | Walker et al. |
| 2009/0259559 A1 | 10/2009 | Carroll et al. |
| 2009/0259688 A1 | 10/2009 | Do et al. |
| 2009/0261175 A1 | 10/2009 | Kauppinen et al. |
| 2009/0267895 A1 | 10/2009 | Bunch |
| 2009/0294521 A1* | 12/2009 | de la Huerga ................ 235/375 |
| 2009/0295569 A1* | 12/2009 | Corwin et al. .......... 340/539.12 |
| 2009/0295575 A1 | 12/2009 | Kennedy |
| 2009/0297668 A1 | 12/2009 | Cantu |
| 2009/0299645 A1 | 12/2009 | Colby et al. |
| 2009/0317519 A1 | 12/2009 | Lavie et al. |
| 2009/0326516 A1 | 12/2009 | Bangera et al. |
| 2010/0017296 A1 | 1/2010 | Spignesi, Jr. et al. |
| 2010/0038416 A1 | 2/2010 | Canora |
| 2010/0038594 A1 | 2/2010 | Bohlig et al. |
| 2010/0042427 A1 | 2/2010 | Graham et al. |
| 2010/0043834 A1 | 2/2010 | Scheringer |
| 2010/0045705 A1 | 2/2010 | Vertegaal et al. |
| 2010/0047410 A1 | 2/2010 | Lichtenstein |
| 2010/0052900 A1 | 3/2010 | Covannon et al. |
| 2010/0055257 A1 | 3/2010 | Hervig |
| 2010/0062169 A1 | 3/2010 | Pierre |
| 2010/0063889 A1 | 3/2010 | Proctor, Jr. et al. |
| 2010/0087155 A1 | 4/2010 | Dubost |
| 2010/0097180 A1* | 4/2010 | Cardullo ...................... 340/5.83 |
| 2010/0100237 A1 | 4/2010 | Ratnakar |
| 2010/0106523 A1 | 4/2010 | Kalamas |
| 2010/0106607 A1 | 4/2010 | Riddiford et al. |
| 2010/0121156 A1 | 5/2010 | Yoo |
| 2010/0121722 A1 | 5/2010 | Vawter |
| 2010/0136666 A1 | 6/2010 | Kobayashi et al. |

(56) References Cited

U.S. PATENT DOCUMENTS

| | | | |
|---|---|---|---|
| 2010/0139992 A1 | 6/2010 | Delia et al. | |
| 2010/0145506 A1 | 6/2010 | Waugh et al. | |
| 2010/0160745 A1 | 6/2010 | Hills et al. | |
| 2010/0161345 A1 | 6/2010 | Cain et al. | |
| 2010/0161600 A1 | 6/2010 | Higgins et al. | |
| 2010/0167648 A1 | 7/2010 | Doutriaux | |
| 2010/0189842 A1 | 7/2010 | Toren | |
| 2010/0204676 A1 | 8/2010 | Cardullo | |
| 2010/0206765 A1 | 8/2010 | Fonte | |
| 2010/0235201 A1 | 9/2010 | McEvoy | |
| 2010/0250384 A1 | 9/2010 | Bhargava | |
| 2010/0256993 A1 | 10/2010 | Vespasiani | |
| 2010/0259719 A1* | 10/2010 | Sabeta | 351/161 |
| 2010/0268378 A1 | 10/2010 | Sharpley | |
| 2010/0268380 A1 | 10/2010 | Waugh et al. | |
| 2010/0275625 A1 | 11/2010 | Lowenstein | |
| 2010/0286632 A1 | 11/2010 | Dos Santos | |
| 2010/0291515 A1 | 11/2010 | Pinnisi et al. | |
| 2010/0292998 A1 | 11/2010 | Bodlaender et al. | |
| 2010/0299158 A1* | 11/2010 | Siegel | 705/3 |
| 2010/0303972 A1 | 12/2010 | Srivastava | |
| 2010/0305974 A1 | 12/2010 | Patch et al. | |
| 2010/0310737 A1 | 12/2010 | Someya et al. | |
| 2010/0312143 A1 | 12/2010 | Kim | |
| 2010/0312385 A1 | 12/2010 | Deuber | |
| 2010/0312601 A1 | 12/2010 | Lin | |
| 2010/0320189 A1 | 12/2010 | Buchheit | |
| 2010/0332140 A1 | 12/2010 | Joyce et al. | |
| 2010/0332250 A1* | 12/2010 | Simpson et al. | 705/2 |
| 2011/0000923 A1 | 1/2011 | Morales | |
| 2011/0004624 A1 | 1/2011 | Bansal et al. | |
| 2011/0009715 A1 | 1/2011 | O'Reilly et al. | |
| 2011/0022225 A1 | 1/2011 | Rothschild | |
| 2011/0027432 A1 | 2/2011 | Loeser | |
| 2011/0031236 A1 | 2/2011 | Ben-Shmuel et al. | |
| 2011/0040660 A1 | 2/2011 | Allison et al. | |
| 2011/0055044 A1 | 3/2011 | Wiedl | |
| 2011/0076349 A1 | 3/2011 | Yoshihara et al. | |
| 2011/0087076 A1 | 4/2011 | Brynelsen et al. | |
| 2011/0124996 A1 | 5/2011 | Reinke et al. | |
| 2011/0133005 A1 | 6/2011 | Chesack | |
| 2011/0160902 A1 | 6/2011 | Postins | |
| 2011/0166881 A1 | 7/2011 | Brazzo et al. | |
| 2011/0173062 A1 | 7/2011 | Chen et al. | |
| 2011/0186624 A1 | 8/2011 | Wagner et al. | |
| 2011/0208617 A1 | 8/2011 | Weiland | |
| 2011/0231212 A1 | 9/2011 | Hurley et al. | |
| 2011/0231266 A1 | 9/2011 | Baril | |
| 2011/0282712 A1 | 11/2011 | Amos et al. | |
| 2011/0289572 A1 | 11/2011 | Skeel et al. | |
| 2011/0300270 A1 | 12/2011 | Koppens | |
| 2011/0307316 A1 | 12/2011 | Peters et al. | |
| 2011/0313867 A9 | 12/2011 | Silver | |
| 2011/0318717 A1 | 12/2011 | Adamowicz | |
| 2011/0320037 A1 | 12/2011 | Frugone | |
| 2012/0004770 A1* | 1/2012 | Ooyen et al. | 700/235 |
| 2012/0016745 A1 | 1/2012 | Hendrickson | |
| 2012/0016754 A1 | 1/2012 | Jackson | |
| 2012/0041770 A1 | 2/2012 | Philippe | |
| 2012/0041778 A1 | 2/2012 | Kraft | |
| 2012/0088212 A1 | 4/2012 | Knaan | |
| 2012/0089249 A1 | 4/2012 | Rosenblum | |
| 2012/0101914 A1 | 4/2012 | Kumar et al. | |
| 2012/0131619 A1 | 5/2012 | Ogilvie | |
| 2012/0136731 A1 | 5/2012 | Kidron et al. | |
| 2012/0137325 A1 | 5/2012 | Ogilvie | |
| 2012/0152125 A1 | 6/2012 | Yoakim et al. | |
| 2012/0156337 A1 | 6/2012 | Studor et al. | |
| 2012/0168985 A1 | 7/2012 | Kläber | |
| 2012/0173271 A1 | 7/2012 | Omidi | |
| 2012/0179665 A1 | 7/2012 | Baarman et al. | |
| 2012/0196011 A1 | 8/2012 | Felix | |
| 2012/0214140 A1 | 8/2012 | Brynelsen et al. | |
| 2012/0233002 A1 | 9/2012 | Abujbara | |
| 2012/0246004 A1 | 9/2012 | Book et al. | |
| 2012/0251688 A1 | 10/2012 | Zimmerman et al. | |
| 2012/0251689 A1 | 10/2012 | Batchelder | |
| 2012/0258216 A1 | 10/2012 | Wessels | |
| 2012/0262039 A1 | 10/2012 | Daugbjerg et al. | |
| 2012/0268259 A1 | 10/2012 | Igel et al. | |
| 2012/0284126 A1 | 11/2012 | Giraud et al. | |
| 2012/0290412 A1 | 11/2012 | Marovets | |
| 2012/0310760 A1 | 12/2012 | Phillips et al. | |
| 2012/0323208 A1 | 12/2012 | Bochenko et al. | |
| 2012/0323707 A1 | 12/2012 | Urban | |
| 2013/0006415 A1 | 1/2013 | Paydar et al. | |
| 2013/0011529 A1 | 1/2013 | Belzowski et al. | |
| 2013/0018356 A1 | 1/2013 | Prince et al. | |
| 2013/0034633 A1 | 2/2013 | von Hasseln | |
| 2013/0089642 A1 | 4/2013 | Lipson et al. | |
| 2013/0151268 A1 | 6/2013 | Fletcher | |
| 2013/0158705 A1 | 6/2013 | Levy et al. | |
| 2013/0171304 A1 | 7/2013 | Huntley | |
| 2013/0189405 A1 | 7/2013 | Filliol et al. | |
| 2013/0196035 A1 | 8/2013 | Passet et al. | |
| 2013/0238118 A1 | 9/2013 | Haas | |
| 2013/0273217 A1 | 10/2013 | Minvielle | |
| 2013/0304529 A1 | 11/2013 | Phalake et al. | |
| 2014/0013962 A1 | 1/2014 | Lipton et al. | |
| 2014/0050811 A1 | 2/2014 | Lipton et al. | |
| 2014/0304055 A1* | 10/2014 | Faith | 705/14.26 |

OTHER PUBLICATIONS

"Scientests create 'inhalable' food?"; bearing a date of Aug. 29, 2012; snapshot taken Apr. 12, 2009; available at htlp://web.archive.org/web/20090412131937/ http://chowhound.chow.com/topics/611174.

"Transdermal Nutrient Delivery System"; U.S. Army Soldier and Biological Chemical Command; snapshot taken Jul. 21, 2004; available at http://web.archive.org/web/20040721134210 http://archives.tproc.org/www.sbccom.army.mil.products/food/tdns.pdf.

U.S. Appl. No. 13/435,591, Holman et al.
U.S. Appl. No. 13/435,550, Holman et al.
U.S. Appl. No. 13/432,525, Holman et al.
U.S. Appl. No. 13/432,507, Holman et al.
U.S. Appl. No. 13/385,690, Holman et al.
U.S. Appl. No. 13/385,687, Holman et al.
U.S. Appl. No. 13/385,129, Holman et al.
U.S. Appl. No. 13/385,128, Holman et al.
U.S. Appl. No. 13/373,847, Holman et al.
U.S. Appl. No. 13/373,846, Holman et al.
U.S. Appl. No. 13/373,675, Holman et al.
U.S. Appl. No. 13/373,674, Holman et al.
U.S. Appl. No. 13/317,979, Holman et al.
U.S. Appl. No. 13/317,978, Holman et al.
U.S. Appl. No. 13/317,546, Holman et al.
U.S. Appl. No. 13/317,545, Holman et al.
U.S. Appl. No. 13/200,907, Holman et al.
U.S. Appl. No. 13/200,906, Holman et al.
U.S. Appl. No. 13/200,830, Holman et al.
U.S. Appl. No. 13/200,829, Holman et al.
U.S. Appl. No. 13/200,113, Holman et al.
U.S. Appl. No. 13/200,106, Holman et al.
U.S. Appl. No. 13/199,545, Holman et al.
U.S. Appl. No. 13/199,544, Holman et al.
U.S. Appl. No. 13/199,361, Holman et al.

"3D food printing"; PharmacyEscrow.com; printed on Apr. 4, 2012; 2 pages.

Blain, Loz; "Cornucopia: Digital Gastronomy—could 3D printing be the next revolution in cooking?"; Gizmag; Jan. 14, 2010; 4 pages.

Broomfield, Mark; "The Future of Food Printing"; Fab@Home; Aug. 20, 2009; 1 page.

Coelho, Marcelo; "Cornucopia"; printed on Apr. 4, 2012; 1 page; located at fluid.media.mut.edu.

Cohen et al.; "Hydrocolloid Printing: A Novel Platform for Customized Food Production"; Twentieth Annual International Solid Freeform Fabrication Symposium, Austin, Texas; bearing a date of 2009; cover page and pp. 807-818.

(56) References Cited

OTHER PUBLICATIONS

Fawkes, Piers; "3D Food Printing", PSFK; Jan. 17, 2008; 8 pages.
Flatley, Joseph L.; "Ikea's kitchen of the future: 3D food printing, mood lighting, virtual Gordon Ramsay"; Engadget; printed on Apr. 4, 2012; 4 pages; AOL Inc.
McKendrick, Joe; "3D food 'printing': coming to a kitchen near you"; Smartplanet; Dec. 27, 2010; 6 pages; located at www.smartplanet.com/business/blog/business-brains.
Periard et al.; "Printing Food"; Cornell University; printed on Apr. 6, 2012; 11 pages; located at www.creativemachines.cornell.edu/papers/SFF07_Periard2.pdf*.
"Printed Meats!"; Fabbaloo; Aug. 23, 2010; 5 pages; Fabbaloo.
"Prototypes and Concept Designs for a Digital Gastronomy"; Cornucopia; printed on Apr. 4, 2012; 5 pages.
Sandhana, Lakshmi; "The printed future of Christmas dinner"; BBC News Technology; Dec. 24, 2010; 4 pages; MMXI.
Seth, Radhika; "Printing My Food by the Molecule"; Yanko Design; Mar. 2, 2010; 7 pages.
Seth, Radhika; "Surreal Food is Real and Printed"; Yanko Design; Aug. 26, 2009; 6 pages.
"The CandyFab 6000"; Evil Mad Scientist Laboratories; bearing a date of 2011; 7 pages; Evil Mad Scientist Laboratories.
"Welcome to the CandyFabProject"; CandyFab.org; Jan. 22, 2011; 3 pages; The CandyFab Project.
McDonald's; sample restaurant menu (as provided by examiner); Feb. 10, 2014; 1 page; located at: http://www.burgerbusiness.com/wp-content/uploads/McD_Calor . . . .
"Airline Tickets and Airline Reservations from American Airlines"; AA.com; 1 page; retrieved from the internet wayback machine on Oct. 27, 2011 (as cited by examiner); located at http://web.archieve.org/web.20101027131457/http://www.aa.com.
Williams, N.T.; "Medication administration through enteral feeding tubes"; Am J Health Syst Pharm.; bearing a date of Dec. 15, 2008; 2 pages (abstract only); vol. 65, No. 24; located at http://www.ncbi.nlm.nih.gov/pubmed/19052281.
Indiana State Excise Police; "Alcohol Laws"; snapshot taken Oct. 22, 2010 (as cited by Examiner); pp. 1-2; located at http://web.archive.org/web/20101122202431/http://www.in.gov/atc/isep/2384.htm.
Valuevapor.com; "Starter Kits"; printed on Sep. 22, 2014; pp. 1-2; located at http://web.archive.org/web/20100610083606/http://www.valuevapor.com/VV/store/index.php?main_page=index&cPath=10.
"Easy Delft Blue Eggs"; The Sweet Adventures of Sugarbelle Blog; Mar. 25, 2012; pp. 1-7; located at: www.sweetsugarbelle.com/2012/03/simple-delft-blue-easter-egg-cookies (as provided by examiner).
Fiore et al; "Effects of Imagery Copy and Product Samples on Responses Toward the Product"; Journal of Interactive Marketing; bearing a date of Spring 2001; pp. 36-46; vol. 15, No. 2.
McDonagh-Philp, Deana; "Using Focus Groups to Support New Product Development"; Institution of Engineering Designers Journal; Sep. 2000; pp. 1-6.
Shimmura et al.; "Analysis of Eating Behavior in Restaurants Based on Leftover Food"; 2010; pp. 956-960; IEEE.
"Toddlers at the Table: Avoiding Power Struggles," located at https://web.archive.org/web/20101012173406/http://kidshealth.org/parent/nutrition_center/staying_fit/toddler_meals.html; KidsHealth; 2010; pp. 1-2; The Nemours Foundation.
Connors et al., "Using a Visual Plate Waste Study to Monitor Menu Performance"; Journal of the American Dietetic Association; 2004, created on Oct. 18, 2016; pp. 94-96; vol. 104; American Dietetic Association.

* cited by examiner

Fig. 6

10 ingestible product preparation system

- s100 control and information processing subsystem
- s200 information storage subsystem
- s300 information user interface subsystem
- s400 sensing subsystem
- s500 electronic communication subsystem
- s600 power subsystem
- s700 material processing subsystem

Fig. 7 s100 control and information processing subsystem

- s102 microprocessor component
- s104 central processing unit (CPU) component
- s106 digital signal processor (DSP) component
- s108 application specific integrated circuit (ASIC) component
- s110 field programmable gate array (FPGA) component
- s112 multiprocessor component
- s114 optical processing component
- s116 logic component

*Fig. 8* s200 information storage subsystem

| s202 random access memory (RAM) component | s204 dynamic random access memory (DRAM) component | s206 other volatile memory component | s208 persistent memory component | s210 read only memory (ROM) component |
| s212 electrically erasable programmable read only memory | s214 compact disk (CD) component | s216 digital versatile disk (DVD) component | s218 flash memory component | s220 other nonvolatile memory component |
| s222 hard drive component | s224 disk farm component | s226 disk cluster component | s228 remote backup component | s230 server component |
| s232 digital tape component | s234 optical storage component | s236 optical storage component | s238 computer readable signal bearing medium | s240 Blu Ray disk component |

Fig. 9 s300 information user interface subsystem

| s302 graphical user interface (GUI) component | s304 visual display component | s306 keyboard component | s308 keypad component | s310 trackball component |
| --- | --- | --- | --- | --- |
| s312 joystick component | s314 touch screen component | s316 mouse component | s318 switch component | s320 dial component |
| s322 button component | s324 gauge component | s326 light emitting component | s328 audio in/out component | s330 vibration emitting component |
| s332 portable information storage reader component | s334 projection component | s336 camera component | s338 scanner component | |

Fig. 10 s400 sensing subsystem

- s402 electromagnetic sensing component
- s404 antenna component
- s406 photodetecting component
- s408 micro-electro-mechanical system (MEMS) detecting component
- s410 weight sensing component
- s412 temperature sensing component
- s414 radio frequency identification (RFID) sensing
- s416 chemical sensing component
- s418 optical sensing component
- s420 sound sensing component
- s422 solid sensing component
- s424 liquid sensing component
- s426 solid sensing component

Fig. 13

| s700 material processing subsystem | | | |
|---|---|---|---|
| s702 heating component | s706 microwave component | s708 laser component | s710 light emitting diode (LED) component |
| s712 peltier cooling component | s716 mixer component | s718 acoustic energy component | s720 stirring component |
| s722 shaker component | s726 pump component | s728 sorting component | s730 infrared component |
| s732 cutting component | s734 material storage component | | |

(s704 cooling component; s714 blending component; s724 energy emitting component)

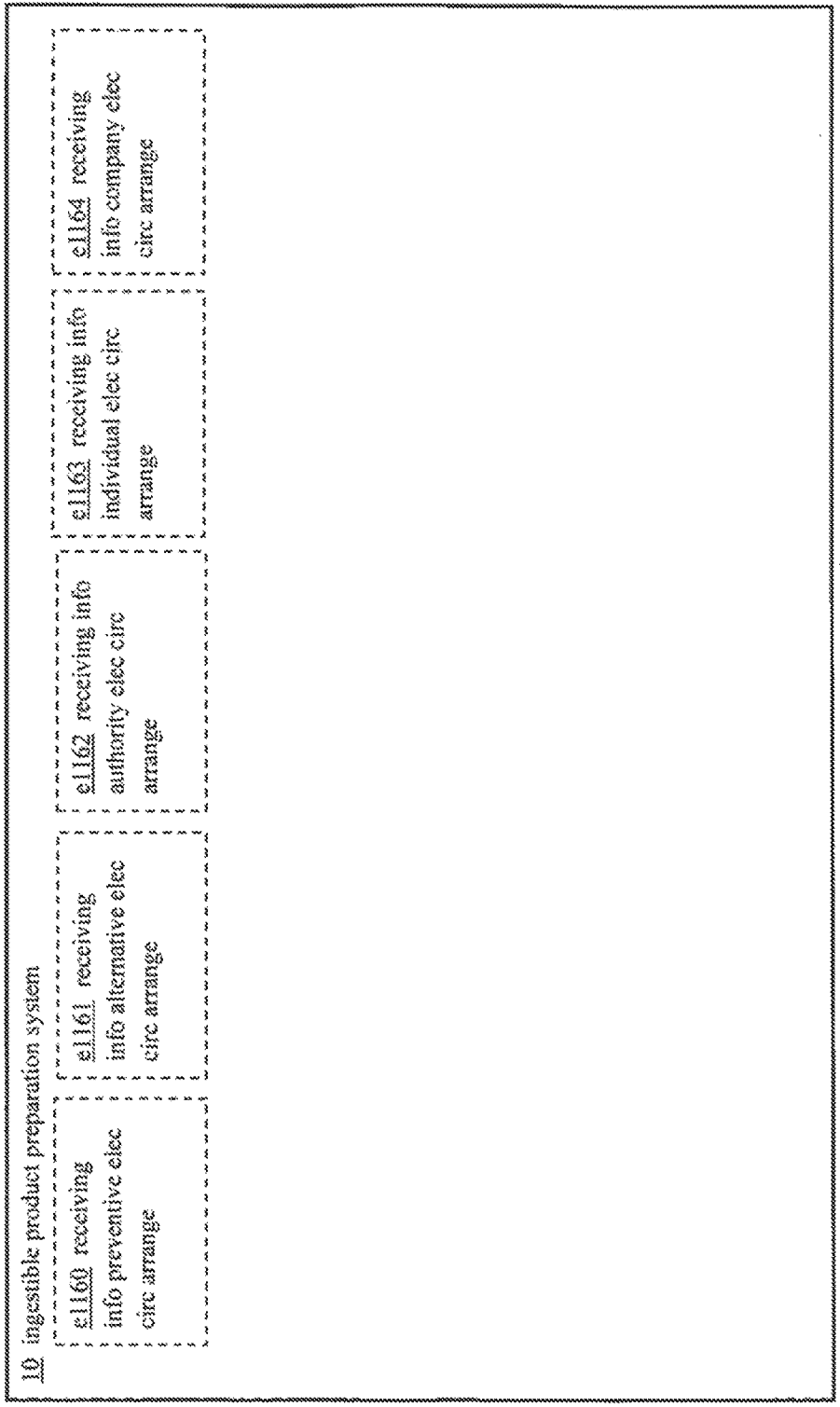

*Fig. 18*

| 10 ingestible product preparation system | | | |
|---|---|---|---|
| e12 controlling prep upon verify elec circ arrange | e1201 verifying thru comparison elec circ arrange | e1202 verifying thru encryption elec circ arrange | e1203 control prep thermal elec circ arrange | e1204 control prep heating elec circ arrange |
| e1205 control prep cooling elec circ arrange | e1206 control prep portion size elec circ arrange | e1207 control prep mixing elec circ arrange | e1208 control prep radiation elec circ arrange | e1209 control prep sound elec circ arrange |
| e1210 control prep infrared elec circ arrange | e1211 control prep microwave elec circ arrange | e1212 control prep container elec circ arrange | e1213 control prep syringe elec circ arrange | e1214 control prep mix before thermal elec circ arrange |
| e1215 control prep re mix after thermal elec circ arrange | e1216 control prep heating cooling elec circ arrange | e1217 control prep time control elec circ arrange | e1218 control prep ingredient exclusion elec circ arrange | e1219 control prep ingredient inclusion elec circ arrange |

Fig. 23

| n100 non-transitory signal bearing medium | | | |
|---|---|---|---|
| i112 controlling prep upon verify instructions | i1201 verifying thru comparison instructions | i1202 verifying thru encryption instructions | i1203 control prep thermal instructions | i1204 control prep heating instructions |
| i1205 control prep cooling instructions | i1206 control prep portion size instructions | i1207 control prep mixing instructions | i1208 control prep radiation instructions | i1209 control prep sound instructions |
| i1210 control prep infrared instructions | i1211 control prep microwave instructions | i1212 control prep container instructions | i1213 control prep syringe instructions | i1214 control prep mix before thermal instructions |
| i1215 control prep re mix after thermal instructions | i1216 control prep heating cooling instructions | i1217 control prep time control instructions | i1218 control prep ingredient exclusion instructions | i1219 control prep ingredient inclusion instructions |

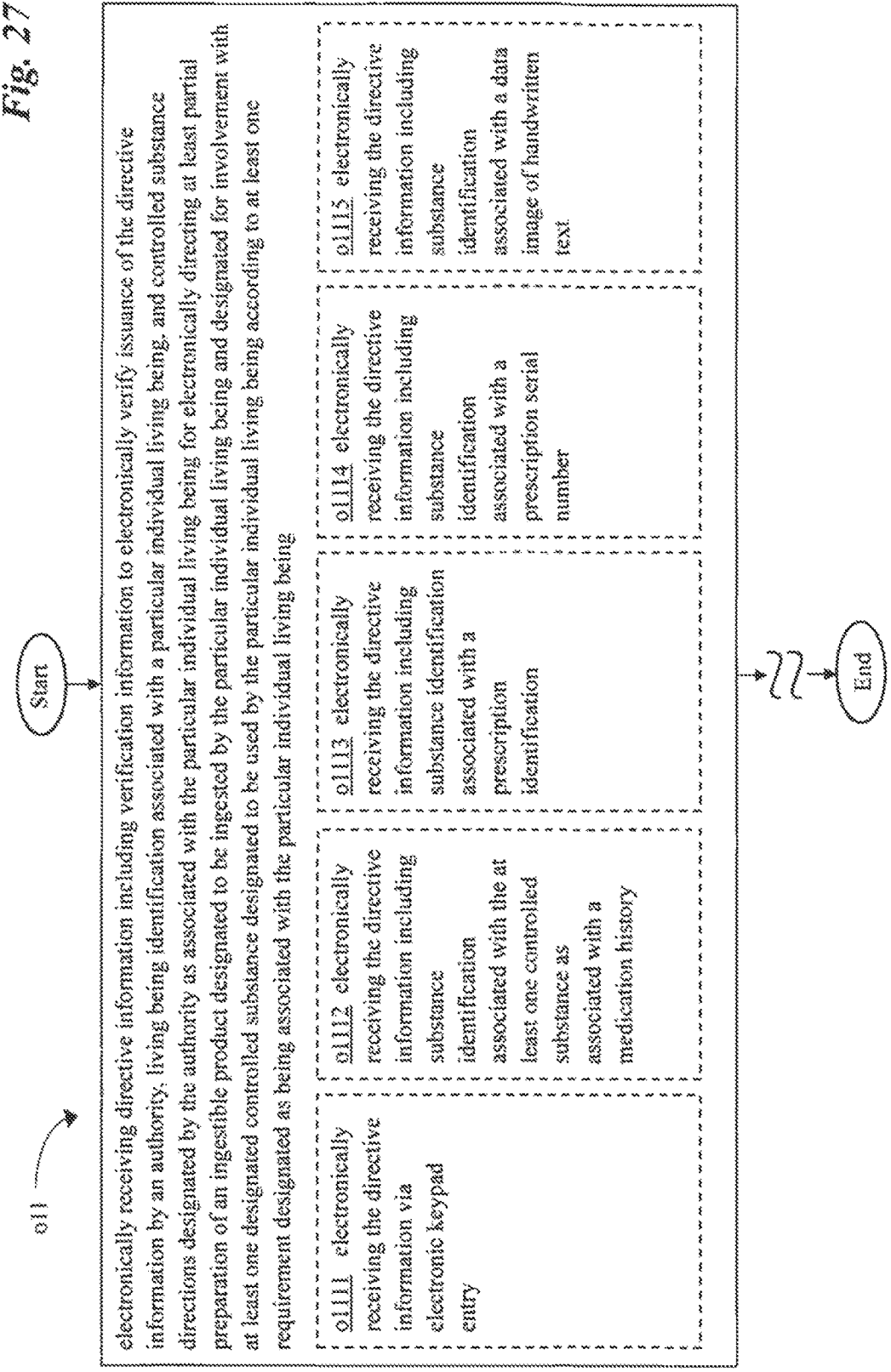

Fig. 28 o11 — electronically receiving directive information including verification information to electronically verify issuance of the directive information by an authority, living being identification associated with a particular individual living being, and controlled substance directions designated by the authority as associated with the particular individual living being for electronically directing at least partial preparation of an ingestible product designated to be ingested by the particular individual living being and designated for involvement with at least one designated controlled substance designated to be used by the particular individual living being according to at least one requirement designated as being associated with the particular individual living being o1116 electronically receiving the directive information including substance identification associated with a computer text file o1117 electronically receiving the directive information including substance identification associated with a computer audio file o1118 electronically receiving the directive information including substance identification associated with a computer video file o1119 electronically receiving the directive information including substance identification associated with an RFID tag o1120 electronically receiving the directive information including substance identification associated with a bar code

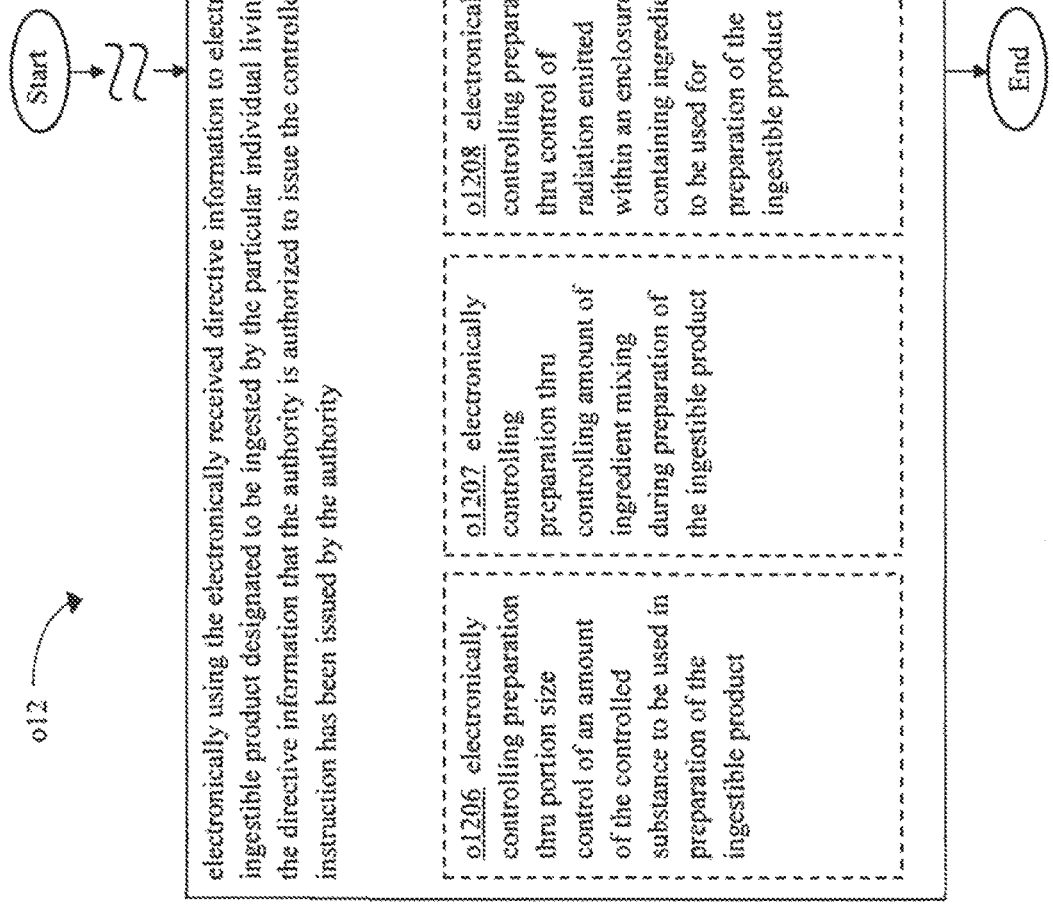

Fig. 40 o12 — electronically using the electronically received directive information to electronically direct control of the at least partial preparation of the ingestible product designated to be ingested by the particular individual living being upon electronically verifying, thru electronic use of the directive information that the authority is authorized to issue the controlled substance instruction and that the controlled substance instruction has been issued by the authority o1211 electronically controlling preparation thru control of microwave radiation emitted within an enclosure containing ingredients to be used for preparation of the ingestible product o1212 electronically controlling preparation thru control of an outlet of an ingredient container holding an ingredient used for preparation of the ingestible product o1213 electronically controlling preparation thru control of an outlet of an ingredient syringe holding an ingredient used for preparation of the ingestible product o1214 electronically controlling preparation thru control of mixing of at least some of the ingredients used to prepare the ingestible product before thermal treatment of the ingredients o1215 electronically controlling preparation thru control of blending of at least some of the ingredients used to prepare the ingestible product after thermal treatment of the ingredients

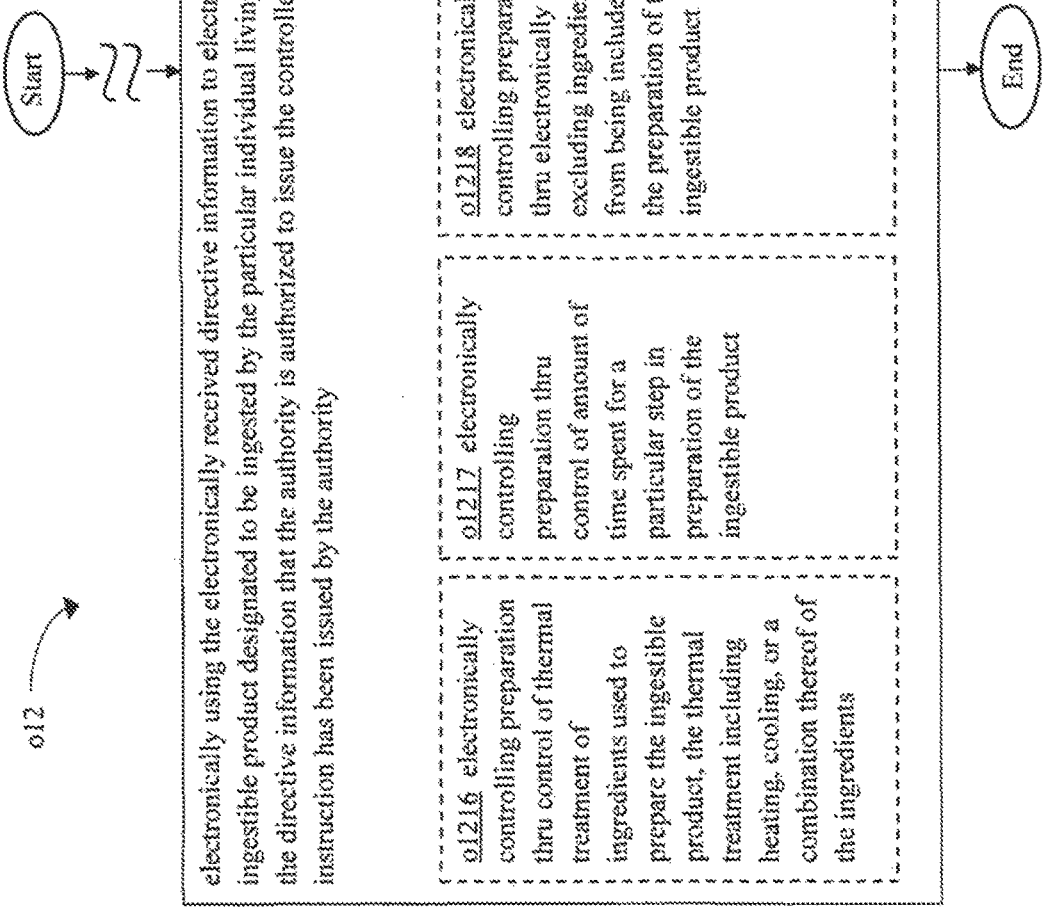

US 9,600,850 B2

CONTROLLED SUBSTANCE AUTHORIZATION SYSTEM AND METHOD FOR INGESTIBLE PRODUCT PREPARATION SYSTEM AND METHOD

RELATED APPLICATIONS

For purposes of the USPTO extra-statutory requirements, the present application constitutes a continuation of U.S. patent application Ser. No. 13/199,361, entitled REPORTING SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 31 Aug. 2011, which is currently co-pending or is an application of which a currently co-pending application is entitled to the benefit of the filing date.

SUMMARY

A method includes, but is not limited to electronically receiving directive information including verification information to electronically verify issuance of the directive information by an authority, living being identification associated with a particular individual living being, and controlled substance directions designated by the authority as associated with the particular individual living being for electronically directing at least partial preparation of an ingestible product designated to be ingested by the particular individual living being and designated for involvement with at least one designated controlled substance designated to be used by the particular individual living being according to at least one requirement designated as being associated with the particular individual living being; and electronically using the electronically received directive information to electronically direct control of the at least partial preparation of the ingestible product designated to be ingested by the particular individual living being upon electronically verifying, thru electronic use of the directive information that the authority is authorized to issue the controlled substance instruction and that the controlled substance instruction has been issued by the authority.

In one or more various aspects, related machines, compositions of matter, or manufactures of systems may include, but are not limited to, virtually any combination of hardware, software, and/or firmware (the virtually any combination being limited to patentable subject matter under 35 U.S.C. 101) configured to effect the herein-referenced method aspects depending upon the design choices of the system designer.

A system includes, but is not limited to: means for electronically receiving directive information including verification information to electronically verify issuance of the directive information by an authority, living being identification associated with a particular individual living being, and controlled substance directions designated by the authority as associated with the particular individual living being for electronically directing at least partial preparation of an ingestible product designated to be ingested by the particular individual living being and designated for involvement with at least one designated controlled substance designated to be used by the particular individual living being according to at least one requirement designated as being associated with the particular individual living being; and means for electronically using the electronically received directive information to electronically direct control of the at least partial preparation of the ingestible product designated to be ingested by the particular individual living being upon electronically verifying, thru electronic use of the directive information that the authority is authorized to issue the controlled substance instruction and that the controlled substance instruction has been issued by the authority. In addition to the foregoing, other system aspects are described in the claims, drawings, and text forming a part of the present disclosure.

A system includes, but is not limited to an electrical circuitry arrangement for electronically receiving directive information including verification information to electronically verify issuance of the directive information by an authority, living being identification associated with a particular individual living being, and controlled substance directions designated by the authority as associated with the particular individual living being for electronically directing at least partial preparation of an ingestible product designated to be ingested by the particular individual living being and designated for involvement with at least one designated controlled substance designated to be used by the particular individual living being according to at least one requirement designated as being associated with the particular individual living being; and an electrical circuitry arrangement for electronically using the electronically received directive information to electronically direct control of the at least partial preparation of the ingestible product designated to be ingested by the particular individual living being upon electronically verifying, thru electronic use of the directive information that the authority is authorized to issue the controlled substance instruction and that the controlled substance instruction has been issued by the authority. In addition to the foregoing, other system aspects are described in the claims, drawings, and text forming a part of the present disclosure.

An article of manufacture including a non-transitory signal-bearing storage medium bearing one or more instructions for electronically receiving directive information including verification information to electronically verify issuance of the directive information by an authority, living being identification associated with a particular individual living being, and controlled substance directions designated by the authority as associated with the particular individual living being for electronically directing at least partial preparation of an ingestible product designated to be ingested by the particular individual living being and designated for involvement with at least one designated controlled substance designated to be used by the particular individual living being according to at least one requirement designated as being associated with the particular individual living being; and one or more instructions for electronically using the electronically received directive information to electronically direct control of the at least partial preparation of the ingestible product designated to be ingested by the particular individual living being upon electronically verifying, thru electronic use of the directive information that the authority is authorized to issue the controlled substance instruction and that the controlled substance instruction has been issued by the authority. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 6 is a block diagram depicting an exemplary implementation of the ingestible product preparation system 10 including exemplary subsystems of FIG. 1.

FIG. 7 is a block diagram depicting a control and information processing subsystem s100 of an exemplary implementation of the ingestible product preparation system 10 of FIG. 1.

FIG. 8 is a block diagram depicting an information storage subsystem s200 of an exemplary implementation of the ingestible product preparation system 10 of FIG. 1.

FIG. 9 is a block diagram depicting an information user interface subsystem s300 of an exemplary implementation of the ingestible product preparation system 10 of FIG. 1.

FIG. 10 is a block diagram depicting a sensing subsystem s400 of an exemplary implementation of the ingestible product preparation system 10 of FIG. 1.

FIG. 13 is a block diagram depicting a material processing subsystem s700 of an exemplary implementation of the ingestible product preparation system 10 of FIG. 1.

FIG. 17 is a block diagram depicting one or more exemplary electrical circuitry arrangements of the ingestible product preparation system 10 of FIG. 1.

FIG. 18 is a block diagram depicting one or more exemplary electrical circuitry arrangements of the ingestible product preparation system 10 of FIG. 1.

FIG. 23 is a block diagram depicting one or more exemplary instructions of the information storage subsystem s200 of the ingestible product preparation system 10 of FIG. 1.

FIG. 27 is a high-level flowchart including exemplary implementations of operation O11 of FIG. 24.

FIG. 28 is a high-level flowchart including exemplary implementations of operation O11 of FIG. 24.

FIG. 39 is a high-level flowchart including exemplary implementations of operation O12 of FIG. 24.

FIG. 40 is a high-level flowchart including exemplary implementations of operation O12 of FIG. 24.

FIG. 41 is a high-level flowchart including exemplary implementations of operation O12 of FIG. 24.

DETAILED DESCRIPTION

Figure 1:
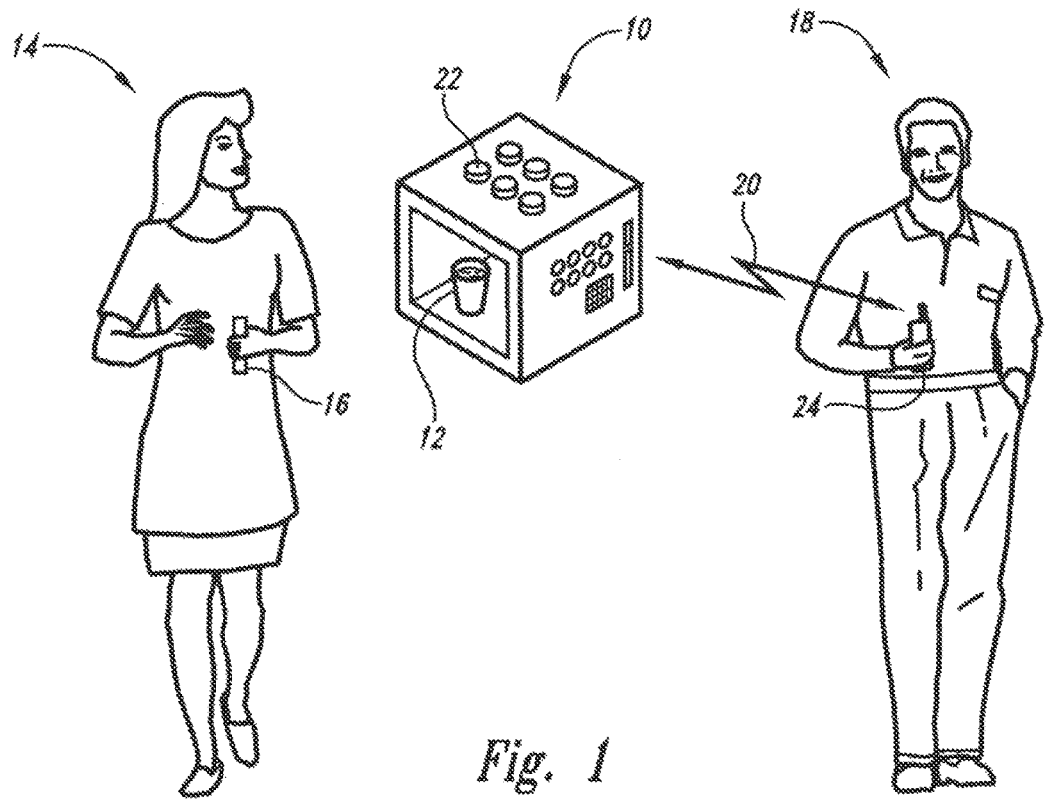
FIG. 1 is a schematic diagram depicting a first exemplary implementation of an ingestible product preparation system 10.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Generally, automated and semi-automated machines to make, manufacture, fabricate, or otherwise prepare ingestible products to be ingested by living beings such as humans, animals, plants, etc are known to a degree with interest existing for future development as well. Automated and semi-automated preparation of the ingestible products can incorporate all known forms of preparation of food and other ingestible products including but not limited to all known forms of energy addition to one or more ingredients of the ingestible products (such as through various forms of thermal heating or adding microwave, infrared, or ultrasonic energy), extracting energy from one or more ingredients of the ingestible products (such as through thermodynamic-cycle based cooling or peltier cooling), deposition methods (including deposition by layering or at the pixel level), and combinational methods (such as blending, mixing, ingredient injection, kneading, stirring, ultrasonic agitation, other agitational methods, etc.), etc.

Although ingestible products made, fabricated, or otherwise prepared by semi-automated and automated machines are presently limited in scope to a degree, it is envisioned that with future development, this will change. Ingestible products can take many forms including, but not limited to, solids, semi-solids, liquids, gases, dispersions (such as true solutions, colloid dispersions, emulsions, foams, and gels) and vast combinations thereof. Ingestion by the living beings can occur through many pathways including, but not limited to, oral ingestion, transdermal ingestion, peg-tube ingestion, anal ingestion, injectable ingestion, tear-duct ingestion, and respiratory ingestion.

Figure 2:
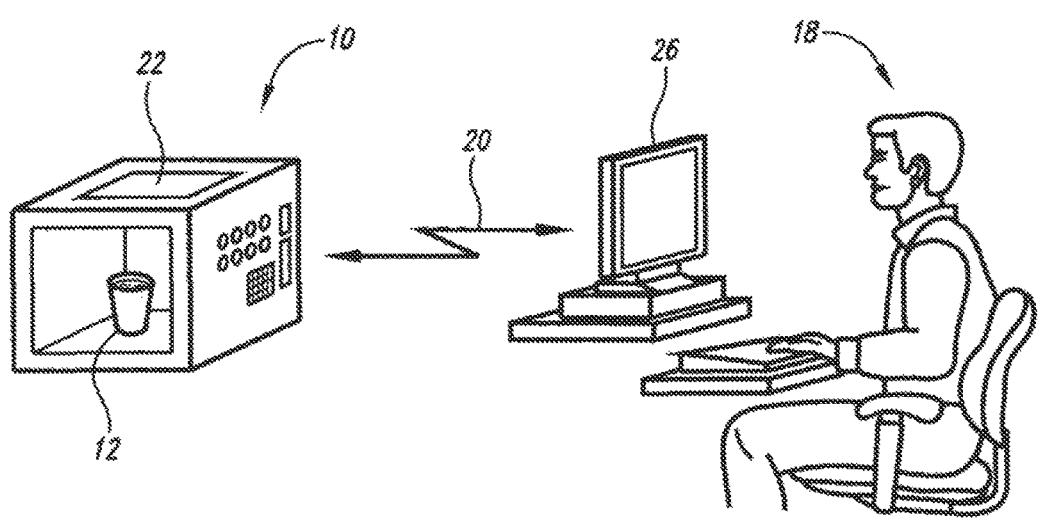
FIG. 2 is a schematic diagram depicting a second exemplary implementation of the ingestible product preparation system 10 of FIG. 1.

As depicted in FIG. 1, an exemplary implementation of an ingestible product preparation system 10 is shown to prepare ingestible products such as a liquid drink 12 as shown to be consumed by a particular individual living being, such as a human being 14 shown. Methods, systems, and articles of manufacture in accordance with various implementations of the ingestible product preparation system 10 are disclosed herein and are further discussed below. Another ingestible product is shown as a food bar 16 being held by the living being to be consumed thereby. An authority, such as a physician 18 shown, can send directive information 20 to the ingestible product preparation system 10 via a mobile device 24, such as a cell phone or other such communication device, such as a computer workstation 26 depicted in FIG. 2. In other implementations authorities can include but are not limited to pharmacists, nutritionists, health care centers, hospitals, fitness centers, other health care providers, etc. Generally, the authority is authorized in some fashion to be involved with the authorship and/or distribution control of the directive information 20. The directive information 20 includes verification information to allow verification for the ingestible product preparation system 10 that issuance of the directive information, such as involving authorship and/or distribution control of the directive information involved the authority. The directive information 20 also includes living being identification associated with a particular individual living being to be the recipient of one or more ingestible products to be prepared by the ingestible product preparation system 10 according to at least in part the directive information. The directive information 20 further includes controlled substance directions designated by the authority as associated with the particular individual living being. The controlled substance directions allow the ingestible product preparation system 10 to electronically direct at least partial preparation of one or more ingestible products designated to be ingested by the particular individual living being.

The ingestible product is also designated through the controlled substance information for involvement with at least one designated controlled substance, such as shown in containers 22, designated to be used by the particular individual living being according to at least one requirement designated as being associated with the particular individual living being. Involvement of the controlled substance with the ingestible product can include, but is not limited to, being incorporated into the ingestible product as one or more ingredients or otherwise one or more components of the ingestible product. Other cases of controlled substance involvement with the ingestible product include using the ingestible product as a carrier of the controlled substance or providing the ingestible product to be consumed alongside, concurrently, or at a designated time other than the time that ingestion of the controlled substance is designated to occur.

Figure 5:
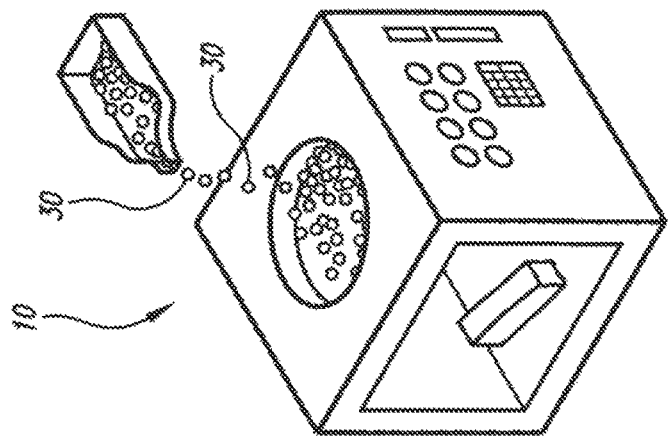
FIG. 5 is a schematic diagram depicting a third exemplary implementation of dispensing controlled substances for the ingestible product preparation system 10 of FIG. 1.
Figure 4:
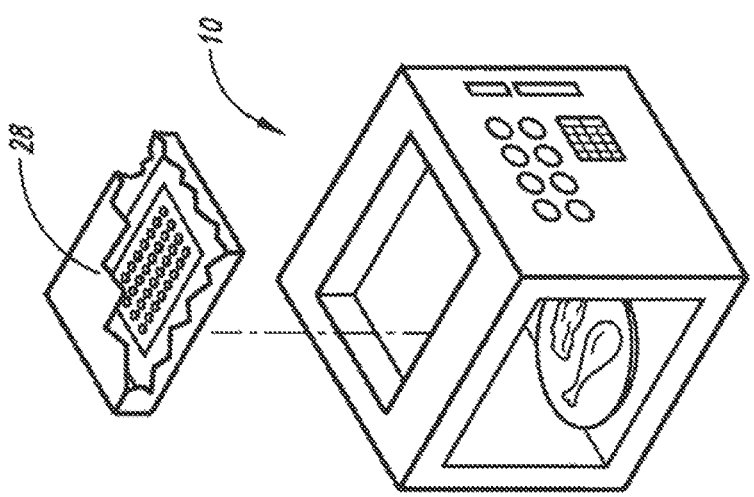
FIG. 4 is a schematic diagram depicting a second exemplary implementation of dispensing controlled substances for the ingestible product preparation system 10 of FIG. 1.
Figure 3:
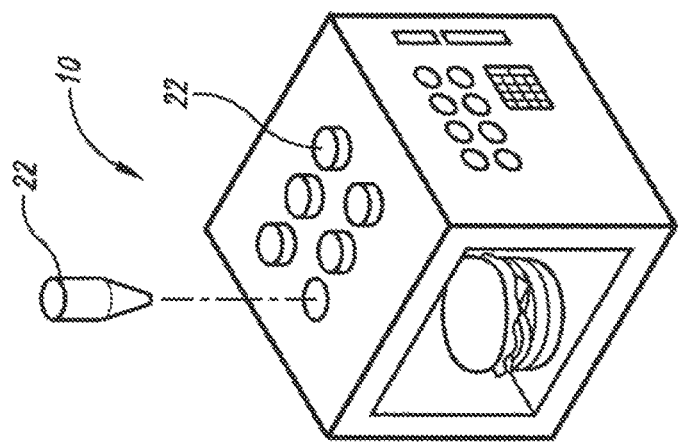
FIG. 3 is a schematic diagram depicting a first exemplary implementation of dispensing controlled substances for the ingestible product preparation system 10 of FIG. 1.

Some examples of ingestible product preparation are depicted by exemplary implementations shown in FIGS. 3-5 of the ingestible product preparation system 10. Such examples include sandwich making, shown in FIG. 3, meal making, shown in FIG. 4, and food bar making, shown in FIG. 5. In addition to the containers 22 depicted in FIG. 3, other depicted storage includes trays of individually housed portions 28 depicted in FIG. 4, and tablets 30 being individually administered as depicted in FIG. 5.

An exemplary version of the ingestible product preparation system 10 is shown in FIG. 6 to optionally include various subsystems such as control and information processing subsystem s100, information storage subsystem s200, information user interface subsystem s300, sensing subsystem s400, electronic communication subsystem s500, power subsystem s600, and material processing subsystem s700.

An exemplary implementation of the control and information processing subsystem s100 is shown in FIG. 7 to optionally include various components such as microprocessor component s102, central processing unit (CPU) component s104, digital signal processor (DSP) component s106, application specific integrated circuit (ASIC) component s108, field programmable gate array (FPGA) component s110, multiprocessor component s112, and optical processing component s114.

An exemplary implementation of the information storage subsystem s200 is shown in FIG. 8 to optionally include various components such as random access memory (RAM) component s202, dynamic random access memory (DRAM) component s204, other volatile memory component s206, persistent memory component s208, read only memory (ROM) component s210, electrically erasable programmable read only memory (EEPROM) component s212, compact disk (CD) component s214, digital versatile disk (DVD) component s216, flash memory component s218, other nonvolatile memory component s220, hard drive component s222, disk farm component s224, disk cluster component s226, remote backup component s228, server component s230, digital tape component s232, optical storage component s234, optical storage component s236, computer readable signal bearing medium s238, and Blu Ray disk component s240.

An exemplary implementation of the information user interface subsystem s300 is shown in FIG. 9 to optionally include various components such as graphical user interface (GUI) component s302, visual display component s304, keyboard component s306, keypad component s308, trackball component s310, joystick component s312, touch screen component s314, mouse component s316, switch component s318, dial component s320, button component s322, gauge component s324, light emitting component s326, audio in/out component s328, vibration emitting component s330, portable information storage reader component s332, projection component s334, camera component s336, and scanner component s338.

An exemplary implementation of the sensing subsystem s400 is shown in FIG. 10 to optionally include various components such as electromagnetic sensing component s402, antenna component s404, photodetecting s406, micro-electro-mechanical system (MEMS) detecting component s408, weight sensing component s410, temperature sensing component s412, radio frequency identification (RFID) sensing component s414, chemical sensing component s416, optical sensing component s418, sound sensing component s420, solid sensing component s422, liquid sensing component s424, and solid sensing component s426.

Figure 11:
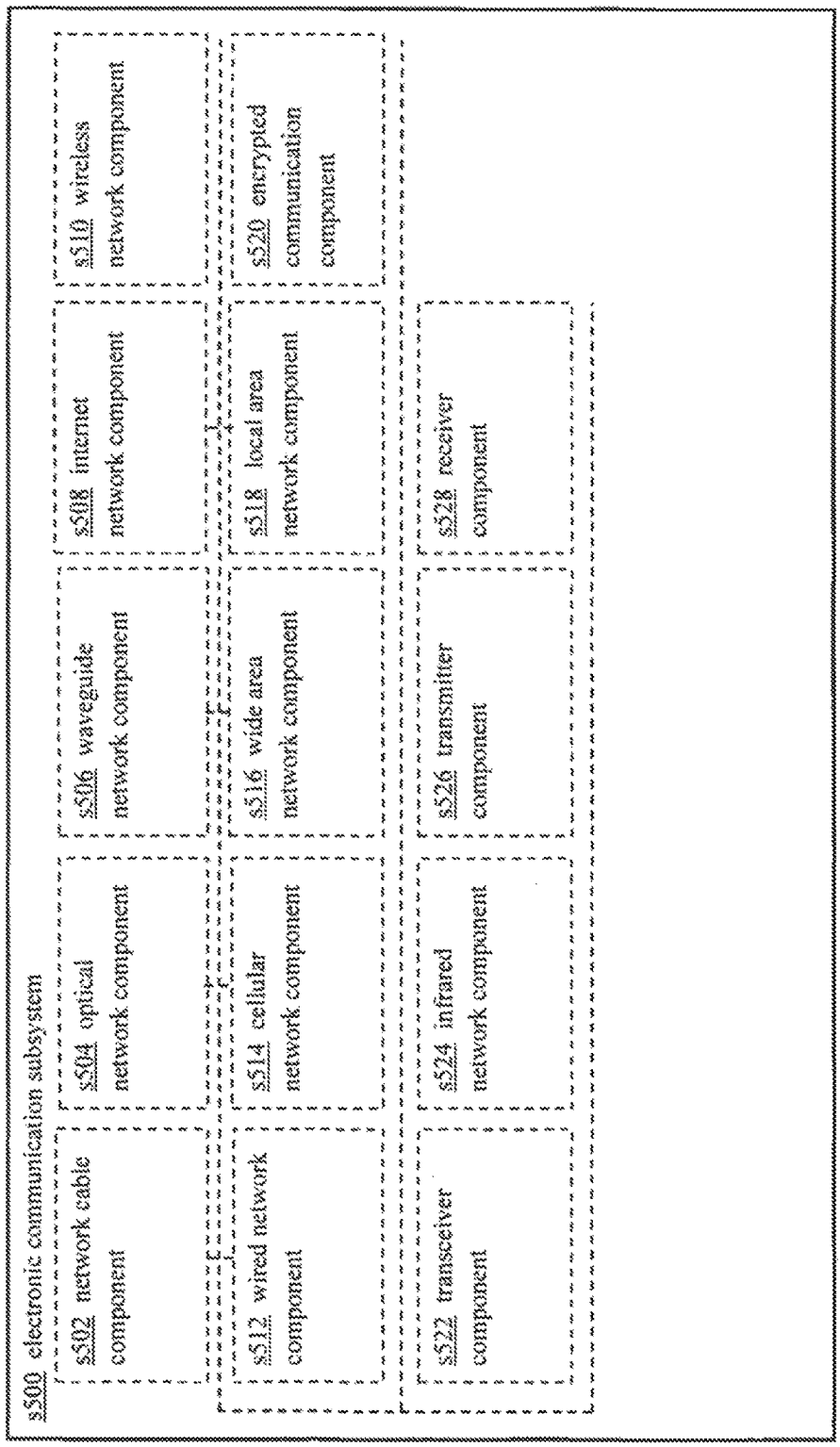
FIG. 11 is a block diagram depicting an electronic communication subsystem s500 of an exemplary implementation of the ingestible product preparation system 10 of FIG. 1.

An exemplary implementation of the electronic communication subsystem s500 is shown in FIG. 11 to optionally include various components such as network cable component s502, optical network component s504, waveguide network component s506, internet network component s508, wireless network component s510, wired network component s512, cellular network component s514, wide area network component s516, local area network component s518, encrypted communication component s520, transceiver component s522, infrared network component s524, transmitter component s526, and receiver component s528.

Figure 12:
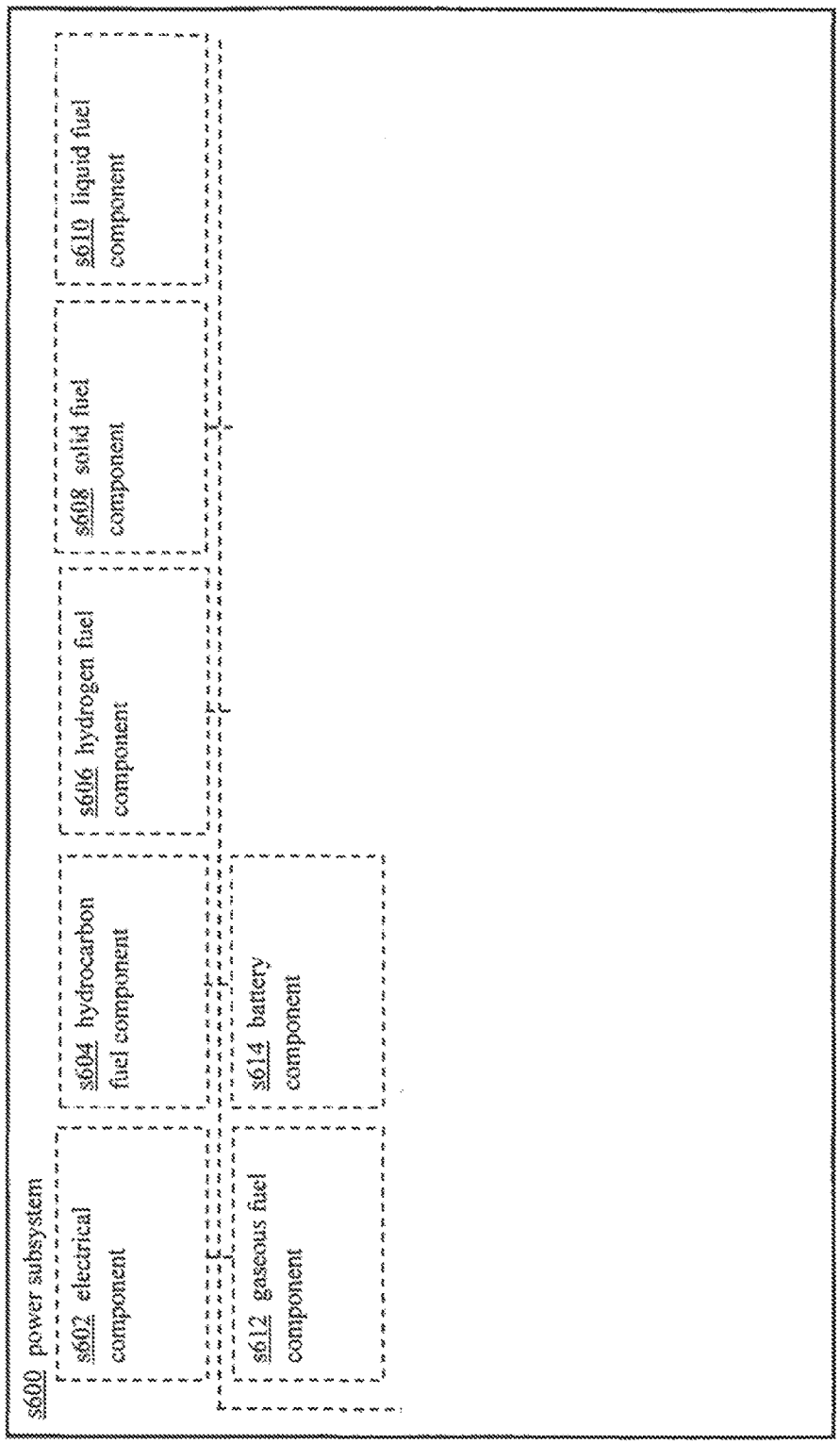
FIG. 12 is a block diagram depicting a power subsystem s600 of an exemplary implementation of the ingestible product preparation system 10 of FIG. 1.

An exemplary implementation of the power subsystem s600 is shown in FIG. 12 to optionally include various components such as electrical component s602, hydrocarbon fuel component s604, hydrogen fuel component s606, solid fuel component s608, liquid fuel component s610, gaseous fuel component s612, and battery component s614.

An exemplary implementation of the material processing subsystem s700 is shown in FIG. 13 to optionally include various components such as heating component s702, cooling component s704, microwave component s706, laser component s708, light emitting diode (LED) component s710, peltier cooling component s712, blending component s714, mixer component s716, acoustic energy component s718, stirring component s720, shaker component s722, energy emitting component s724, pump component s726, sorting component s728, infrared component s730, cutting component s732, and material storage component s734.

Figure 14:
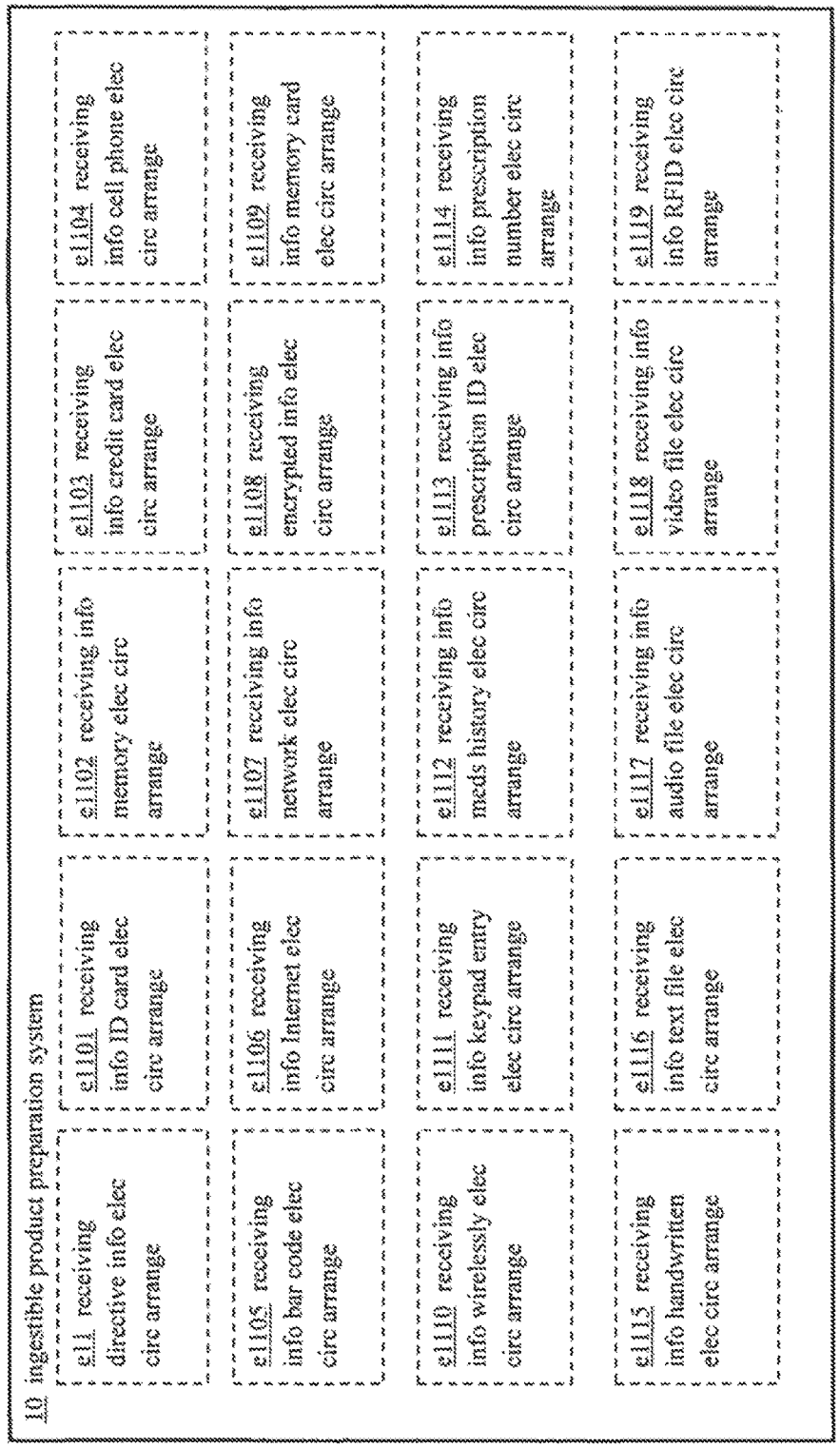
FIG. 14 is a block diagram depicting one or more exemplary electrical circuitry arrangements of the ingestible product preparation system 10 of FIG. 1.

Implementations involve different combinations (otherwise known as "electrical circuitry arrangements") of components from the subsystems of the ingestible product preparation system 10. Exemplary depictions of some of these electrical circuitry arrangements are shown in FIG. 14 to include receiving directive info electrical circuitry arrangement e11, receiving info ID card electrical circuitry arrangement e1101, receiving info memory electrical circuitry arrangement e1102, receiving info credit card electrical circuitry arrangement e1103, receiving info cell phone electrical circuitry arrangement e1104, receiving info bar code electrical circuitry arrangement e1105, receiving info Internet electrical circuitry arrangement e1106, receiving info network electrical circuitry arrangement e1107, receiving encrypted info electrical circuitry arrangement e1108, receiving info memory card electrical circuitry arrangement e1109, receiving info wirelessly electrical circuitry arrangement e1110, receiving info keypad entry electrical circuitry arrangement e1111, receiving info meds history electrical circuitry arrangement e1112, receiving info prescription ID electrical circuitry arrangement e1113, receiving info prescription number electrical circuitry arrangement e1114, receiving info handwritten electrical circuitry arrangement e1115, receiving info text file electrical circuitry arrangement e1116, receiving info audio file electrical circuitry arrangement e1117, receiving info video file electrical circuitry arrangement e1118, and receiving info RFID electrical circuitry arrangement e1119.

Figure 15:
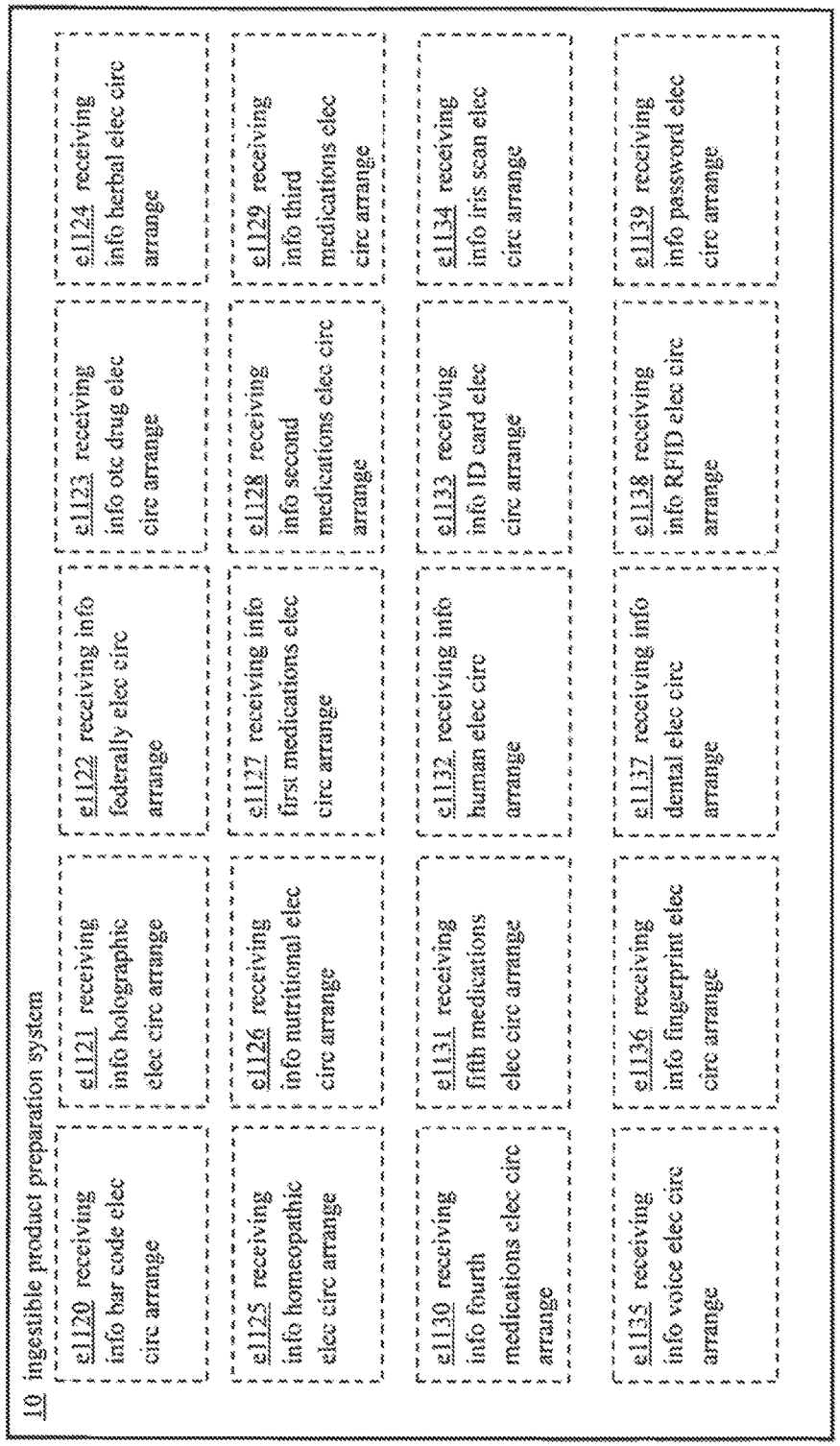
FIG. 15 is a block diagram depicting one or more exemplary electrical circuitry arrangements of the ingestible product preparation system 10 of FIG. 1.

Some of these electrical circuitry arrangements are depicted in FIG. 15 to include receiving info bar code electrical circuitry arrangement e1120, receiving info holographic electrical circuitry arrangement e1121, receiving info federally electrical circuitry arrangement e1122, receiving info otc drug electrical circuitry arrangement e1123, receiving info herbal electrical circuitry arrangement e1124, receiving info homeopathic electrical circuitry arrangement e1125, receiving info nutritional electrical circuitry arrangement e1126, receiving info first medications electrical circuitry arrangement e1127, receiving info second medications electrical circuitry arrangement e1128, receiving info third medications electrical circuitry arrangement e1129, receiving info fourth medications electrical circuitry arrangement e1130, receiving fifth medications electrical circuitry arrangement e113, receiving info human electrical circuitry arrangement e1132, receiving info ID card electrical circuitry arrangement e1133, receiving info iris scan electrical circuitry arrangement e1134, receiving info voice electrical circuitry arrangement e1135, receiving info fingerprint electrical circuitry arrangement e1136, receiving info dental electrical circuitry arrangement e1137, receiving info RFID electrical circuitry arrangement e1138, and receiving info password electrical circuitry arrangement e1139.

Figure 16:
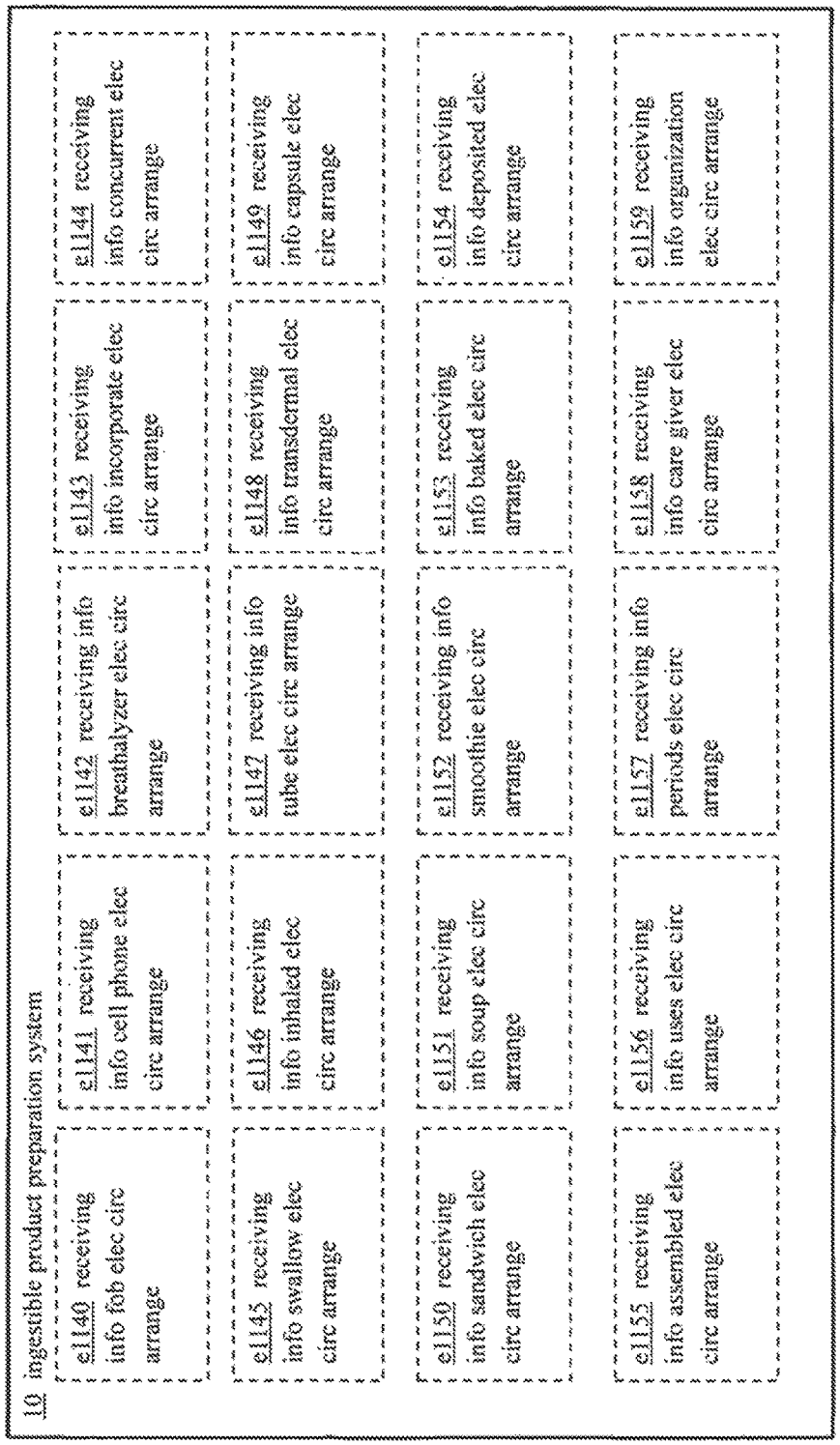
FIG. 16 is a block diagram depicting one or more exemplary electrical circuitry arrangements of the ingestible product preparation system 10 of FIG. 1.

Some of these electrical circuitry arrangements are depicted in FIG. 16 to include receiving info fob electrical circuitry arrangement e1140, receiving info cell phone electrical circuitry arrangement e1141, receiving info breathalyzer electrical circuitry arrangement e1142, receiving info incorporate electrical circuitry arrangement e1143, receiving info concurrent electrical circuitry arrangement e1144, receiving info swallow electrical circuitry arrangement e1145, receiving info inhaled electrical circuitry arrangement e1146, receiving info tube electrical circuitry arrangement e1147, receiving info transdermal electrical circuitry arrangement e1148, receiving info capsule electrical circuitry arrangement e1149, receiving info sandwich electrical circuitry arrangement e1150, receiving info soup electrical circuitry arrangement e1151, receiving info smoothie electrical circuitry arrangement e1152, receiving info baked electrical circuitry arrangement e1153, receiving info deposited electrical circuitry arrangement e1154, receiving info assembled electrical circuitry arrangement e1155, receiving info uses electrical circuitry arrangement e1156, receiving info periods electrical circuitry arrangement e1157, receiving info care giver electrical circuitry arrangement e1158, and receiving info organization electrical circuitry arrangement e1159.

Some of these electrical circuitry arrangements are depicted in FIG. 17 to include receiving info preventive electrical circuitry arrangement e1160, receiving info alternative electrical circuitry arrangement e1161, receiving info authority electrical circuitry arrangement e1162, receiving info individual electrical circuitry arrangement e1163, and receiving info company electrical circuitry arrangement e1164.

Some of these electrical circuitry arrangements are depicted in FIG. 18 to include controlling prep upon verify electrical circuitry arrangement e12, verifying thru comparison electrical circuitry arrangement e1201, verifying thru encryption electrical circuitry arrangement e1202, control prep thermal electrical circuitry arrangement e1203, control prep heating electrical circuitry arrangement e1204, control prep cooling electrical circuitry arrangement e1205, control prep portion size electrical circuitry arrangement e1206, control prep mixing electrical circuitry arrangement e1207, control prep radiation electrical circuitry arrangement e1208, control prep sound electrical circuitry arrangement e1209, control prep infrared electrical circuitry arrangement e1210, control prep microwave electrical circuitry arrangement e1211, control prep container electrical circuitry arrangement e1212, control prep syringe electrical circuitry arrangement e1213, control prep mix before thermal electrical circuitry arrangement e1214, control prep re mix after thermal electrical circuitry arrangement e1215, control prep heating cooling electrical circuitry arrangement e1216, control prep time control electrical circuitry arrangement e1217, control prep ingredient exclusion electrical circuitry arrangement e1218, and control prep ingredient inclusion electrical circuitry arrangement e1219.

Figure 19:
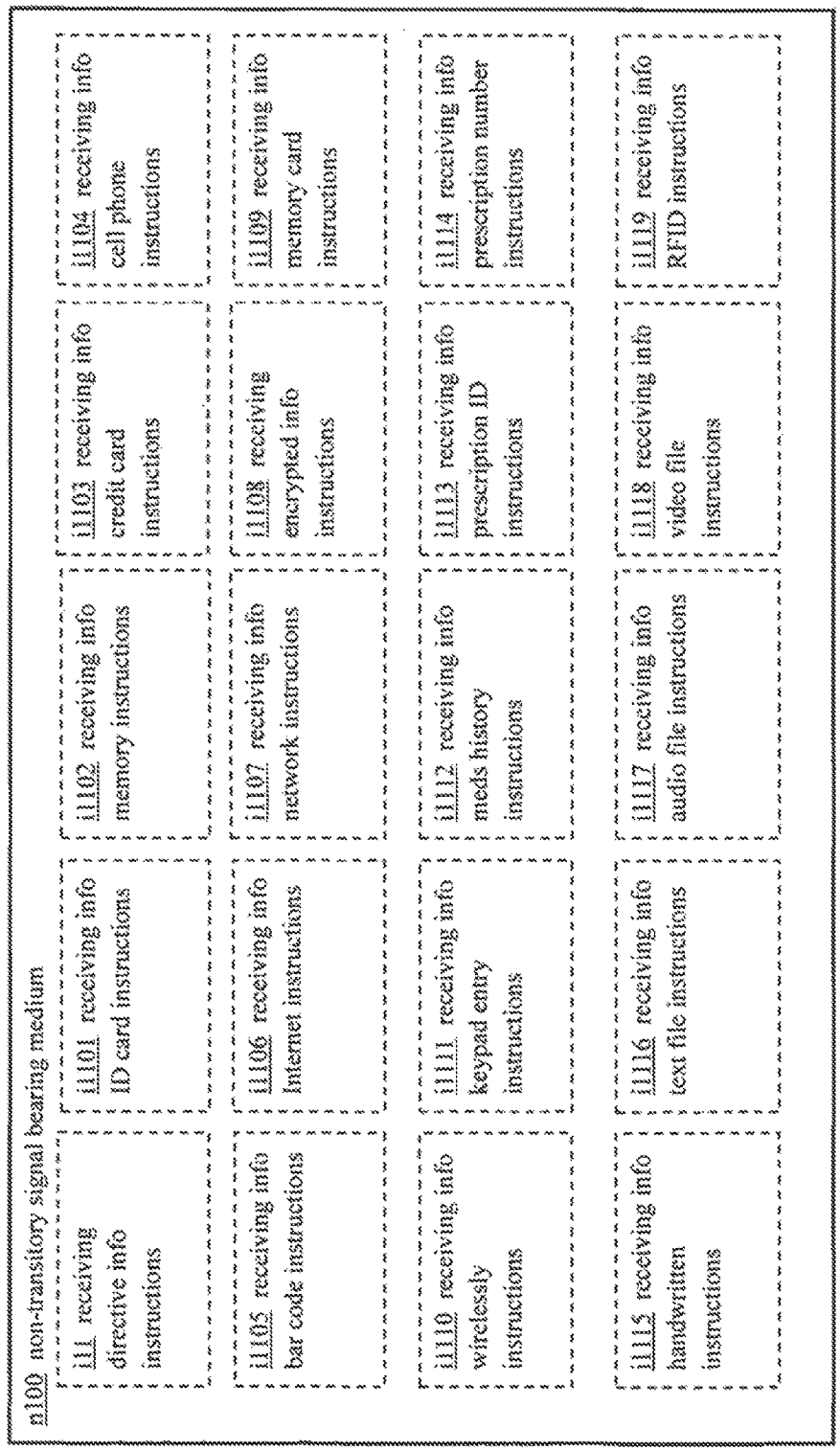
FIG. 19 is a block diagram depicting one or more exemplary instructions of the information storage subsystem s200 of the ingestible product preparation system 10 of FIG. 1.

In implementations one or more instructions are stored and/or otherwise borne in various subsystems, components, and/or accessories of the ingestible product preparation system 10 such as being borne in a non-transitory signal bearing medium n100. One or more exemplary instructions depicted in FIG. 19 as being borne in an exemplary version of the non-transitory signal bearing medium n100 include one or more receiving directive info instructions i11, one or more receiving info ID card instructions i1101, one or more receiving info memory instructions i1102, one or more receiving info credit card instructions i1103, one or more receiving info cell phone instructions i1104, one or more receiving info bar code instructions i1105, one or more receiving info Internet instructions i1106, one or more receiving info network instructions i1107, one or more receiving encrypted info instructions i1108, one or more receiving info memory card instructions i1109, one or more receiving info wirelessly instructions i1110, one or more receiving info keypad entry instructions i1111, one or more receiving info meds history instructions i1112, one or more receiving info prescription ID instructions i1113, one or more receiving info prescription number instructions i1114, one or more receiving info handwritten instructions i1115, one or more receiving info text file instructions i1116, one or more receiving info audio file instructions i1117, one or more receiving info video file instructions i1118, and one or more receiving info RFID instructions i1119.

Figure 20:
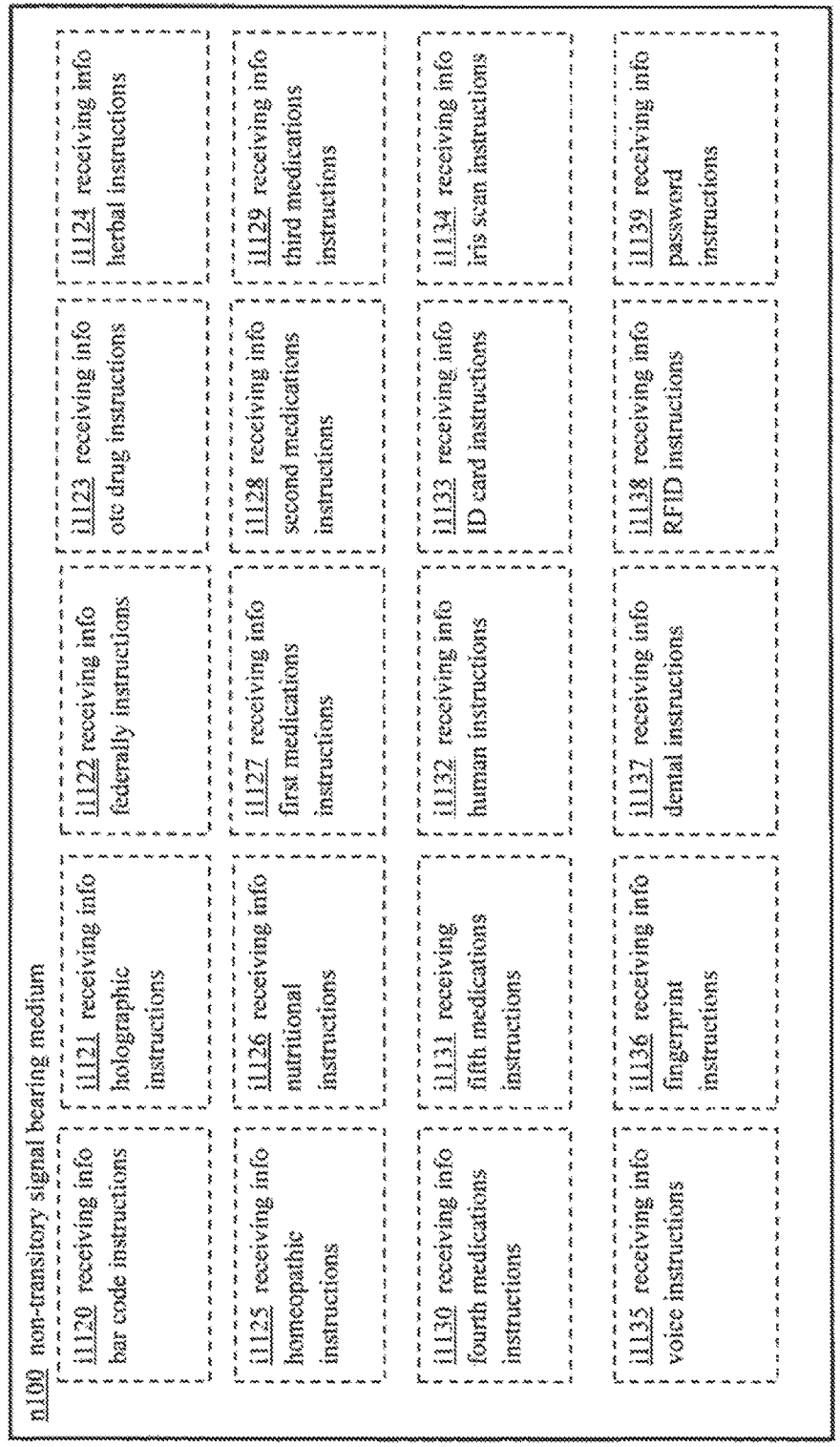
FIG. 20 is a block diagram depicting one or more exemplary instructions of the information storage subsystem s200 of the ingestible product preparation system 10 of FIG. 1.

One or more exemplary instructions depicted in FIG. 20 as being borne in an exemplary version of the non-transitory signal bearing medium n100 include one or more receiving info bar code instructions i1120, one or more receiving info holographic instructions i1121, one or more receiving info federally instructions i1122, one or more receiving info otc drug instructions i1123, one or more receiving info herbal instructions i1124, one or more receiving info homeopathic instructions i1125, one or more receiving info nutritional instructions i1126, one or more receiving info first medications instructions i1127, one or more receiving info second medications instructions i1128, one or more receiving info third medications instructions i1129, one or more receiving info fourth medications instructions i1130, one or more receiving fifth medications instructions i1131, one or more receiving info human instructions i1132, one or more receiving info ID card instructions i1133, one or more receiving info iris scan instructions i1134, one or more receiving info voice instructions i1135, one or more receiving info fingerprint instructions i1136, one or more receiving info dental instructions i1137, one or more receiving info RFID instructions i1138, and one or more receiving info password instructions i1139.

Figure 21:
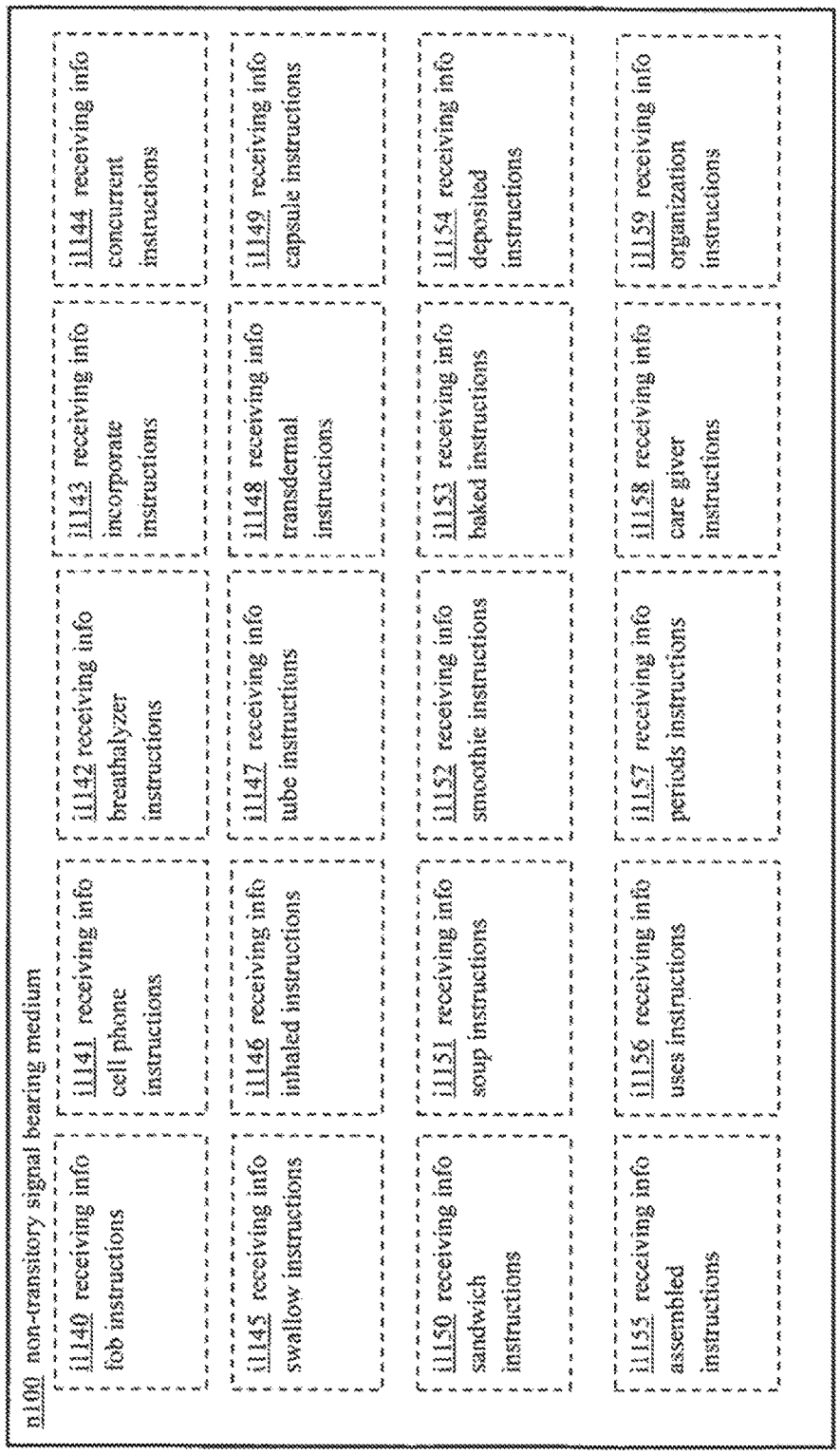
FIG. 21 is a block diagram depicting one or more exemplary instructions of the information storage subsystem s200 of the ingestible product preparation system 10 of FIG. 1.

One or more exemplary instructions depicted in FIG. 21 as being borne in an exemplary version of the non-transitory signal bearing medium n100 include one or more receiving info fob instructions i1140, one or more receiving info cell phone instructions i1141, one or more receiving info breathalyzer instructions i1142, one or more receiving info incorporate instructions i1143, one or more receiving info concurrent instructions i1144, one or more receiving info swallow instructions i1145, one or more receiving info inhaled instructions i1146, one or more receiving info tube instructions i1147, one or more receiving info transdermal instructions i1148, one or more receiving info capsule instructions i1149, one or more receiving info sandwich instructions i1150, one or more receiving info soup instructions i1151, one or more receiving info smoothie instructions i1152, one or more receiving info baked instructions i1153, one or more receiving info deposited instructions i1154, one or more receiving info assembled instructions i1155, one or more receiving info uses instructions i1156, one or more receiving info periods instructions i1157, one or more receiving info care giver instructions i1158, and one or more receiving info organization instructions i1159.

Figure 22:
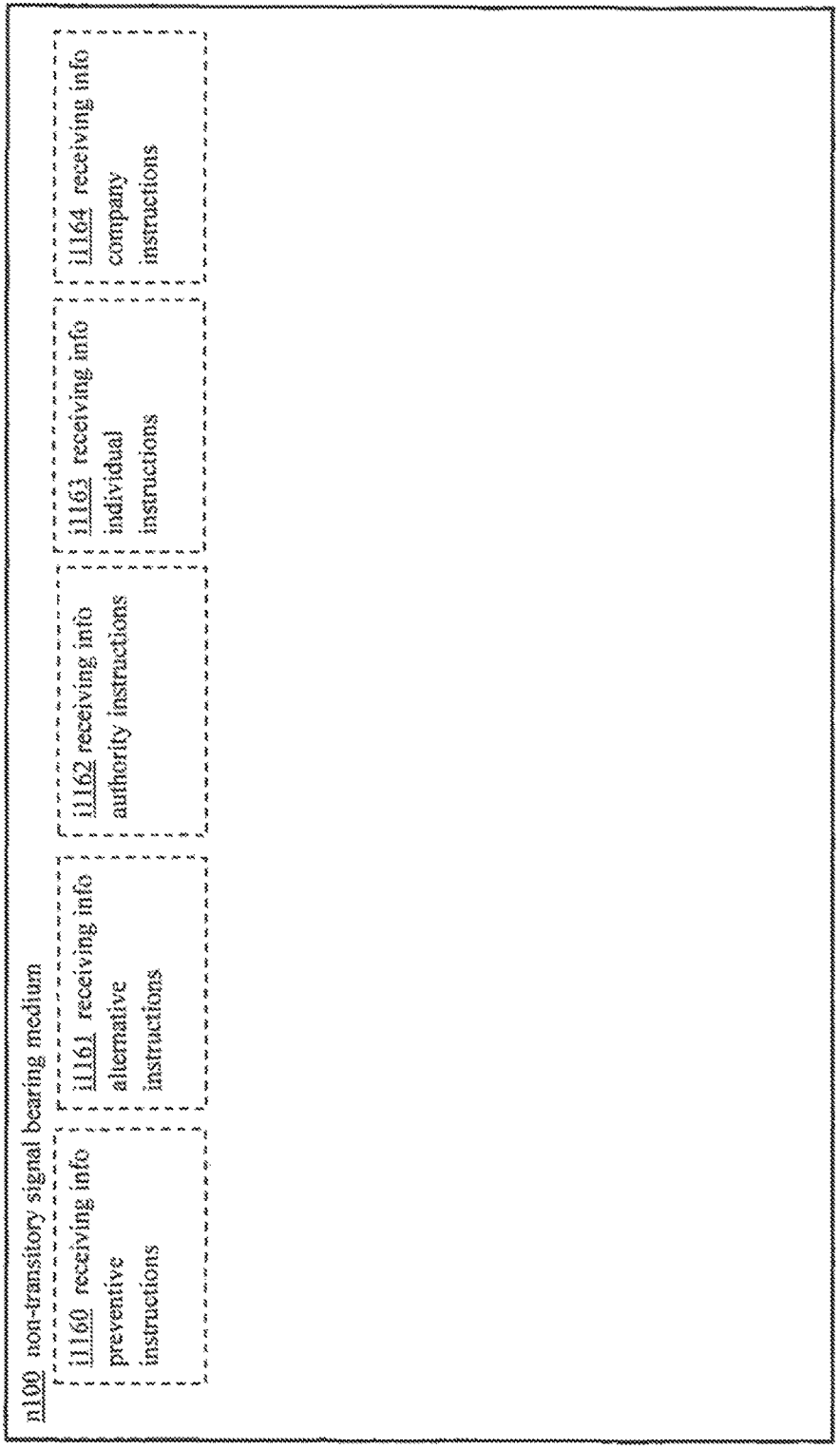
FIG. 22 is a block diagram depicting one or more exemplary instructions of the information storage subsystem s200 of the ingestible product preparation system 10 of FIG. 1.

One or more exemplary instructions depicted in FIG. 22 as being borne in an exemplary version of the non-transitory signal bearing medium n100 include one or more receiving info preventive instructions i1160, one or more receiving info alternative instructions i1161, one or more receiving info authority instructions i1162, one or more receiving info individual instructions i1163, and one or more receiving info company instructions i1164.

One or more exemplary instructions depicted in FIG. 23 as being borne in an exemplary version of the non-transitory signal bearing medium n100 include one or more controlling prep upon verify instructions i12, one or more verifying thru comparison instructions i1201, one or more verifying thru encryption instructions i1202, one or more control prep thermal instructions i1203, one or more control prep heating instructions i1204, one or more control prep cooling instructions i1205, one or more control prep portion size instructions i1206, one or more control prep mixing instructions i1207, one or more control prep radiation instructions i1208, one or more control prep sound instructions i1209, one or more control prep infrared instructions i1210, one or more control prep microwave instructions i1211, one or more control prep container instructions i1212, one or more control prep syringe instructions i1213, one or more control prep mix before thermal instructions i1214, one or more control prep re mix after thermal instructions i1215, one or more control prep heating cooling instructions i1216, one or more control prep time control instructions i1217, one or more control prep ingredient exclusion instructions i1218, and one or more control prep ingredient inclusion instructions i1219.

Figure 24:
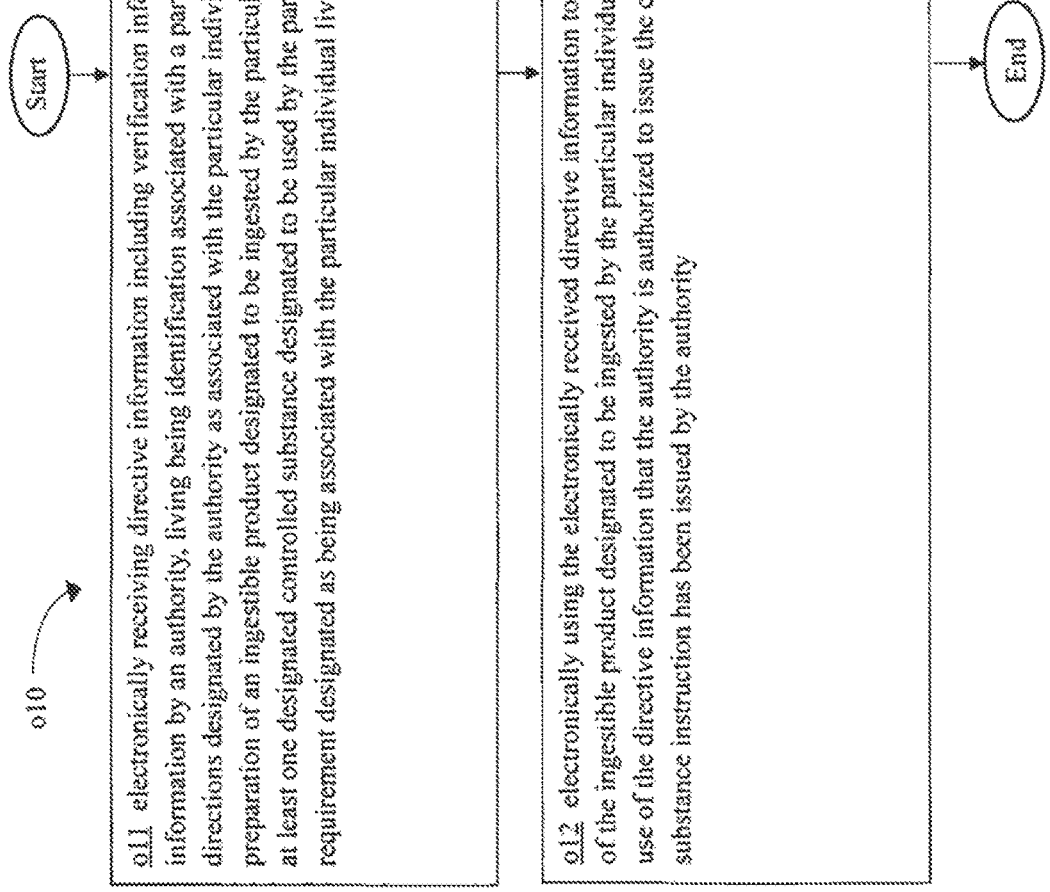
FIG. 24 is a high-level flowchart illustrating an operational flow o10 representing exemplary operations related to electronically receiving directive information including verification information to electronically verify issuance of the directive information by an authority, living being identification associated with a particular individual living being, and controlled substance directions designated by the authority as associated with the particular individual living being for electronically directing at least partial preparation of an ingestible product designated to be ingested by the particular individual living being and designated for involvement with at least one designated controlled substance designated to be used by the particular individual living being according to at least one requirement designated as being associated with the particular individual living being, and electronically using the electronically received directive information to electronically direct control of the at least partial preparation of the ingestible product designated to be ingested by the particular individual living being upon electronically verifying, thru electronic use of the directive information that the authority is authorized to issue the controlled substance instruction and that the controlled substance instruction has been issued by the authority at least associated with the depicted exemplary implementations of the system.

An operational flow o10 as shown in FIG. 24 represents example operations related to receiving authorization information and directing fabrication of ingestible products based upon verification of the authorization.

FIG. 24 and those figures that follow may have various examples of operational flows, and explanation may be provided with respect to the above-described examples of FIGS. 1-24 and/or with respect to other examples and contexts. Nonetheless, it should be understood that the operational flows may be executed in a number of other environments and contexts, and/or in modified versions of FIGS. 1-24. Furthermore, although the various operational flows are presented in the sequence(s) illustrated, it should be understood that the various operations may be performed in other orders than those which are illustrated, or may be performed concurrently.

In FIG. 24 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

As shown in FIG. 24, the operational flow o10 proceeds to operation o11 for electronically receiving directive information including verification information to electronically verify issuance of the directive information by an authority, living being identification associated with a particular individual living being, and controlled substance directions designated by the authority as associated with the particular individual living being for electronically directing at least partial preparation of an ingestible product designated to be ingested by the particular individual living being and designated for involvement with at least one designated controlled substance designated to be used by the particular individual living being according to at least one requirement designated as being associated with the particular individual living being. An exemplary version of the non-transitory signal bearing medium n100 is depicted as bearing one or more receiving directive info instructions i11 that when executed will direct performance of the operation o11. In an implementation, the one or more receiving directive info instructions i11 when executed direct electronically receiving (e.g. the network cable component s502 carries information to the transceiver component s522, etc.) directive information including verification information to electronically verify issuance of the directive information by an authority (e.g. an implementation of the processing component s102 runs a comparison analysis of data contained in the directive information has been issued by a particular authority such as a physician or pharmacist, etc.), living being identification associated with a particular individual living being (e.g. a particular human being, animal, plant, etc.), and controlled substance directions designated by the authority as associated with the particular individual living being for electronically directing at least partial preparation of an ingestible product designated to be ingested by the particular individual living being (e.g. such as partial preparation of a smoothie to be ingested by a human child, etc.) and designated for involvement with at least one designated controlled substance designated (e.g. such as including a pharmaceutical medication in a smoothie for a young child, etc.) to be used by the particular individual living being according to at least one requirement (e.g. such as a pharmaceutical medication to treat a respiratory infection, etc.) designated as being associated with the particular individual living being (e.g. a young child has a respiratory infection that requires treatment, etc.). Furthermore, the receiving directive info electrical circuitry arrangement ("elec circ arrange") e11 when activated will perform the operation o11. In an implementation, the receiving directive info electrical circuitry arrangement e11, when activated performs electronically receiving (e.g. the network cable component s502 carries information to the transceiver component s522, etc.) directive information including verification information to electronically verify issuance of the directive information by an authority (e.g. an implementation of the processing component s102 runs a comparison analysis of data contained in the directive information has been issued by a particular authority such as a physician or pharmacist, etc.), living being identification associated with a particular individual living being (e.g. a particular human being, animal, plant, etc.), and controlled substance directions designated by the authority as associated with the particular individual living being for electronically directing at least partial preparation of an ingestible product designated to be ingested by the particular individual living being (e.g. such as partial preparation of a smoothie to be ingested by a human child, etc.) and designated for involvement with at least one designated controlled substance designated (e.g. such as including a pharmaceutical medication in a smoothie for a young child, etc.) to be used by the particular individual living being according to at least one requirement (e.g. such as a pharmaceutical medication to treat a respiratory infection, etc.) designated as being associated with the particular individual living being (e.g. a young child has a respiratory infection that requires treatment, etc.). In an implementation, the electronically receiving directive information including verification information to electronically verify issuance of the directive information by an authority, living being identification associated with a particular individual living being, and controlled substance directions designated by the authority as associated with the particular individual living being for electronically directing at least partial preparation of an ingestible product designated to be ingested by the particular individual living being and designated for involvement with at least one designated controlled substance designated to be used by the particular individual living being according to at least one requirement designated as being associated with the particular individual living being is carried out by electronically receiving (e.g. the network cable component s502 carries information to the transceiver component s522, etc.) directive information including verification information to electronically verify issuance of the directive information by an authority (e.g. an implementation of the processing component s102 runs a comparison analysis of data contained in the directive information has been issued by a particular authority such as a physician or pharmacist, etc.), living being identification associated with a particular individual living being (e.g. a particular human being, animal, plant, etc.), and controlled substance directions designated by the authority as associated with the particular individual living being for electronically directing at least partial preparation of an ingestible product designated to be ingested by the particular individual living being (e.g. such as partial preparation of a smoothie to be ingested by a human child, etc.) and designated for involvement with at least one designated controlled substance designated (e.g. such as including a pharmaceutical medication in a smoothie for a young child, etc.) to be used by the particular individual living being according to at least one requirement (e.g. such as a pharmaceutical medication to treat a respiratory infection, etc.) designated as being associated with the particular individual living being (e.g. a young child has a respiratory infection that requires treatment, etc.).

Figure 25:
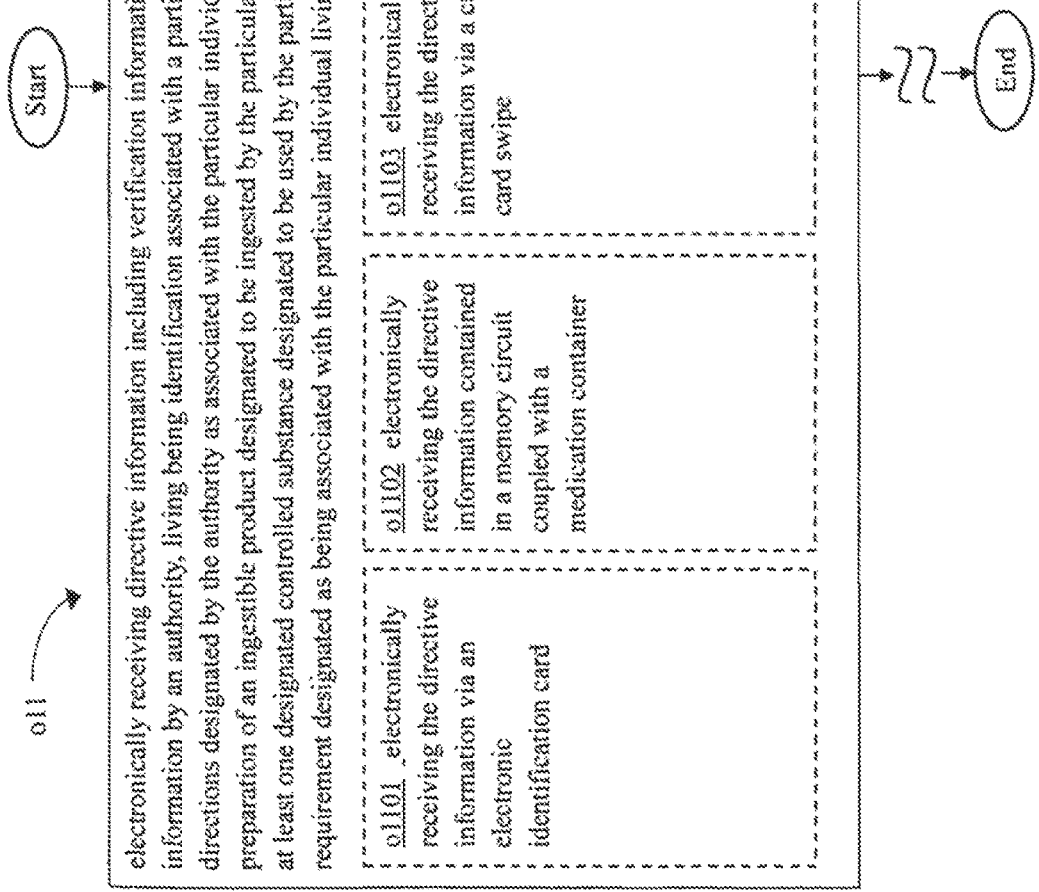
FIG. 25 is a high-level flowchart including exemplary implementations of operation O11 of FIG. 24.

In one or more implementations, as shown in FIG. 25, operation o11 includes an operation o1101 for electronically receiving the directive information via an electronic identification card. An exemplary version of the non-transitory signal bearing medium n100 is depicted as bearing one or more receiving info ID card instructions i1101 that when executed will direct performance of the operation o1101. In an implementation, the one or more receiving info ID card instructions i1101 when executed direct electronically receiving the directive information via an electronic identification card (e.g. an implementation of the receiver component s528 is configured to electronically engage with a card having memory storage holding the direction information, etc.). Furthermore, the receiving info ID card electrical circuitry arrangement ("elec circ arrange") e1101 when activated will perform the operation o1101. In an implementation, the receiving info ID card electrical circuitry arrangement e1101, when activated performs electronically receiving the directive information via an electronic identification card (e.g. an implementation of the receiver component s528 is configured to electronically engage with a card having memory storage holding the direction information, etc.). In an implementation, the electronically receiving the directive information via an electronic identification card is carried out by electronically receiving the directive information via an electronic identification card (e.g. an implementation of the receiver component s528 is configured to electronically engage with a card having memory storage holding the direction information, etc.).

In one or more implementations, operation o11 includes an operation o1102 for electronically receiving the directive information contained in a memory circuit coupled with a medication container. An exemplary version of the non-transitory signal bearing medium n100 is depicted as bearing one or more receiving info memory instructions i1102 that when executed will direct performance of the operation o1102. In an implementation, the one or more receiving info memory instructions i1102 when executed direct electronically receiving the directive information contained in a memory circuit coupled with a medication container (e.g. an implementation of the receiver component s528 is configured to electronically engage with a memory storage coupled with a medication container to receive the directive information in electronic form, etc.). Furthermore, the receiving info memory electrical circuitry arrangement e1102 when activated will perform the operation o1102. In an implementation, the receiving info memory electrical circuitry arrangement e1102, when activated performs electronically receiving the directive information contained in a memory circuit coupled with a medication container (e.g. an implementation of the receiver component s528 is configured to electronically engage with a memory storage coupled with a medication container to receive the directive information in electronic form, etc.). In an implementation, the electronically receiving the directive information contained in a memory circuit coupled with a medication container is carried out by electronically receiving the directive information contained in a memory circuit coupled with a medication container (e.g. an implementation of the receiver component s528 is configured to electronically engage with a memory storage coupled with a medication container to receive the directive information in electronic form, etc.).

In one or more implementations, operation o11 includes an operation o1103 for electronically receiving the directive information via a credit card swipe. An exemplary version of the non-transitory signal bearing medium n100 is depicted as bearing one or more receiving info credit card instructions i1103 that when executed will direct performance of the operation o1103. In an implementation, the one or more receiving info credit card instructions i1103 when executed direct electronically receiving the directive information via a credit card swipe (e.g. an implementation of the receiver component s528 is configured to electronically engage with an electronic memory stripe integrated into a credit card to receive the directive information, etc.). Furthermore, the receiving info credit card electrical circuitry arrangement e1103 when activated will perform the operation o1103. In an implementation, the receiving info credit card electrical circuitry arrangement e1103, when activated performs electronically receiving the directive information via a credit card swipe (e.g. an implementation of the receiver component s528 is configured to electronically engage with an electronic memory stripe integrated into a credit card to receive the directive information, etc.). In an implementation, the is electronically receiving the directive information via a credit card swipe carried out by electronically receiving the directive information via a credit card swipe (e.g. an implementation of the receiver component s528 is configured to electronically engage with an electronic memory stripe integrated into a credit card to receive the directive information, etc.).

In one or more implementations, operation o11 includes an operation o1104 for electronically receiving the directive information via cell phone swipe. An exemplary version of the non-transitory signal bearing medium n100 is depicted as bearing one or more receiving info cell phone instructions i1104 that when executed will direct performance of the operation o1104. In an implementation, the one or more receiving info cell phone instructions i1104 when executed direct electronically receiving the directive information via cell phone swipe (e.g. an implementation of the receiver component s528 is configured to electronically engage with an electronic memory component integrated into a cell phone to receive the directive information, etc.). Furthermore, the receiving info cell phone electrical circuitry arrangement e1104 when activated will perform the operation o1104. In an implementation, the receiving info cell phone electrical circuitry arrangement e1104, when activated performs electronically receiving the directive information via cell phone swipe (e.g. an implementation of the receiver component s528 is configured to electronically engage with an electronic memory component integrated into a cell phone to receive the directive information, etc.). In an implementation, the is electronically receiving the directive information via cell phone swipe carried out by electronically receiving the directive information via cell phone swipe (e.g. an implementation of the receiver component s528 is configured to electronically engage with an electronic memory component integrated into a cell phone to receive the directive information, etc.).

In one or more implementations, operation o11 includes an operation o1105 for electronically receiving the directive information via bar code communication. An exemplary version of the non-transitory signal bearing medium n100 is depicted as bearing one or more receiving info bar code instructions i1105 that when executed will direct performance of the operation o1105. In an implementation, the one or more receiving info bar code instructions i1105 when executed direct electronically receiving the directive information via bar code communication (e.g. an implementation of the receiver component s528 is configured to electronically read a bar code label to receive the directive information, etc.). Furthermore, the receiving info bar code electrical circuitry arrangement e1105 when activated will perform the operation o1105. In an implementation, the receiving info bar code electrical circuitry arrangement e1105, when activated performs electronically receiving the directive information via bar code communication (e.g. an implementation of the receiver component s528 is configured to electronically read a bar code label to receive the directive information, etc.). In an implementation, the electronically receiving the directive information via bar code communication is carried out by electronically receiving the directive information via bar code communication (e.g. an implementation of the receiver component s528 is configured to electronically read a bar code label to receive the directive information, etc.).

Figure 26:
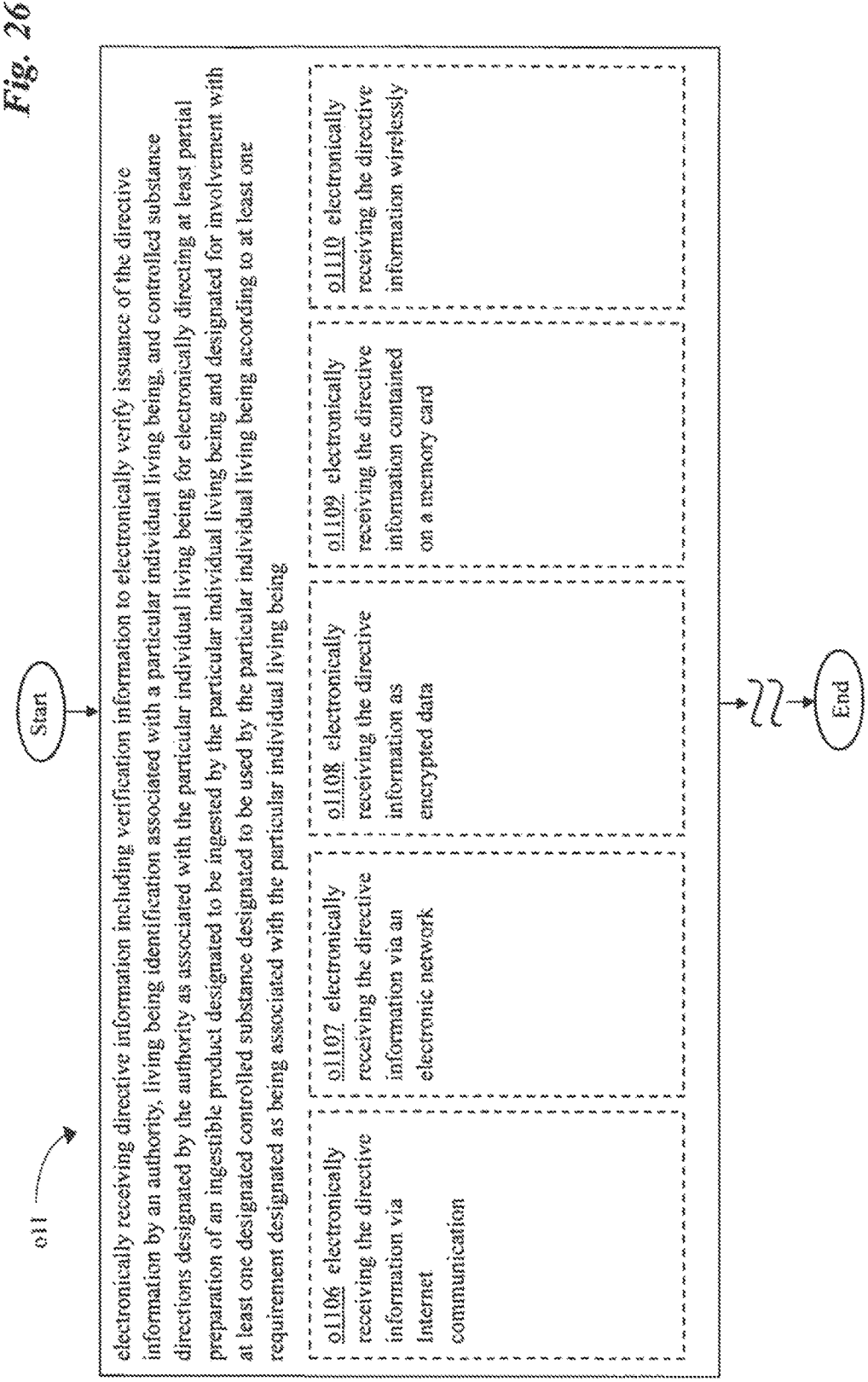
FIG. 26 is a high-level flowchart including exemplary implementations of operation O11 of FIG. 24.

In one or more implementations, as shown in FIG. 26, operation o11 includes an operation o1106 for electronically receiving the directive information via Internet communication. An exemplary version of the non-transitory signal bearing medium n100 is depicted as bearing one or more receiving info Internet instructions i1106 that when executed will direct performance of the operation o1106. In an implementation, the one or more receiving info Internet instructions i1106 when executed direct electronically receiving the directive information via Internet communication (e.g. an implementation of the receiver component s528 is configured to electronically receive through the internet network component s508 the directive information, etc.). Furthermore, the receiving info Internet electrical circuitry arrangement e1106 when activated will perform the operation o1106. In an implementation, the receiving info Internet electrical circuitry arrangement e1106, when activated performs electronically receiving the directive information via Internet communication (e.g. an implementation of the receiver component s528 is configured to electronically receive through the internet network component s508 the directive information, etc.). In an implementation, the electronically receiving the directive information via Internet communication is carried out by electronically receiving the directive information via Internet communication (e.g. an implementation of the receiver component s528 is configured to electronically receive through the interne network component s508 the directive information, etc.).

In one or more implementations, operation o11 includes an operation o1107 for electronically receiving the directive information via an electronic network. An exemplary version of the non-transitory signal bearing medium n100 is depicted as bearing one or more receiving info network instructions i1107 that when executed will direct performance of the operation o1107. In an implementation, the one or more receiving info network instructions i1107 when executed direct electronically receiving the directive information via an electronic network (e.g. an implementation of the receiver component s528 is configured to electronically engage with the network cable component s502 to receive the directive information, etc.). Furthermore, the receiving info network electrical circuitry arrangement e1107 when activated will perform the operation o1107. In an implementation, the receiving info network electrical circuitry arrangement e1107, when activated performs electronically receiving the directive information via an electronic network (e.g. an implementation of the receiver component s528 is configured to electronically engage with the network cable component s502 to receive the directive information, etc.). In an implementation, the electronically receiving the directive information via an electronic network is carried out by electronically receiving the directive information via an electronic network (e.g. an implementation of the receiver component s528 is configured to electronically engage with the network cable component s502 to receive the directive information, etc.).

In one or more implementations, operation o11 includes an operation o1108 for electronically receiving the directive information as encrypted data. An exemplary version of the non-transitory signal bearing medium n100 is depicted as bearing one or more receiving encrypted info instructions i1108 that when executed will direct performance of the operation o1108. In an implementation, the one or more receiving encrypted info instructions i1108 when executed direct electronically receiving the directive information as encrypted data (e.g. an implementation of the receiver component s528 is configured to electronically receive through the encrypted communication component s520 the directive information, etc.). Furthermore, the receiving encrypted info electrical circuitry arrangement e1108 when activated will perform the operation o1108. In an implementation, the receiving encrypted info electrical circuitry arrangement e1108, when activated performs electronically receiving the directive information as encrypted data (e.g. an implementation of the receiver component s528 is configured to electronically receive through the encrypted communication component s520 the directive information, etc.). In an implementation, the electronically receiving the directive information as encrypted data is carried out by electronically receiving the directive information as encrypted data (e.g. an implementation of the receiver component s528 is configured to electronically receive through the encrypted communication component s520 the directive information, etc.).

In one or more implementations, operation o11 includes an operation o1109 for electronically receiving the directive information contained on a memory card. An exemplary version of the non-transitory signal bearing medium n100 is depicted as bearing one or more receiving info memory card instructions i1109 that when executed will direct performance of the operation o1109. In an implementation, the one or more receiving info memory card instructions i1109 when executed direct electronically receiving the directive information contained on a memory card (e.g. an implementation of the receiver component s528 is configured to electronically engage with an electronic memory card to receive the directive information, etc.). Furthermore, the receiving info memory card electrical circuitry arrangement e1109 when activated will perform the operation o1109. In an implementation, the receiving info memory card electrical circuitry arrangement e1109, when activated performs electronically receiving the directive information contained on a memory card (e.g. an implementation of the receiver component s528 is configured to electronically engage with an electronic memory card to receive the directive information, etc.). In an implementation, the electronically receiving the directive information contained on a memory card is carried out by electronically receiving the directive information contained on a memory card (e.g. an implementation of the receiver component s528 is configured to electronically engage with an electronic memory card to receive the directive information, etc.).

In one or more implementations, operation o11 includes an operation o1110 for electronically receiving the directive information wirelessly. An exemplary version of the non-transitory signal bearing medium n100 is depicted as bearing one or more receiving info wirelessly instructions i1110 that when executed will direct performance of the operation o1110. In an implementation, the one or more receiving info wirelessly instructions i1110 when executed direct electronically receiving the directive information wirelessly (e.g. an implementation of the receiver component s528 is configured to electronically receive through the wireless network component s512 the directive information, etc.). Furthermore, the receiving info wirelessly electrical circuitry arrangement e1110 when activated will perform the operation o1110. In an implementation, the receiving info wirelessly electrical circuitry arrangement e1110, when activated performs electronically receiving the directive information wirelessly (e.g. an implementation of the receiver component s528 is configured to electronically receive through the wireless network component s512 the directive information, etc.). In an implementation, the electronically receiving the directive information wirelessly is carried out by electronically receiving the directive information wirelessly (e.g. an implementation of the receiver component s528 is configured to electronically receive through the wireless network component s512 the directive information, etc.).

In one or more implementations, as shown in FIG. 27, operation o11 includes an operation o1111 for electronically receiving the directive information via electronic keypad entry. An exemplary version of the non-transitory signal bearing medium n100 is depicted as bearing one or more receiving info keypad entry instructions i1111 that when executed will direct performance of the operation o1111. In an implementation, the one or more receiving info keypad entry instructions i1111 when executed direct electronically receiving the directive information via electronic keypad entry (e.g. an implementation of the receiver component s528 is configured to electronically engage with the keypad component s308 to receive the directive information as inputted by a user, etc.). Furthermore, the receiving info keypad entry electrical circuitry arrangement e1111 when activated will perform the operation o1111. In an implementation, the receiving info keypad entry electrical circuitry arrangement e1111, when activated performs electronically receiving the directive information via electronic keypad entry (e.g. an implementation of the receiver component s528 is configured to electronically engage with the keypad component s308 to receive the directive information as inputted by a user, etc.). In an implementation, the electronically receiving the directive information via electronic keypad entry is carried out by electronically receiving the directive information via electronic keypad entry (e.g. an implementation of the receiver component s528 is configured to electronically engage with the keypad component s308 to receive the directive information as inputted by a user, etc.).

In one or more implementations, operation o11 includes an operation o1112 for electronically receiving the directive information including substance identification associated with the at least one controlled substance as associated with a medication history. An exemplary version of the non-transitory signal bearing medium n100 is depicted as bearing one or more receiving info meds history instructions i1112 that when executed will direct performance of the operation o1112. In an implementation, the one or more receiving info meds history instructions i1112 when executed direct electronically receiving the directive information including substance identification associated with the at least one controlled substance as associated with a medication history (e.g. an implementation of the receiver component s528 is configured to electronically engage with the processor component s102 to receive the directive information including substance identification as determined by the processor component to identify name and control number of the at least one controlled substance and the name and control number of the medication history of the particular individual living being, etc.). Furthermore, the receiving info meds history electrical circuitry arrangement e1112 when activated will perform the operation o1112. In an implementation, the receiving info meds history electrical circuitry arrangement e1112, when activated performs electronically receiving the directive information including substance identification associated with the at least one controlled substance as associated with a medication history (e.g. an implementation of the receiver component s528 is configured to electronically engage with the processor component s102 to receive the directive information including substance identification as determined by the processor component to identify name and control number of the at least one controlled substance and the name and control number of the medication history of the particular individual living being, etc.). In an implementation, the electronically receiving the directive information including substance identification associated with the at least one controlled substance as associated with a medication history is carried out by electronically receiving the directive information including substance identification associated with the at least one controlled substance as associated with a medication history (e.g. an implementation of the receiver component s528 is configured to electronically engage with the processor component s102 to receive the directive information including substance identification as determined by the processor component to identify name and control number of the at least one controlled substance and the name and control number of the medication history of the particular individual living being, etc.).

In one or more implementations, operation o11 includes an operation o1113 for electronically receiving the directive information including substance identification associated with a prescription identification. An exemplary version of the non-transitory signal bearing medium n100 is depicted as bearing one or more receiving info prescription ID instructions i1113 that when executed will direct performance of the operation o1113. In an implementation, the one or more receiving info prescription ID instructions i1113 when executed direct electronically receiving the directive information including substance identification associated with a prescription identification (e.g. an implementation of the receiver component s528 is configured to electronically engage with the processor component s102 to receive the directive information including substance identification as determined by the processor component to include a name of an issuing physician, etc.). Furthermore, the receiving info prescription ID electrical circuitry arrangement e1113 when activated will perform the operation o1113. In an implementation, the receiving info prescription ID electrical circuitry arrangement e1113, when activated performs electronically receiving the directive information including substance identification associated with a prescription identification (e.g. an implementation of the receiver component s528 is configured to electronically engage with the processor component s102 to receive the directive information including substance identification as determined by the processor component to include a name of an issuing physician, etc.). In an implementation, the electronically receiving the directive information including substance identification associated with a prescription identification is carried out by electronically receiving the directive information including substance identification associated with a prescription identification (e.g. an implementation of the receiver component s528 is configured to electronically engage with the processor component s102 to receive the directive information including substance identification as determined by the processor component to include a name of an issuing physician, etc.).

In one or more implementations, operation o11 includes an operation o1114 for electronically receiving the directive information including substance identification associated with a prescription serial number. An exemplary version of the non-transitory signal bearing medium n100 is depicted as bearing one or more receiving info prescription number instructions i1114 that when executed will direct performance of the operation o1114. In an implementation, the one or more receiving info prescription number instructions i1114 when executed direct electronically receiving the directive information including substance identification associated with a prescription serial number (e.g. an implementation of the receiver component s528 is configured to electronically engage with the processor component s102 to receive the directive information including substance identification as determined by the processor component to include a prescription serial number for the controlled substance, etc.). Furthermore, the receiving info prescription number electrical circuitry arrangement e1114 when activated will perform the operation o1114. In an implementation, the receiving info prescription number electrical circuitry arrangement e1114, when activated performs electronically receiving the directive information including substance identification associated with a prescription serial number (e.g. an implementation of the receiver component s528 is configured to electronically engage with the processor component s102 to receive the directive information including substance identification as determined by the processor component to include a prescription serial number for the controlled substance, etc.). In an implementation, the electronically receiving the directive information including substance identification associated with a prescription serial number is carried out by electronically receiving the directive information including substance identification associated with a prescription serial number (e.g. an implementation of the receiver component s528 is configured to electronically engage with the processor component s102 to receive the directive information including substance identification as determined by the processor component to include a prescription serial number for the controlled substance, etc.).

In one or more implementations, operation o11 includes an operation o1115 for electronically receiving the directive information including substance identification associated with a data image of handwritten text. An exemplary version of the non-transitory signal bearing medium n100 is depicted as bearing one or more receiving info handwritten instructions i1115 that when executed will direct performance of the operation o1115. In an implementation, the one or more receiving info handwritten instructions i1115 when executed direct electronically receiving the directive information including substance identification associated with a data image of handwritten text (e.g. an implementation of the receiver component s528 is configured to electronically engage with the processor component s102 to receive the directive information including a name of the controlled substance as determined by the processor component through electronic handwriting analysis of the data image of the handwritten text, etc.). Furthermore, the receiving info handwritten electrical circuitry arrangement e1115 when activated will perform the operation o1115. In an implementation, the receiving info handwritten electrical circuitry arrangement e1115, when activated performs electronically receiving the directive information including substance identification associated with a data image of handwritten text (e.g. an implementation of the receiver component s528 is configured to electronically engage with the processor component s102 to receive the directive information including a name of the controlled substance as determined by the processor component through electronic handwriting analysis of the data image of the handwritten text, etc.). In an implementation, the electronically receiving the directive information including substance identification associated with a data image of handwritten text is carried out by electronically receiving the directive information including substance identification associated with a data image of handwritten text (e.g. an implementation of the receiver component s528 is configured to electronically engage with the processor component s102 to receive the directive information including a name of the controlled substance as determined by the processor component through electronic handwriting analysis of the data image of the handwritten text, etc.).

In one or more implementations, as shown in FIG. 28, operation o11 includes an operation o1116 for electronically receiving the directive information including substance identification associated with a computer text file. An exemplary version of the non-transitory signal bearing medium n100 is depicted as bearing one or more receiving info text file instructions i1116 that when executed will direct performance of the operation o1116. In an implementation, the one or more receiving info text file instructions i1116 when executed direct electronically receiving the directive information including substance identification associated with a computer text file (e.g. an implementation of the receiver component s528 is configured to electronically engage with the processor component s102 to receive the directive information including substance identification as determined by the processor component through electronic reading of the computer text file, etc.). Furthermore, the receiving info text file electrical circuitry arrangement e1116 when activated will perform the operation o1116. In an implementation, the receiving info text file electrical circuitry arrangement e1116, when activated performs electronically receiving the directive information including substance identification associated with a computer text file (e.g. an implementation of the receiver component s528 is configured to electronically engage with the processor component s102 to receive the directive information including substance identification as determined by the processor component through electronic reading of the computer text file, etc.). In an implementation, the electronically receiving the directive information including substance identification associated with a computer text file is carried out by electronically receiving the directive information including substance identification associated with a computer text file (e.g. an implementation of the receiver component s528 is configured to electronically engage with the processor component s102 to receive the directive information including substance identification as determined by the processor component through electronic reading of the computer text file, etc.).

In one or more implementations, operation o11 includes an operation o1117 for electronically receiving the directive information including substance identification associated with a computer audio file. An exemplary version of the non-transitory signal bearing medium n100 is depicted as bearing one or more receiving info audio file instructions i1117 that when executed will direct performance of the operation o1117. In an implementation, the one or more receiving info audio file instructions i1117 when executed direct electronically receiving the directive information including substance identification associated with a computer audio file (e.g. an implementation of the receiver component s528 is configured to electronically engage with the processor component s102 to receive the directive information including substance identification as determined by the processor component through electronic reading of the computer audio file, etc.). Furthermore, the receiving info audio file electrical circuitry arrangement e1117 when activated will perform the operation o1117. In an implementation, the receiving info audio file electrical circuitry arrangement e1117, when activated performs electronically receiving the directive information including substance identification associated with a computer audio file (e.g. an implementation of the receiver component s528 is configured to electronically engage with the processor component s102 to receive the directive information including substance identification as determined by the processor component through electronic reading of the computer audio file, etc.). In an implementation, the electronically receiving the directive information including substance identification associated with a computer audio file is carried out by electronically receiving the directive information including substance identification associated with a computer audio file (e.g. an implementation of the receiver component s528 is configured to electronically engage with the processor component s102 to receive the directive information including substance identification as determined by the processor component through electronic reading of the computer audio file, etc.).

In one or more implementations, operation o11 includes an operation o1118 for electronically receiving the directive information including substance identification associated with a computer video file. An exemplary version of the non-transitory signal bearing medium n100 is depicted as bearing one or more receiving info video file instructions i1118 that when executed will direct performance of the operation o1118. In an implementation, the one or more receiving info video file instructions i1118 when executed direct electronically receiving the directive information including substance identification associated with a computer video file (e.g. an implementation of the receiver component s528 is configured to electronically engage with the processor component s102 to receive the directive information including substance identification as determined by the processor component through electronic reading of the computer video file, etc.). Furthermore, the receiving info video file electrical circuitry arrangement e1118 when activated will perform the operation o1118. In an implementation, the receiving info video file electrical circuitry arrangement e1118, when activated performs electronically receiving the directive information including substance identification associated with a computer video file (e.g. an implementation of the receiver component s528 is configured to electronically engage with the processor component s102 to receive the directive information including substance identification as determined by the processor component through electronic reading of the computer video file, etc.). In an implementation, the electronically receiving the directive information including substance identification associated with a computer video file is carried out by electronically receiving the directive information including substance identification associated with a computer video file (e.g. an implementation of the receiver component s528 is configured to electronically engage with the processor component s102 to receive the directive information including substance identification as determined by the processor component through electronic reading of the computer video file, etc.).

In one or more implementations, operation o11 includes an operation o1119 for electronically receiving the directive information including substance identification associated with an RFID tag. An exemplary version of the non-transitory signal bearing medium n100 is depicted as bearing one or more receiving info RFID instructions i1119 that when executed will direct performance of the operation o1119. In an implementation, the one or more receiving info RFID instructions i1119 when executed direct electronically receiving the directive information including substance identification associated with an RFID tag (e.g. an implementation of the receiver component s528 is configured to electronically engage with the processor component s102 to receive the directive information including substance identification as determined by the processor component through electronic reading be the radio frequency identification (RFID) sensing component s414 of the RFID tag, etc.). Furthermore, the receiving info RFID electrical circuitry arrangement e1119 when activated will perform the operation o1119. In an implementation, the receiving info RFID electrical circuitry arrangement e1119, when activated performs electronically receiving the directive information including substance identification associated with an RFID tag (e.g. an implementation of the receiver component s528 is configured to electronically engage with the processor component s102 to receive the directive information including substance identification as determined by the processor component through electronic reading be the radio frequency identification (RFID) sensing component s414 of the RFID tag, etc.). In an implementation, the electronically receiving the directive information including substance identification associated with an RFID tag is carried out by electronically receiving the directive information including substance identification associated with an RFID tag (e.g. an implementation of the receiver component s528 is configured to electronically engage with the processor component s102 to receive the directive information including substance identification as determined by the processor component through electronic reading be the radio frequency identification (RFID) sensing component s414 of the RFID tag, etc.).

In one or more implementations, operation o11 includes an operation o1120 for electronically receiving the directive information including substance identification associated with a bar code. An exemplary version of the non-transitory signal bearing medium n100 is depicted as bearing one or more receiving info bar code instructions i1120 that when executed will direct performance of the operation o1120. In an implementation, the one or more receiving info bar code instructions i1120 when executed direct electronically receiving the directive information including substance identification associated with a bar code (e.g. an implementation of the receiver component s528 is configured to electronically engage with the processor component s102 to receive the directive information including substance identification as determined by the processor component through electronic reading of the bar code, etc.). Furthermore, the receiving info bar code electrical circuitry arrangement e1120 when activated will perform the operation electronically receiving the directive information including substance identification associated with a bar code. In an implementation, the receiving info bar code electrical circuitry arrangement e1120, when activated performs electronically receiving the directive information including substance identification associated with a bar code (e.g. an implementation of the receiver component s528 is configured to electronically engage with the processor component s102 to receive the directive information including substance identification as determined by the processor component through electronic reading of the bar code, etc.). In an implementation, the electronically receiving the directive information including substance identification associated with a bar code is carried out by electronically receiving the directive information including substance identification associated with a bar code (e.g. an implementation of the receiver component s528 is configured to electronically engage with the processor component s102 to receive the directive information including substance identification as determined by the processor component through electronic reading of the bar code, etc.).

Figure 29:
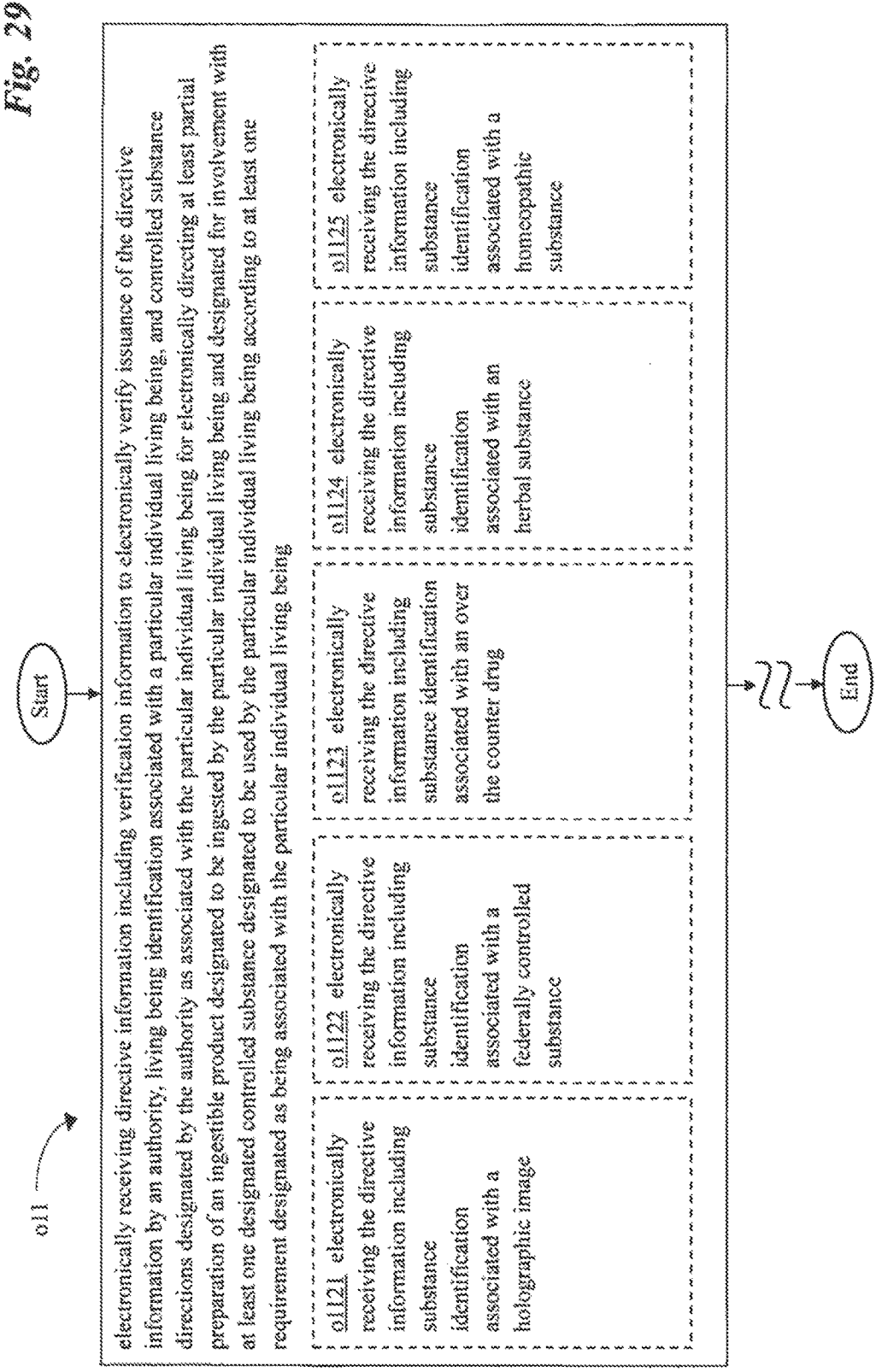
FIG. 29 is a high-level flowchart including exemplary implementations of operation O11 of FIG. 24.

In one or more implementations, as shown in FIG. 29, operation o11 includes an operation o1121 for electronically receiving the directive information including substance identification associated with a holographic image. An exemplary version of the non-transitory signal bearing medium n100 is depicted as bearing one or more receiving info holographic instructions i1121 that when executed will direct performance of the operation o1121. In an implementation, the one or more receiving info holographic instructions i1121 when executed direct electronically receiving the directive information including substance identification associated with a holographic image (e.g. an implementation of the receiver component s528 is configured to electronically engage with the processor component s102 to receive the directive information including substance identification as determined by the processor component through electronic reading of the holographic image, etc.). Furthermore, the receiving info holographic electrical circuitry arrangement e1121 when activated will perform the operation o1121. In an implementation, the receiving info holographic electrical circuitry arrangement e1121, when activated performs electronically receiving the directive information including substance identification associated with a holographic image (e.g. an implementation of the receiver component s528 is configured to electronically engage with the processor component s102 to receive the directive information including substance identification as determined by the processor component through electronic reading of the holographic image, etc.). In an implementation, the electronically receiving the directive information including substance identification associated with a holographic image is carried out by electronically receiving the directive information including substance identification associated with a holographic image (e.g. an implementation of the receiver component s528 is configured to electronically engage with the processor component s102 to receive the directive information including substance identification as determined by the processor component through electronic reading of the holographic image, etc.).

In one or more implementations, operation o11 includes an operation o1122 for electronically receiving the directive information including substance identification associated with a federally controlled substance. An exemplary version of the non-transitory signal bearing medium n100 is depicted as bearing one or more receiving info federally instructions i1122 that when executed will direct performance of the operation o1122. In an implementation, the one or more receiving info federally instructions i1122 when executed direct electronically receiving the directive information including substance identification associated with a federally controlled substance (e.g. an implementation of the receiver component s528 is configured to electronically engage with the processor component s102 to receive the directive information including substance identification as determined by the processor component to be associated with a federally controlled substance through a table lookup procedure, etc.). Furthermore, the receiving info federally electrical circuitry arrangement e1122 when activated will perform the operation o1122. In an implementation, the receiving info federally electrical circuitry arrangement e1122, when activated performs electronically receiving the directive information including substance identification associated with a federally controlled substance (e.g. an implementation of the receiver component s528 is configured to electronically engage with the processor component s102 to receive the directive information including substance identification as determined by the processor component to be associated with a federally controlled substance through a table lookup procedure, etc.). In an implementation, the electronically receiving the directive information including substance identification associated with a federally controlled substance is carried out by electronically receiving the directive information including substance identification associated with a federally controlled substance (e.g. an implementation of the receiver component s528 is configured to electronically engage with the processor component s102 to receive the directive information including substance identification as determined by the processor component to be associated with a federally controlled substance through a table lookup procedure, etc.).

In one or more implementations, operation o11 includes an operation o1123 for electronically receiving the directive information including substance identification associated with an over the counter drug. An exemplary version of the non-transitory signal bearing medium n100 is depicted as bearing one or more receiving info otc drug instructions i1123 that when executed will direct performance of the operation o1123. In an implementation, the one or more receiving info otc drug instructions i1123 when executed direct electronically receiving the directive information including substance identification associated with an over the counter drug (e.g. an implementation of the receiver component s528 is configured to electronically engage with the processor component s102 to receive the directive information including substance identification as determined by the processor component to be associated with the over the counter drug with a database query, etc.). Furthermore, the receiving info otc drug electrical circuitry arrangement e1123 when activated will perform the operation o1123. In an implementation, the receiving info otc drug electrical circuitry arrangement e1123, when activated performs electronically receiving the directive information including substance identification associated with an over the counter drug (e.g. an implementation of the receiver component s528 is configured to electronically engage with the processor component s102 to receive the directive information including substance identification as determined by the processor component to be associated with the over the counter drug with a database query, etc.). In an implementation, the electronically receiving the directive information including substance identification associated with an over the counter drug is carried out by electronically receiving the directive information including substance identification associated with an over the counter drug (e.g. an implementation of the receiver component s528 is configured to electronically engage with the processor component s102 to receive the directive information including substance identification as determined by the processor component to be associated with the over the counter drug with a database query, etc.).

In one or more implementations, operation o11 includes an operation o1124 for electronically receiving the directive information including substance identification associated with an herbal substance. An exemplary version of the non-transitory signal bearing medium n100 is depicted as bearing one or more receiving info herbal instructions i1124 that when executed will direct performance of the operation o1124. In an implementation, the one or more receiving info herbal instructions i1124 when executed direct electronically receiving the directive information including substance identification associated with an herbal substance (e.g. an implementation of the receiver component s528 is configured to electronically engage with the processor component s102 to receive the directive information including substance identification as determined by the processor component to be identifying an herbal substance, etc.). Furthermore, the receiving info herbal electrical circuitry arrangement e1124 when activated will perform the operation o1124. In an implementation, the receiving info herbal electrical circuitry arrangement e1124, when activated performs electronically receiving the directive information including substance identification associated with an herbal substance (e.g. an implementation of the receiver component s528 is configured to electronically engage with the processor component s102 to receive the directive information including substance identification as determined by the processor component to be identifying an herbal substance, etc.). In an implementation, the electronically receiving the directive information including substance identification associated with an herbal substance is carried out by electronically receiving the directive information including substance identification associated with an herbal substance (e.g. an implementation of the receiver component s528 is configured to electronically engage with the processor component s102 to receive the directive information including substance identification as determined by the processor component to be identifying an herbal substance, etc.).

In one or more implementations, operation o11 includes an operation o1125 for electronically receiving the directive information including substance identification associated with a homeopathic substance. An exemplary version of the non-transitory signal bearing medium n100 is depicted as bearing one or more receiving info homeopathic instructions i1125 that when executed will direct performance of the operation o1125. In an implementation, the one or more receiving info homeopathic instructions i1125 when executed direct electronically receiving the directive information including substance identification associated with a homeopathic substance (e.g. an implementation of the receiver component s528 is configured to electronically engage with the processor component s102 to receive the directive information including substance identification as determined by the processor component to be identifying a homeopathic substance, etc.). Furthermore, the receiving info homeopathic electrical circuitry arrangement e1125 when activated will perform the operation o1125. In an implementation, the receiving info homeopathic electrical circuitry arrangement e1125, when activated performs electronically receiving the directive information including substance identification associated with a homeopathic substance (e.g. an implementation of the receiver component s528 is configured to electronically engage with the processor component s102 to receive the directive information including substance identification as determined by the processor component to be identifying a homeopathic substance, etc.). In an implementation, the electronically receiving the directive information including substance identification associated with a homeopathic substance is carried out by electronically receiving the directive information including substance identification associated with a homeopathic substance (e.g. an implementation of the receiver component s528 is configured to electronically engage with the processor component s102 to receive the directive information including substance identification as determined by the processor component to be identifying a homeopathic substance, etc.).

Figure 30:
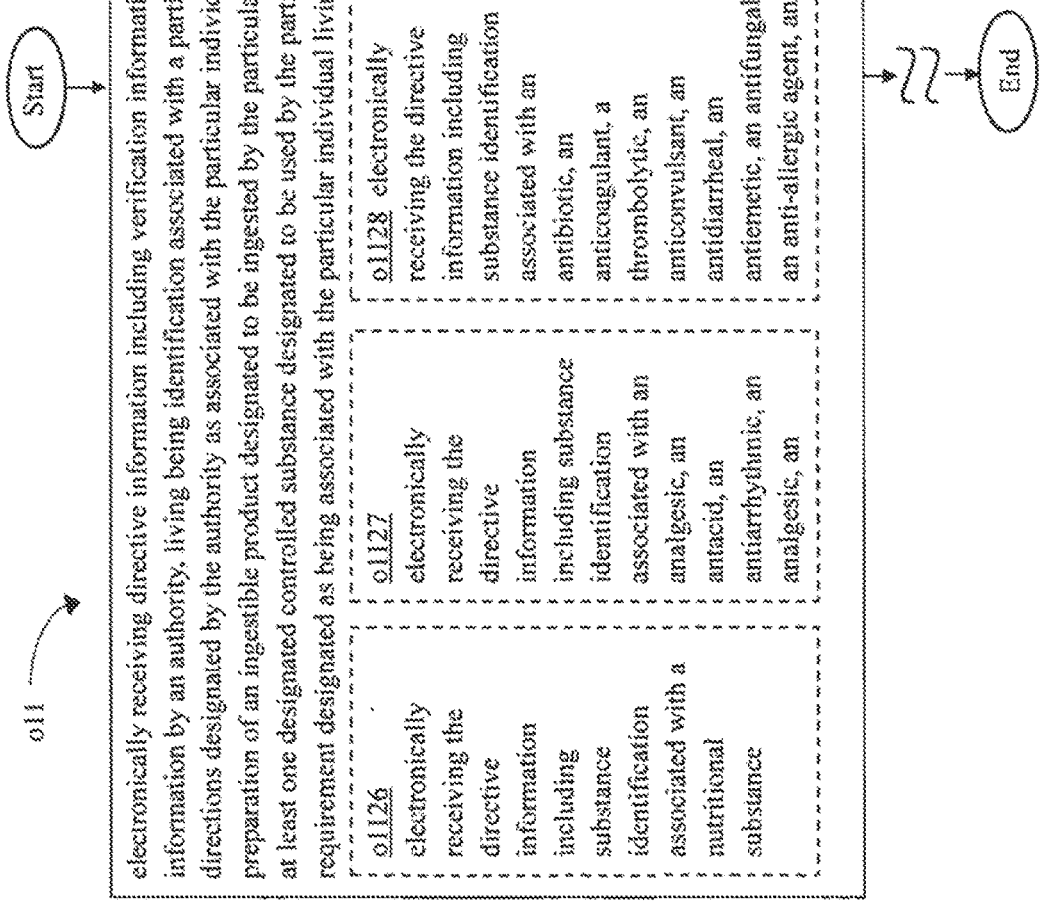
FIG. 30 is a high-level flowchart including exemplary implementations of operation O11 of FIG. 24.

In one or more implementations, as shown in FIG. 30, operation o11 includes an operation o1126 for electronically receiving the directive information including substance identification associated with a nutritional substance. An exemplary version of the non-transitory signal bearing medium n100 is depicted as bearing one or more receiving info nutritional instructions i1126 that when executed will direct performance of the operation o1126. In an implementation, the one or more receiving info nutritional instructions i1126 when executed direct electronically receiving the directive information including substance identification associated with a nutritional substance (e.g. an implementation of the receiver component s528 is configured to electronically engage with the processor component s102 to receive the directive information including substance identification as determined by the processor component to be identifying a nutritional substance, etc.). Furthermore, the receiving info nutritional electrical circuitry arrangement e1126 when activated will perform the operation o1126. In an implementation, the receiving info nutritional electrical circuitry arrangement e1126, when activated performs electronically receiving the directive information including substance identification associated with a nutritional substance (e.g. an implementation of the receiver component s528 is configured to electronically engage with the processor component s102 to receive the directive information including substance identification as determined by the processor component to be identifying a nutritional substance, etc.). In an implementation, the electronically receiving the directive information including substance identification associated with a nutritional substance is carried out by electronically receiving the directive information including substance identification associated with a nutritional substance (e.g. an implementation of the receiver component s528 is configured to electronically engage with the processor component s102 to receive the directive information including substance identification as determined by the processor component to be identifying a nutritional substance, etc.).

In one or more implementations, operation o11 includes an operation o1127 for electronically receiving the directive information including substance identification associated with an analgesic, an antacid, an antiarrhythmic, an analgesic, an antacid, an antiarrhythmic, or an antibacterial. An exemplary version of the non-transitory signal bearing medium n100 is depicted as bearing one or more receiving info first medications instructions i1127 that when executed will direct performance of the operation o1127. In an implementation, the one or more receiving info first medications instructions i1127 when executed direct electronically receiving the directive information including substance identification associated with an analgesic, an antacid, an antiarrhythmic, an analgesic, an antacid, an antiarrhythmic, or an antibacterial (e.g. an implementation of the receiver component s528 is configured to electronically engage with the processor component s102 to receive the directive information including substance identification as determined by the processor component to be identifying an analgesic, an antacid, an antiarrhythmic, an analgesic, an antacid, an antiarrhythmic, or an antibacterial, etc.)l. Furthermore, the receiving info first medications electrical circuitry arrangement e1127 when activated will perform the operation o1127. In an implementation, the receiving info first medications electrical circuitry arrangement e1127, when activated performs electronically receiving the directive information including substance identification associated with an analgesic, an antacid, an antiarrhythmic, an analgesic, an antacid, an antiarrhythmic, or an antibacterial (e.g. an implementation of the receiver component s528 is configured to electronically engage with the processor component s102 to receive the directive information including substance identification as determined by the processor component to be identifying an analgesic, an antacid, an antiarrhythmic, an analgesic, an antacid, an antiarrhythmic, or an antibacterial, etc.)l. In an implementation, the electronically receiving the directive information including substance identification associated with an analgesic, an antacid, an antiarrhythmic, an analgesic, an antacid, an antiarrhythmic, or an antibacterial is carried out by electronically receiving the directive information including substance identification associated with an analgesic, an antacid, an antiarrhythmic, an analgesic, an antacid, an antiarrhythmic, or an antibacterial (e.g. an implementation of the receiver component s528 is configured to electronically engage with the processor component s102 to receive the directive information including substance identification as determined by the processor component to be identifying an analgesic, an antacid, an antiarrhythmic, an analgesic, an antacid, an antiarrhythmic, or an antibacterial, etc.)l.

In one or more implementations, operation o11 includes an operation o1128 for electronically receiving the directive information including substance identification associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof. An exemplary version of the non-transitory signal bearing medium n100 is depicted as bearing one or more receiving info second medications instructions i1128 that when executed will direct performance of the operation o1128. In an implementation, the one or more receiving info second medications instructions i1128 when executed direct electronically receiving the directive information including substance identification associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof (e.g. an implementation of the receiver component s528 is configured to electronically engage with the processor component s102 to receive the directive information including substance identification as determined by the processor component to be identifying an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof, etc.). Furthermore, the receiving info second medications electrical circuitry arrangement e1128 when activated will perform the operation o1128. In an implementation, the receiving info second medications electrical circuitry arrangement e1128, when activated performs electronically receiving the directive information including substance identification associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof (e.g. an implementation of the receiver component s528 is configured to electronically engage with the processor component s102 to receive the directive information including substance identification as determined by the processor component to be identifying an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof, etc.). In an implementation, the electronically receiving the directive information including substance identification associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof is carried out by electronically receiving the directive information including substance identification associated with an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof (e.g. an implementation of the receiver component s528 is configured to electronically engage with the processor component s102 to receive the directive information including substance identification as determined by the processor component to be identifying an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, or a combination thereof, etc.).

In one or more implementations, operation o11 includes an operation o1129 for electronically receiving the directive information including substance identification associated with an antipyretic, an antiviral, an anti-ulcer agent, an antidyspeptic, an antacid, a beta-blocker, a bronchodilator, a cold treatment, or a corticosteroid. An exemplary version of the non-transitory signal bearing medium n100 is depicted as bearing one or more receiving info third medications instructions i1129 that when executed will direct performance of the operation o1129. In an implementation, the one or more receiving info third medications instructions i1129 when executed direct electronically receiving the directive information including substance identification associated with an antipyretic, an antiviral, an anti-ulcer agent, an antidyspeptic, an antacid, a beta-blocker, a bronchodilator, a cold treatment, or a corticosteroid (e.g. an implementation of the receiver component s528 is configured to electronically engage with the processor component s102 to receive the directive information including substance identification as determined by the processor component to be identifying an antipyretic, an antiviral, an anti-ulcer agent, an antidyspeptic, an antacid, a beta-blocker, a bronchodilator, a cold treatment, or a corticosteroid, etc.). Furthermore, the receiving info third medications electrical circuitry arrangement e1129 when activated will perform the operation o1129. In an implementation, the receiving info third medications electrical circuitry arrangement e1129, when activated performs electronically receiving the directive information including substance identification associated with an antipyretic, an antiviral, an anti-ulcer agent, an antidyspeptic, an antacid, a beta-blocker, a bronchodilator, a cold treatment, or a corticosteroid (e.g. an implementation of the receiver component s528 is configured to electronically engage with the processor component s102 to receive the directive information including substance identification as determined by the processor component to be identifying an antipyretic, an antiviral, an anti-ulcer agent, an antidyspeptic, an antacid, a beta-blocker, a bronchodilator, a cold treatment, or a corticosteroid, etc.). In an implementation, the electronically receiving the directive information including substance identification associated with an antipyretic, an antiviral, an anti-ulcer agent, an antidyspeptic, an antacid, a beta-blocker, a bronchodilator, a cold treatment, or a corticosteroid is carried out by electronically receiving the directive information including substance identification associated with an antipyretic, an antiviral, an anti-ulcer agent, an antidyspeptic, an antacid, a beta-blocker, a bronchodilator, a cold treatment, or a corticosteroid (e.g. an implementation of the receiver component s528 is configured to electronically engage with the processor component s102 to receive the directive information including substance identification as determined by the processor component to be identifying an antipyretic, an antiviral, an anti-ulcer agent, an antidyspeptic, an antacid, a beta-blocker, a bronchodilator, a cold treatment, or a corticosteroid, etc.).

In one or more implementations, operation o11 includes an operation o1130 for electronically receiving the directive information including substance identification associated with a cough suppressant, an antitussive, a cytotoxic agent, a decongestant, a diuretic, or an expectorant. An exemplary version of the non-transitory signal bearing medium n100 is depicted as bearing one or more receiving info fourth medications instructions i1130 that when executed will direct performance of the operation o1130. In an implementation, the one or more receiving info fourth medications instructions i1130 when executed direct electronically receiving the directive information including substance identification associated with a cough suppressant, an antitussive, a cytotoxic agent, a decongestant, a diuretic, or an expectorant (e.g. an implementation of the receiver component s528 is configured to electronically engage with the processor component s102 to receive the directive information including substance identification as determined by the processor component to be identifying a cough suppressant, an antitussive, a cytotoxic agent, a decongestant, a diuretic, or an expectorant, etc.). Furthermore, the receiving info fourth medications electrical circuitry arrangement e1130 when activated will perform the operation o1130. In an implementation, the receiving info fourth medications electrical circuitry arrangement e1130, when activated performs electronically receiving the directive information including substance identification associated with a cough suppressant, an antitussive, a cytotoxic agent, a decongestant, a diuretic, or an expectorant (e.g. an implementation of the receiver component s528 is configured to electronically engage with the processor component s102 to receive the directive information including substance identification as determined by the processor component to be identifying a cough suppressant, an antitussive, a cytotoxic agent, a decongestant, a diuretic, or an expectorant, etc.). In an implementation, the electronically receiving the directive information including substance identification associated with a cough suppressant, an antitussive, a cytotoxic agent, a decongestant, a diuretic, or an expectorant is carried out by electronically receiving the directive information including substance identification associated with a cough suppressant, an antitussive, a cytotoxic agent, a decongestant, a diuretic, or an expectorant (e.g. an implementation of the receiver component s528 is configured to electronically engage with the processor component s102 to receive the directive information including substance identification as determined by the processor component to be identifying a cough suppressant, an antitussive, a cytotoxic agent, a decongestant, a diuretic, or an expectorant, etc.).

Figure 31:
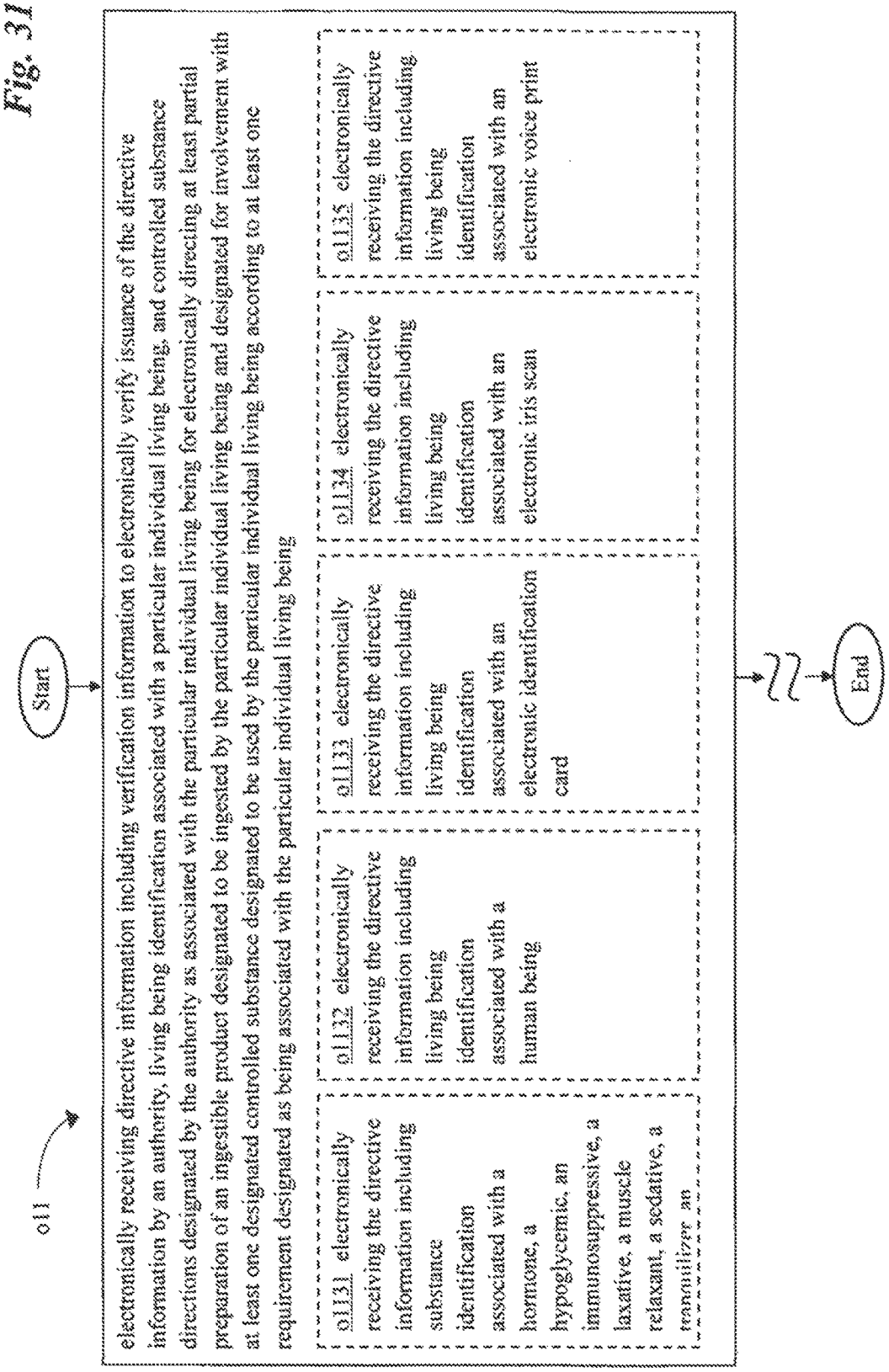
FIG. 31 is a high-level flowchart including exemplary implementations of operation O11 of FIG. 24.

In one or more implementations, as shown in FIG. 31, operation o11 includes an operation o1131 for electronically receiving the directive information including substance identification associated with a hormone, a hypoglycemic, an immunosuppressive, a laxative, a muscle relaxant, a sedative, a tranquilizer, an appetite modulator, a vitamin, or a combination thereof. An exemplary version of the non-transitory signal bearing medium n100 is depicted as bearing one or more receiving fifth medications instructions i1131 that when executed will direct performance of the operation o1131. In an implementation, the one or more receiving fifth medications instructions i1131 when executed direct electronically receiving the directive information including substance identification associated with a hormone, a hypoglycemic, an immunosuppressive, a laxative, a muscle relaxant, a sedative, a tranquilizer, an appetite modulator, a vitamin, or a combination thereof (e.g. an implementation of the receiver component s528 is configured to electronically engage with the processor component s102 to receive the directive information including substance identification as determined by the processor component to be identifying a hormone, a hypoglycemic, an immunosuppressive, a laxative, a muscle relaxant, a sedative, a tranquilizer, an appetite modulator, a vitamin, or a combination thereof, etc.). Furthermore, the receiving fifth medications electrical circuitry arrangement e1131 when activated will perform the operation o1131. In an implementation, the receiving fifth medications electrical circuitry arrangement e1131, when activated performs electronically receiving the directive information including substance identification associated with a hormone, a hypoglycemic, an immunosuppressive, a laxative, a muscle relaxant, a sedative, a tranquilizer, an appetite modulator, a vitamin, or a combination thereof (e.g. an implementation of the receiver component s528 is configured to electronically engage with the processor component s102 to receive the directive information including substance identification as determined by the processor component to be identifying a hormone, a hypoglycemic, an immunosuppressive, a laxative, a muscle relaxant, a sedative, a tranquilizer, an appetite modulator, a vitamin, or a combination thereof, etc.). In an implementation, the electronically receiving the directive information including substance identification associated with a hormone, a hypoglycemic, an immunosuppressive, a laxative, a muscle relaxant, a sedative, a tranquilizer, an appetite modulator, a vitamin, or a combination thereof is carried out by electronically receiving the directive information including substance identification associated with a hormone, a hypoglycemic, an immunosuppressive, a laxative, a muscle relaxant, a sedative, a tranquilizer, an appetite modulator, a vitamin, or a combination thereof (e.g. an implementation of the receiver component s528 is configured to electronically engage with the processor component s102 to receive the directive information including substance identification as determined by the processor component to be identifying a hormone, a hypoglycemic, an immunosuppressive, a laxative, a muscle relaxant, a sedative, a tranquilizer, an appetite modulator, a vitamin, or a combination thereof, etc.).

In one or more implementations, operation o11 includes an operation o1132 for electronically receiving the directive information including living being identification associated with a human being. An exemplary version of the non-transitory signal bearing medium n100 is depicted as bearing one or more receiving info human instructions i1132 that when executed will direct performance of the operation o1132. In an implementation, the one or more receiving info human instructions i1132 when executed direct electronically receiving the directive information including living being identification associated with a human being (e.g. an implementation of the receiver component s528 is configured to electronically engage with the processor component s102 to receive the directive information including living being identification as determined by the processor component to be identifying a human being, etc.). Furthermore, the receiving info human electrical circuitry arrangement e1132 when activated will perform the operation o1132. In an implementation, the receiving info human electrical circuitry arrangement e1132, when activated performs electronically receiving the directive information including living being identification associated with a human being (e.g. an implementation of the receiver component s528 is configured to electronically engage with the processor component s102 to receive the directive information including living being identification as determined by the processor component to be identifying a human being, etc.). In an implementation, the electronically receiving the directive information including living being identification associated with a human being is carried out by electronically receiving the directive information including living being identification associated with a human being (e.g. an implementation of the receiver component s528 is configured to electronically engage with the processor component s102 to receive the directive information including living being identification as determined by the processor component to be identifying a human being, etc.).

In one or more implementations, operation o11 includes an operation o1133 for electronically receiving the directive information including living being identification associated with an electronic identification card. An exemplary version of the non-transitory signal bearing medium n100 is depicted as bearing one or more receiving info ID card instructions i1133 that when executed will direct performance of the operation o1133. In an implementation, the one or more receiving info ID card instructions i1133 when executed direct electronically receiving the directive information including living being identification associated with an electronic identification card (e.g. an implementation of the receiver component s528 is configured to electronically engage with the processor component s102 to receive the directive information including living being identification as determined by the processor component to be identifying a living being through the electronic identification card, etc.). Furthermore, the receiving info ID card electrical circuitry arrangement e1133 when activated will perform the operation o1133. In an implementation, the receiving info ID card electrical circuitry arrangement e1133, when activated performs electronically receiving the directive information including living being identification associated with an electronic identification card (e.g. an implementation of the receiver component s528 is configured to electronically engage with the processor component s102 to receive the directive information including living being identification as determined by the processor component to be identifying a living being through the electronic identification card, etc.). In an implementation, the electronically receiving the directive information including living being identification associated with an electronic identification card is carried out by electronically receiving the directive information including living being identification associated with an electronic identification card (e.g. an implementation of the receiver component s528 is configured to electronically engage with the processor component s102 to receive the directive information including living being identification as determined by the processor component to be identifying a living being through the electronic identification card, etc.).

In one or more implementations, operation o11 includes an operation o1134 for electronically receiving the directive information including living being identification associated with an electronic iris scan. An exemplary version of the non-transitory signal bearing medium n100 is depicted as bearing one or more receiving info iris scan instructions i1134 that when executed will direct performance of the operation o1134. In an implementation, the one or more receiving info iris scan instructions i1134 when executed direct electronically receiving the directive information including living being identification associated with an electronic iris scan (e.g. an implementation of the receiver component s528 is configured to electronically engage with the processor component s102 to receive the directive information including living being identification as determined by the processor component to be identifying the living being through the electronic iris scan, etc.). Furthermore, the receiving info iris scan electrical circuitry arrangement e1134 when activated will perform the operation o1134. In an implementation, the receiving info iris scan electrical circuitry arrangement e1134, when activated performs electronically receiving the directive information including living being identification associated with an electronic iris scan (e.g. an implementation of the receiver component s528 is configured to electronically engage with the processor component s102 to receive the directive information including living being identification as determined by the processor component to be identifying the living being through the electronic iris scan, etc.). In an implementation, the electronically receiving the directive information including living being identification associated with an electronic iris scan is carried out by electronically receiving the directive information including living being identification associated with an electronic iris scan (e.g. an implementation of the receiver component s528 is configured to electronically engage with the processor component s102 to receive the directive information including living being identification as determined by the processor component to be identifying the living being through the electronic iris scan, etc.).

In one or more implementations, operation o11 includes an operation o1135 for electronically receiving the directive information including living being identification associated with an electronic voice print. An exemplary version of the non-transitory signal bearing medium n100 is depicted as bearing one or more receiving info voice instructions i1135 that when executed will direct performance of the operation o1135. In an implementation, the one or more receiving info voice instructions i1135 when executed direct electronically receiving the directive information including living being identification associated with an electronic voice print (e.g. an implementation of the receiver component s528 is configured to electronically engage with the processor component s102 to receive the directive information including living being identification as determined by the processor component to be identifying the living being through the electronic voice print, etc.). Furthermore, the receiving info voice electrical circuitry arrangement e1135 when activated will perform the operation o1135. In an implementation, the receiving info voice electrical circuitry arrangement e1135, when activated performs electronically receiving the directive information including living being identification associated with an electronic voice print (e.g. an implementation of the receiver component s528 is configured to electronically engage with the processor component s102 to receive the directive information including living being identification as determined by the processor component to be identifying the living being through the electronic voice print, etc.). In an implementation, the electronically receiving the directive information including living being identification associated with an electronic voice print is carried out by electronically receiving the directive information including living being identification associated with an electronic voice print (e.g. an implementation of the receiver component s528 is configured to electronically engage with the processor component s102 to receive the directive information including living being identification as determined by the processor component to be identifying the living being through the electronic voice print, etc.).

Figure 32:
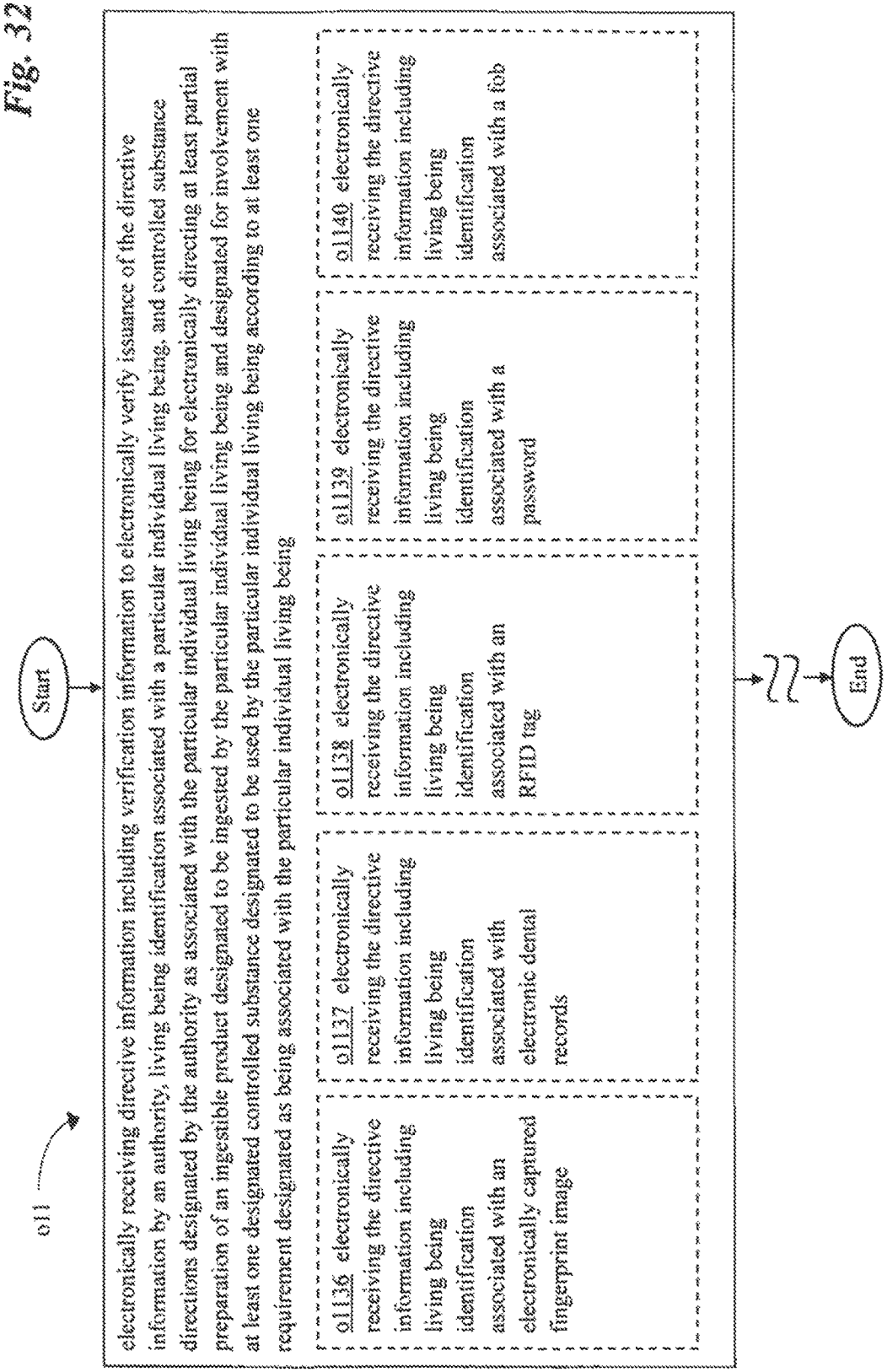
FIG. 32 is a high-level flowchart including exemplary implementations of operation O11 of FIG. 24.

In one or more implementations, as shown in FIG. 32, operation o11 includes an operation o1136 for electronically receiving the directive information including living being identification associated with an electronically captured fingerprint image. An exemplary version of the non-transitory signal bearing medium n100 is depicted as bearing one or more receiving info fingerprint instructions i1136 that when executed will direct performance of the operation o1136. In an implementation, the one or more receiving info fingerprint instructions i1136 when executed direct electronically receiving the directive information including living being identification associated with an electronically captured fingerprint image (e.g. an implementation of the receiver component s528 is configured to electronically engage with the processor component s102 to receive the directive information including living being identification as determined by the processor component to be identifying the living being through the electronically captured fingerprint image, etc.). Furthermore, the receiving info fingerprint electrical circuitry arrangement e1136 when activated will perform the operation o1136. In an implementation, the receiving info fingerprint electrical circuitry arrangement e1136, when activated performs electronically receiving the directive information including living being identification associated with an electronically captured fingerprint image (e.g. an implementation of the receiver component s528 is configured to electronically engage with the processor component s102 to receive the directive information including living being identification as determined by the processor component to be identifying the living being through the electronically captured fingerprint image, etc.). In an implementation, the electronically receiving the directive information including living being identification associated with an electronically captured fingerprint image is carried out by electronically receiving the directive information including living being identification associated with an electronically captured fingerprint image (e.g. an implementation of the receiver component s528 is configured to electronically engage with the processor component s102 to receive the directive information including living being identification as determined by the processor component to be identifying the living being through the electronically captured fingerprint image, etc.).

In one or more implementations, operation o11 includes an operation o1137 for electronically receiving the directive information including living being identification associated with electronic dental records. An exemplary version of the non-transitory signal bearing medium n100 is depicted as bearing one or more receiving info dental instructions i1137 that when executed will direct performance of the operation o1137. In an implementation, the one or more receiving info dental instructions i1137 when executed direct electronically receiving the directive information including living being identification associated with electronic dental records (e.g. an implementation of the receiver component s528 is configured to electronically engage with the processor component s102 to receive the directive information including living being identification as determined by the processor component to be identifying the living being through the electronic dental records, etc.). Furthermore, the receiving info dental electrical circuitry arrangement e1137 when activated will perform the operation o1137. In an implementation, the receiving info dental electrical circuitry arrangement e1137, when activated performs electronically receiving the directive information including living being identification associated with electronic dental records (e.g. an implementation of the receiver component s528 is configured to electronically engage with the processor component s102 to receive the directive information including living being identification as determined by the processor component to be identifying the living being through the electronic dental records, etc.). In an implementation, the electronically receiving the directive information including living being identification associated with electronic dental records is carried out by electronically receiving the directive information including living being identification associated with electronic dental records (e.g. an implementation of the receiver component s528 is configured to electronically engage with the processor component s102 to receive the directive information including living being identification as determined by the processor component to be identifying the living being through the electronic dental records, etc.).

In one or more implementations, operation o11 includes an operation o1138 for electronically receiving the directive information including living being identification associated with an RFID tag. An exemplary version of the non-transitory signal bearing medium n100 is depicted as bearing one or more receiving info RFID instructions i1138 that when executed will direct performance of the operation o1138. In an implementation, the one or more receiving info RFID instructions i1138 when executed direct electronically receiving the directive information including living being identification associated with an RFID tag (e.g. an implementation of the receiver component s528 is configured to electronically engage with the processor component s102 to receive the directive information including living being identification as determined by the processor component to be identifying the living being through the RFID tag, etc.). Furthermore, the receiving info RFID electrical circuitry arrangement e1138 when activated will perform the operation o1138. In an implementation, the receiving info RFID electrical circuitry arrangement e1138, when activated performs electronically receiving the directive information including living being identification associated with an RFID tag (e.g. an implementation of the receiver component s528 is configured to electronically engage with the processor component s102 to receive the directive information including living being identification as determined by the processor component to be identifying the living being through the RFID tag, etc.). In an implementation, the electronically receiving the directive information including living being identification associated with an RFID tag is carried out by electronically receiving the directive information including living being identification associated with an RFID tag (e.g. an implementation of the receiver component s528 is configured to electronically engage with the processor component s102 to receive the directive information including living being identification as determined by the processor component to be identifying the living being through the RFID tag, etc.).

In one or more implementations, operation o11 includes an operation o1139 for electronically receiving the directive information including living being identification associated with a password. An exemplary version of the non-transitory signal bearing medium n100 is depicted as bearing one or more receiving info password instructions i1139 that when executed will direct performance of the operation o1139. In an implementation, the one or more receiving info password instructions i1139 when executed direct electronically receiving the directive information including living being identification associated with a password (e.g. an implementation of the receiver component s528 is configured to electronically engage with the processor component s102 to receive the directive information including living being identification as determined by the processor component to be identifying the living being through the password, etc.). Furthermore, the receiving info password electrical circuitry arrangement e1139 when activated will perform the operation o1139. In an implementation, the receiving info password electrical circuitry arrangement e1139, when activated performs electronically receiving the directive information including living being identification associated with a password (e.g. an implementation of the receiver component s528 is configured to electronically engage with the processor component s102 to receive the directive information including living being identification as determined by the processor component to be identifying the living being through the password, etc.). In an implementation, the electronically receiving the directive information including living being identification associated with a password is carried out by electronically receiving the directive information including living being identification associated with a password (e.g. an implementation of the receiver component s528 is configured to electronically engage with the processor component s102 to receive the directive information including living being identification as determined by the processor component to be identifying the living being through the password, etc.).

In one or more implementations, operation o11 includes an operation o1140 for electronically receiving the directive information including living being identification associated with a fob. An exemplary version of the non-transitory signal bearing medium n100 is depicted as bearing one or more receiving info fob instructions i1140 that when executed will direct performance of the operation o1140. In an implementation, the one or more receiving info fob instructions i1140 when executed direct electronically receiving the directive information including living being identification associated with a fob (e.g. an implementation of the receiver component s528 is configured to electronically engage with the processor component s102 to receive the directive information including living being identification as determined by the processor component to be identifying the living being through electronic data contained on the fob, etc.). Furthermore, the receiving info fob electrical circuitry arrangement e1140 when activated will perform the operation o1140. In an implementation, the receiving info fob electrical circuitry arrangement e1140, when activated performs electronically receiving the directive information including living being identification associated with a fob (e.g. an implementation of the receiver component s528 is configured to electronically engage with the processor component s102 to receive the directive information including living being identification as determined by the processor component to be identifying the living being through electronic data contained on the fob, etc.). In an implementation, the electronically receiving the directive information including living being identification associated with a fob is carried out by electronically receiving the directive information including living being identification associated with a fob (e.g. an implementation of the receiver component s528 is configured to electronically engage with the processor component s102 to receive the directive information including living being identification as determined by the processor component to be identifying the living being through electronic data contained on the fob, etc.).

Figure 33:
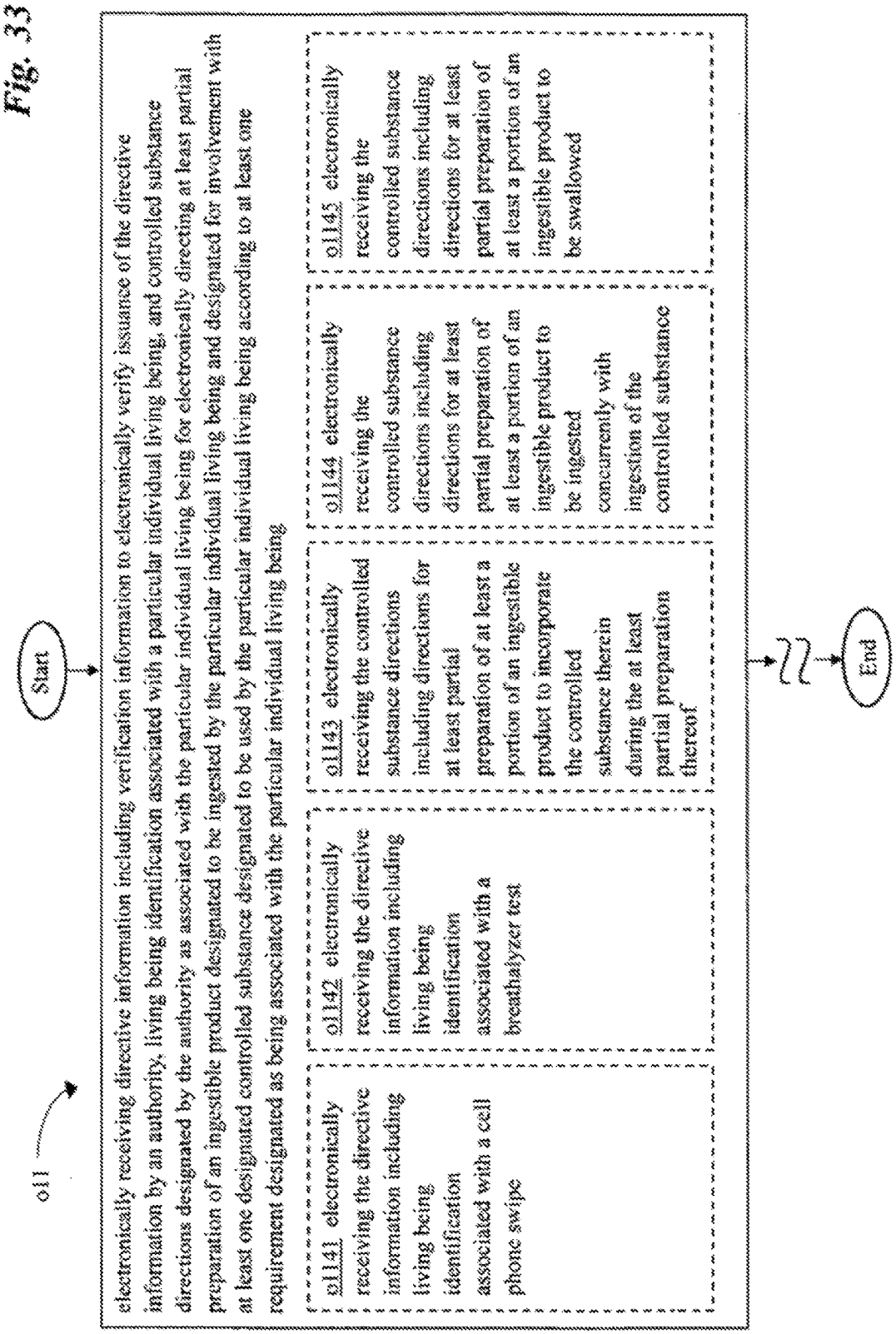
FIG. 33 is a high-level flowchart including exemplary implementations of operation O11 of FIG. 24.

In one or more implementations, as shown in FIG. 33, operation o11 includes an operation o1141 for electronically receiving the directive information including living being identification associated with a cell phone swipe. An exemplary version of the non-transitory signal bearing medium n100 is depicted as bearing one or more receiving info cell phone instructions i1141 that when executed will direct performance of the operation o1141. In an implementation, the one or more receiving info cell phone instructions i1141 when executed direct electronically receiving the directive information including living being identification associated with a cell phone swipe (e.g. an implementation of the receiver component s528 is configured to electronically engage with the processor component s102 to receive the directive information including living being identification as determined by the processor component to be identifying the living being through passing the cell phone in close proximity to the cell phone, etc.). Furthermore, the receiving info cell phone electrical circuitry arrangement e1141 when activated will perform the operation o1141. In an implementation, the receiving info cell phone electrical circuitry arrangement e1141, when activated performs electronically receiving the directive information including living being identification associated with a cell phone swipe (e.g. an implementation of the receiver component s528 is configured to electronically engage with the processor component s102 to receive the directive information including living being identification as determined by the processor component to be identifying the living being through passing the cell phone in close proximity to the cell phone, etc.). In an implementation, the electronically receiving the directive information including living being identification associated with a cell phone swipe is carried out by electronically receiving the directive information including living being identification associated with a cell phone swipe (e.g. an implementation of the receiver component s528 is configured to electronically engage with the processor component s102 to receive the directive information including living being identification as determined by the processor component to be identifying the living being through passing the cell phone in close proximity to the cell phone, etc.).

In one or more implementations, operation o11 includes an operation o1142 for electronically receiving the directive information including living being identification associated with a breathalyzer test. An exemplary version of the non-transitory signal bearing medium n100 is depicted as bearing one or more receiving info breathalyzer instructions i1142 that when executed will direct performance of the operation o1142. In an implementation, the one or more receiving info breathalyzer instructions i1142 when executed direct electronically receiving the directive information including living being identification associated with a breathalyzer test (e.g. an implementation of the receiver component s528 is configured to electronically engage with the processor component s102 to receive the directive information including living being identification as determined by the processor component to be identifying the living being through the breathalyzer test of the living being, etc.). Furthermore, the receiving info breathalyzer electrical circuitry arrangement e1142 when activated will perform the operation o1142. In an implementation, the receiving info breathalyzer electrical circuitry arrangement e1142, when activated performs electronically receiving the directive information including living being identification associated with a breathalyzer test (e.g. an implementation of the receiver component s528 is configured to electronically engage with the processor component s102 to receive the directive information including living being identification as determined by the processor component to be identifying the living being through the breathalyzer test of the living being, etc.). In an implementation, the electronically receiving the directive information including living being identification associated with a breathalyzer test is carried out by electronically receiving the directive information including living being identification associated with a breathalyzer test (e.g. an implementation of the receiver component s528 is configured to electronically engage with the processor component s102 to receive the directive information including living being identification as determined by the processor component to be identifying the living being through the breathalyzer test of the living being, etc.).

In one or more implementations, operation o11 includes an operation o1143 for electronically receiving the controlled substance directions including directions for at least partial preparation of at least a portion of an ingestible product to incorporate the controlled substance therein during the at least partial preparation thereof. An exemplary version of the non-transitory signal bearing medium n100 is depicted as bearing one or more receiving info incorporate instructions i1143 that when executed will direct performance of the operation o1143. In an implementation, the one or more receiving info incorporate instructions i1143 when executed direct electronically receiving the controlled substance directions including directions for at least partial preparation of at least a portion of an ingestible product to incorporate the controlled substance therein during the at least partial preparation thereof (e.g. an implementation of the receiver component s528 is configured to electronically receive the controlled substance directions and engage with the processor component s102 to direct the material processing subsystem s700 to at least partially prepare a portion of the ingestible product such as a sandwich to include the controlled substance as an amino acid incorporated into the sandwich, etc.). Furthermore, the receiving info incorporate electrical circuitry arrangement e1143 when activated will perform the operation o1143. In an implementation, the receiving info incorporate electrical circuitry arrangement e1143, when activated performs electronically receiving the controlled substance directions including directions for at least partial preparation of at least a portion of an ingestible product to incorporate the controlled substance therein during the at least partial preparation thereof (e.g. an implementation of the receiver component s528 is configured to electronically receive the controlled substance directions and engage with the processor component s102 to direct the material processing subsystem s700 to at least partially prepare a portion of the ingestible product such as a sandwich to include the controlled substance as an amino acid incorporated into the sandwich, etc.). In an implementation, the electronically receiving the controlled substance directions including directions for at least partial preparation of at least a portion of an ingestible product to incorporate the controlled substance therein during the at least partial preparation thereof is carried out by electronically receiving the controlled substance directions including directions for at least partial preparation of at least a portion of an ingestible product to incorporate the controlled substance therein during the at least partial preparation thereof (e.g. an implementation of the receiver component s528 is configured to electronically receive the controlled substance directions and engage with the processor component s102 to direct the material processing subsystem s700 to at least partially prepare a portion of the ingestible product such as a sandwich to include the controlled substance as an amino acid incorporated into the sandwich, etc.).

In one or more implementations, operation o11 includes an operation o1144 for electronically receiving the controlled substance directions including directions for at least partial preparation of at least a portion of an ingestible product to be ingested concurrently with ingestion of the controlled substance. An exemplary version of the non-transitory signal bearing medium n100 is depicted as bearing one or more receiving info concurrent instructions i1144 that when executed will direct performance of the operation o1144. In an implementation, the one or more receiving info concurrent instructions i1144 when executed direct electronically receiving the controlled substance directions including directions for at least partial preparation of at least a portion of an ingestible product to be ingested concurrently with ingestion of the controlled substance (e.g. an implementation of the receiver component s528 is configured to electronically receive the controlled substance directions and engage with the processor component s102 to direct the material processing subsystem s700 to at least partially prepare a portion of the ingestible product such as a smoothie to contain an activator that is designed to interact with a controlled substance, such as a pharmaceutical agent that is encapsulated in pill form to be ingested by a living being, such as a boy, at the same time that the smoothie is being ingested by the boy, etc.). Furthermore, the receiving info concurrent electrical circuitry arrangement e1144 when activated will perform the operation o1144. In an implementation, the receiving info concurrent electrical circuitry arrangement e1144, when activated performs electronically receiving the controlled substance directions including directions for at least partial preparation of at least a portion of an ingestible product to be ingested concurrently with ingestion of the controlled substance (e.g. an implementation of the receiver component s528 is configured to electronically receive the controlled substance directions and engage with the processor component s102 to direct the material processing subsystem s700 to at least partially prepare a portion of the ingestible product such as a smoothie to contain an activator that is designed to interact with a controlled substance, such as a pharmaceutical agent that is encapsulated in pill form to be ingested by a living being, such as a boy, at the same time that the smoothie is being ingested by the boy, etc.). In an implementation, the electronically receiving the controlled substance directions including directions for at least partial preparation of at least a portion of an ingestible product to be ingested concurrently with ingestion of the controlled substance is carried out by electronically receiving the controlled substance directions including directions for at least partial preparation of at least a portion of an ingestible product to be ingested concurrently with ingestion of the controlled substance (e.g. an implementation of the receiver component s528 is configured to electronically receive the controlled substance directions and engage with the processor component s102 to direct the material processing subsystem s700 to at least partially prepare a portion of the ingestible product such as a smoothie to contain an activator that is designed to interact with a controlled substance, such as a pharmaceutical agent that is encapsulated in pill form to be ingested by a living being, such as a boy, at the same time that the smoothie is being ingested by the boy, etc.).

In one or more implementations, operation o11 includes an operation o1145 for electronically receiving the controlled substance directions including directions for at least partial preparation of at least a portion of an ingestible product to be swallowed. An exemplary version of the non-transitory signal bearing medium n100 is depicted as bearing one or more receiving info swallow instructions i1145 that when executed will direct performance of the operation o1145. In an implementation, the one or more receiving info swallow instructions i1145 when executed direct electronically receiving the controlled substance directions including directions for at least partial preparation of at least a portion of an ingestible product to be swallowed (e.g., an implementation of the receiver component s528 is configured to electronically receive the controlled substance directions and engage with the processor component s102 to direct the material processing subsystem s700 to at least partially prepare a portion of the ingestible product to be swallowed such as a snack bar, etc.). Furthermore, the receiving info swallow electrical circuitry arrangement e1145 when activated will perform the operation o1145. In an implementation, the receiving info swallow electrical circuitry arrangement e1145, when activated performs electronically receiving the controlled substance directions including directions for at least partial preparation of at least a portion of an ingestible product to be swallowed (e.g., an implementation of the receiver component s528 is configured to electronically receive the controlled substance directions and engage with the processor component s102 to direct the material processing subsystem s700 to at least partially prepare a portion of the ingestible product to be swallowed such as a snack bar, etc.). In an implementation, the electronically receiving the controlled substance directions including directions for at least partial preparation of at least a portion of an ingestible product to be swallowed is carried out by electronically receiving the controlled substance directions including directions for at least partial preparation of at least a portion of an ingestible product to be swallowed (e.g., an implementation of the receiver component s528 is configured to electronically receive the controlled substance directions and engage with the processor component s102 to direct the material processing subsystem s700 to at least partially prepare a portion of the ingestible product to be swallowed such as a snack bar, etc.).

Figure 34:
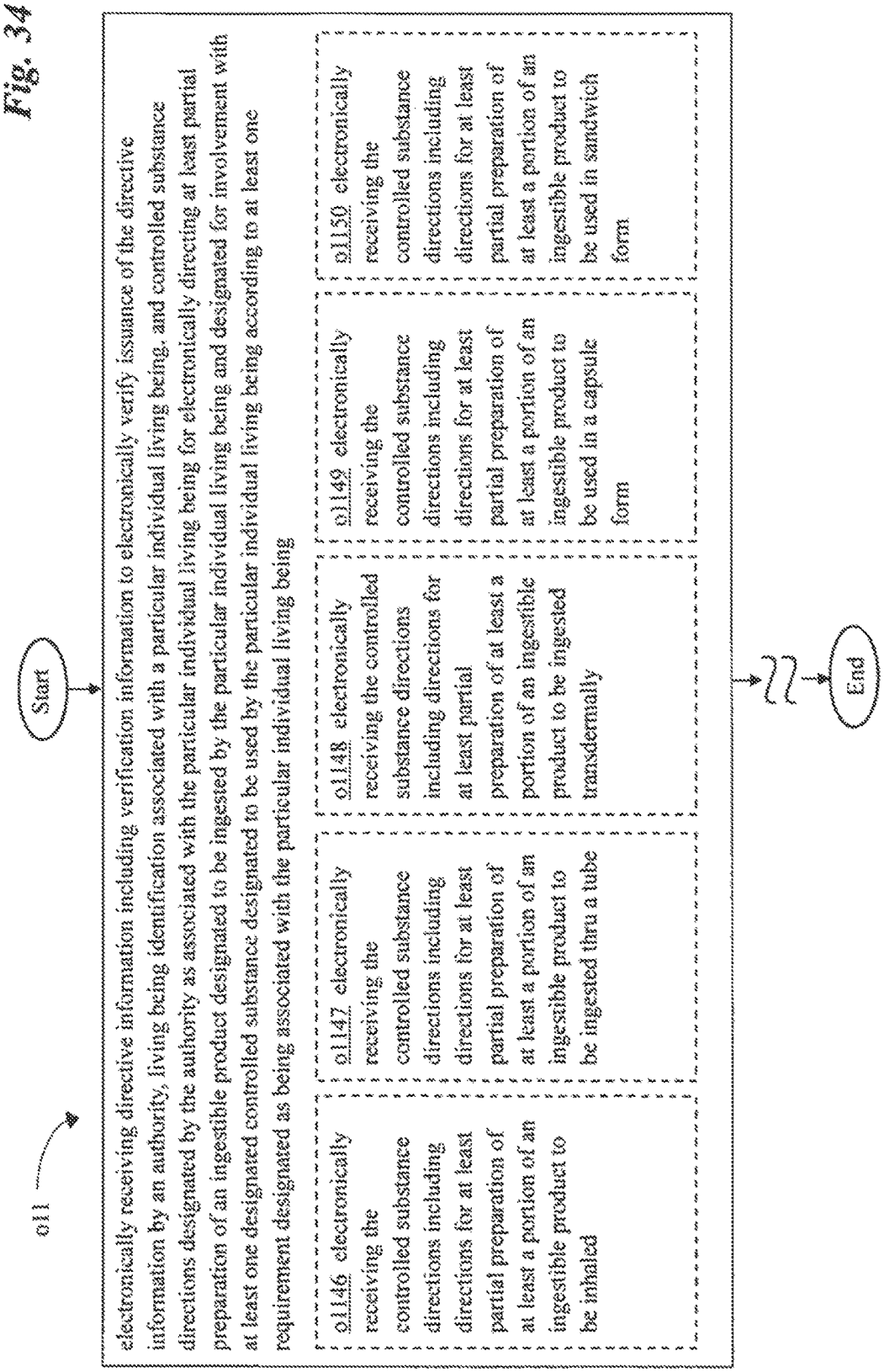
FIG. 34 is a high-level flowchart including exemplary implementations of operation O11 of FIG. 24.

In one or more implementations, as shown in FIG. 34, operation o11 includes an operation o1146 for electronically receiving the controlled substance directions including directions for at least partial preparation of at least a portion of an ingestible product to be inhaled. An exemplary version of the non-transitory signal bearing medium n100 is depicted as bearing one or more receiving info inhaled instructions i1146 that when executed will direct performance of the operation o1146. In an implementation, the one or more receiving info inhaled instructions i1146 when executed direct electronically receiving the controlled substance directions including directions for at least partial preparation of at least a portion of an ingestible product to be inhaled (e.g. an implementation of the receiver component s528 is configured to electronically receive the controlled substance directions and engage with the processor component s102 to direct the material processing subsystem s700 to at least partially prepare a portion of the ingestible product to be inhaled such as an ingestible dispensed through a nebulizer, etc. ). Furthermore, the receiving info inhaled electrical circuitry arrangement e 1146 when activated will perform the operation o1146. In an implementation, the receiving info inhaled electrical circuitry arrangement el146, when activated performs electronically receiving the controlled substance directions including directions for at least partial preparation of at least a portion of an ingestible product to be inhaled (e.g. an implementation of the receiver component s528 is configured to electronically receive the controlled substance directions and engage with the processor component s102 to direct the material processing subsystem s700 to at least partially prepare a portion of the ingestible product to be inhaled such as an ingestible dispensed through a nebulizer, etc.). In an implementation, the electronically receiving the controlled substance directions including directions for at least partial preparation of at least a portion of an ingestible product to be inhaled is carried out by electronically receiving the controlled substance directions including directions for at least partial preparation of at least a portion of an ingestible product to be inhaled (e.g. an implementation of the receiver component s528 is configured to electronically receive the controlled substance directions and engage with the processor component s102 to direct the material processing subsystem s700 to at least partially prepare a portion of the ingestible product to be inhaled such as an ingestible dispensed through a nebulizer, etc.).

In one or more implementations, operation o11 includes an operation o1147 for electronically receiving the controlled substance directions including directions for at least partial preparation of at least a portion of an ingestible product to be ingested thru a tube. An exemplary version of the non-transitory signal bearing medium n100 is depicted as bearing one or more receiving info tube instructions i1147 that when executed will direct performance of the operation o1147. In an implementation, the one or more receiving info tube instructions i1147 when executed direct electronically receiving the controlled substance directions including directions for at least partial preparation of at least a portion of an ingestible product to be ingested thru a tube (e.g., an implementation of the receiver component s528 is configured to electronically receive the controlled substance directions and engage with the processor component s102 to direct the material processing subsystem s700 to at least partially prepare a portion of the ingestible product to be ingested through a tube such as a liquid meal replacement, etc.). Furthermore, the receiving info tube electrical circuitry arrangement e1147 when activated will perform the operation o1147. In an implementation, the receiving info tube electrical circuitry arrangement e1147, when activated performs electronically receiving the controlled substance directions including directions for at least partial preparation of at least a portion of an ingestible product to be ingested thru a tube (e.g., an implementation of the receiver component s528 is configured to electronically receive the controlled substance directions and engage with the processor component s102 to direct the material processing subsystem s700 to at least partially prepare a portion of the ingestible product to be ingested through a tube such as a liquid meal replacement, etc.). In an implementation, the electronically receiving the controlled substance directions including directions for at least partial preparation of at least a portion of an ingestible product to be ingested thru a tube is carried out by electronically receiving the controlled substance directions including directions for at least partial preparation of at least a portion of an ingestible product to be ingested thru a tube (e.g., an implementation of the receiver component s528 is configured to electronically receive the controlled substance directions and engage with the processor component s102 to direct the material processing subsystem s700 to at least partially prepare a portion of the ingestible product to be ingested through a tube such as a liquid meal replacement, etc.).

In one or more implementations, operation o11 includes an operation o1148 for electronically receiving the controlled substance directions including directions for at least partial preparation of at least a portion of an ingestible product to be ingested transdermally. An exemplary version of the non-transitory signal bearing medium n100 is depicted as bearing one or more receiving info transdermal instructions i1148 that when executed will direct performance of the operation o1148. In an implementation, the one or more receiving info transdermal instructions i1148 when executed direct electronically receiving the controlled substance directions including directions for at least partial preparation of at least a portion of an ingestible product to be ingested transdermally (e.g. an implementation of the receiver component s528 is configured to electronically receive the controlled substance directions and engage with the processor component s102 to direct the material processing subsystem s700 to at least partially prepare a portion of the ingestible product to be ingested transdermally such as a cream, etc.). Furthermore, the receiving info transdermal electrical circuitry arrangement e1148 when activated will perform the operation o1148. In an implementation, the receiving info transdermal electrical circuitry arrangement e1148, when activated performs electronically receiving the controlled substance directions including directions for at least partial preparation of at least a portion of an ingestible product to be ingested transdermally (e.g. an implementation of the receiver component s528 is configured to electronically receive the controlled substance directions and engage with the processor component s102 to direct the material processing subsystem s700 to at least partially prepare a portion of the ingestible product to be ingested transdermally such as a cream, etc.). In an implementation, the electronically receiving the controlled substance directions including directions for at least partial preparation of at least a portion of an ingestible product to be ingested transdermally is carried out by electronically receiving the controlled substance directions including directions for at least partial preparation of at least a portion of an ingestible product to be ingested transdermally (e.g. an implementation of the receiver component s528 is configured to electronically receive the controlled substance directions and engage with the processor component s102 to direct the material processing subsystem s700 to at least partially prepare a portion of the ingestible product to be ingested transdermally such as a cream, etc.).

In one or more implementations, operation o11 includes an operation o1149 for electronically receiving the controlled substance directions including directions for at least partial preparation of at least a portion of an ingestible product to be used in a capsule form. An exemplary version of the non-transitory signal bearing medium n100 is depicted as bearing one or more receiving info capsule instructions i1149 that when executed will direct performance of the operation o1149. In an implementation, the one or more receiving info capsule instructions i1149 when executed direct electronically receiving the controlled substance directions including directions for at least partial preparation of at least a portion of an ingestible product to be used in a capsule form (e.g. an implementation of the receiver component s528 is configured to electronically receive the controlled substance directions and engage with the processor component s102 to direct the material processing subsystem s700 to at least partially prepare, such as through encapsulation, a portion of the ingestible product such as capsules, etc.). Furthermore, the receiving info capsule electrical circuitry arrangement e1149 when activated will perform the operation o1149. In an implementation, the receiving info capsule electrical circuitry arrangement e1149, when activated performs electronically receiving the controlled substance directions including directions for at least partial preparation of at least a portion of an ingestible product to be used in a capsule form (e.g. an implementation of the receiver component s528 is configured to electronically receive the controlled substance directions and engage with the processor component s102 to direct the material processing subsystem s700 to at least partially prepare, such as through encapsulation, a portion of the ingestible product such as capsules, etc.). In an implementation, the electronically receiving the controlled substance directions including directions for at least partial preparation of at least a portion of an ingestible product to be used in a capsule form is carried out by electronically receiving the controlled substance directions including directions for at least partial preparation of at least a portion of an ingestible product to be used in a capsule form (e.g. an implementation of the receiver component s528 is configured to electronically receive the controlled substance directions and engage with the processor component s102 to direct the material processing subsystem s700 to at least partially prepare, such as through encapsulation, a portion of the ingestible product such as capsules, etc.).

In one or more implementations, operation o11 includes an operation o1150 for electronically receiving the controlled substance directions including directions for at least partial preparation of at least a portion of an ingestible product to be used in sandwich form. An exemplary version of the non-transitory signal bearing medium n100 is depicted as bearing one or more receiving info sandwich instructions i1150 that when executed will direct performance of the operation o1150. In an implementation, the one or more receiving info sandwich instructions i1150 when executed direct electronically receiving the controlled substance directions including directions for at least partial preparation of at least a portion of an ingestible product to be used in sandwich form (e.g. an implementation of the receiver component s528 is configured to electronically receive the controlled substance directions and engage with the processor component s102 to direct the material processing subsystem s700 to at least partially prepare a portion of the ingestible product such as a sandwich, etc.). Furthermore, the receiving info sandwich electrical circuitry arrangement e1150 when activated will perform the operation o1150. In an implementation, the receiving info sandwich electrical circuitry arrangement e1150, when activated performs electronically receiving the controlled substance directions including directions for at least partial preparation of at least a portion of an ingestible product to be used in sandwich form (e.g. an implementation of the receiver component s528 is configured to electronically receive the controlled substance directions and engage with the processor component s102 to direct the material processing subsystem s700 to at least partially prepare a portion of the ingestible product such as a sandwich, etc.). In an implementation, the electronically receiving the controlled substance directions including directions for at least partial preparation of at least a portion of an ingestible product to be used in sandwich form is carried out by electronically receiving the controlled substance directions including directions for at least partial preparation of at least a portion of an ingestible product to be used in sandwich form (e.g. an implementation of the receiver component s528 is configured to electronically receive the controlled substance directions and engage with the processor component s102 to direct the material processing subsystem s700 to at least partially prepare a portion of the ingestible product such as a sandwich, etc.).

Figure 35:
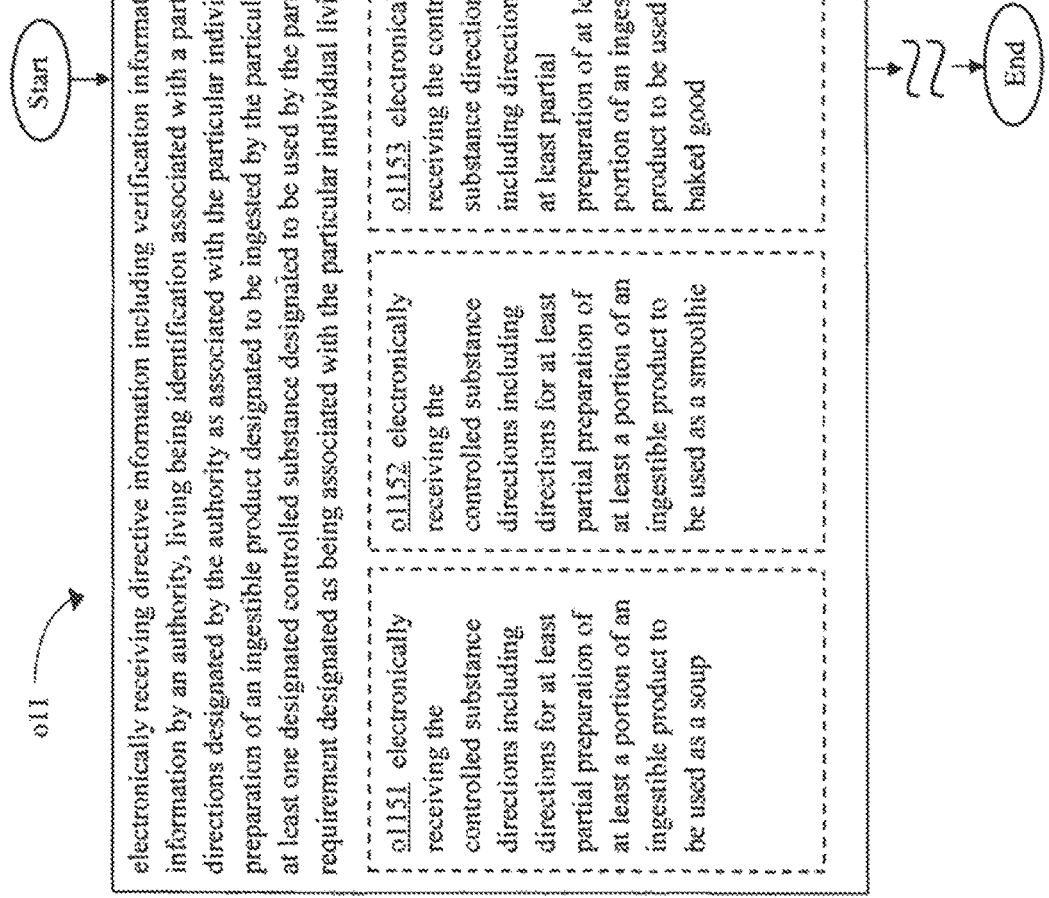
FIG. 35 is a high-level flowchart including exemplary implementations of operation O11 of FIG. 24.

In one or more implementations, as shown in FIG. 35, operation o11 includes an operation o1151 for electronically receiving the controlled substance directions including directions for at least partial preparation of at least a portion of an ingestible product to be used as a soup. An exemplary version of the non-transitory signal bearing medium n100 is depicted as bearing one or more receiving info soup instructions i1151 that when executed will direct performance of the operation o1151. In an implementation, the one or more receiving info soup instructions i1151 when executed direct electronically receiving the controlled substance directions including directions for at least partial preparation of at least a portion of an ingestible product to be used as a soup (e.g. an implementation of the receiver component s528 is configured to electronically receive the controlled substance directions and engage with the processor component s102 to direct the material processing subsystem s700 to at least partially prepare a portion of the ingestible product such as a soup, etc.). Furthermore, the receiving info soup electrical circuitry arrangement e1151 when activated will perform the operation o1151. In an implementation, the receiving info soup electrical circuitry arrangement e1151, when activated performs electronically receiving the controlled substance directions including directions for at least partial preparation of at least a portion of an ingestible product to be used as a soup (e.g. an implementation of the receiver component s528 is configured to electronically receive the controlled substance directions and engage with the processor component s102 to direct the material processing subsystem s700 to at least partially prepare a portion of the ingestible product such as a soup, etc.). In an implementation, the electronically receiving the controlled substance directions including directions for at least partial preparation of at least a portion of an ingestible product to be used as a soup is carried out by electronically receiving the controlled substance directions including directions for at least partial preparation of at least a portion of an ingestible product to be used as a soup (e.g. an implementation of the receiver component s528 is configured to electronically receive the controlled substance directions and engage with the processor component s102 to direct the material processing subsystem s700 to at least partially prepare a portion of the ingestible product such as a soup, etc.).

In one or more implementations, operation o11 includes an operation o1152 for electronically receiving the controlled substance directions including directions for at least partial preparation of at least a portion of an ingestible product to be used as a smoothie. An exemplary version of the non-transitory signal bearing medium n100 is depicted as bearing one or more receiving info smoothie instructions i1152 that when executed will direct performance of the operation o1152. In an implementation, the one or more receiving info smoothie instructions i1152 when executed direct electronically receiving the controlled substance directions including directions for at least partial preparation of at least a portion of an ingestible product to be used as a smoothie (e.g. an implementation of the receiver component s528 is configured to electronically receive the controlled substance directions and engage with the processor component s102 to direct the material processing subsystem s700 to at least partially prepare a portion of the ingestible product such as a smoothie, etc.). Furthermore, the receiving info smoothie electrical circuitry arrangement e1152 when activated will perform the operation o1152. In an implementation, the receiving info smoothie electrical circuitry arrangement e1152, when activated performs electronically receiving the controlled substance directions including directions for at least partial preparation of at least a portion of an ingestible product to be used as a smoothie (e.g. an implementation of the receiver component s528 is configured to electronically receive the controlled substance directions and engage with the processor component s102 to direct the material processing subsystem s700 to at least partially prepare a portion of the ingestible product such as a smoothie, etc.). In an implementation, the electronically receiving the controlled substance directions including directions for at least partial preparation of at least a portion of an ingestible product to be used as a smoothie is carried out by electronically receiving the controlled substance directions including directions for at least partial preparation of at least a portion of an ingestible product to be used as a smoothie (e.g. an implementation of the receiver component s528 is configured to electronically receive the controlled substance directions and engage with the processor component s102 to direct the material processing subsystem s700 to at least partially prepare a portion of the ingestible product such as a smoothie, etc.).

In one or more implementations, operation o11 includes an operation o1153 for electronically receiving the controlled substance directions including directions for at least partial preparation of at least a portion of an ingestible product to be used as a baked good. An exemplary version of the non-transitory signal bearing medium n100 is depicted as bearing one or more receiving info baked instructions i1153 that when executed will direct performance of the operation o1153. In an implementation, the one or more receiving info baked instructions i1153 when executed direct electronically receiving the controlled substance directions including directions for at least partial preparation of at least a portion of an ingestible product to be used as a baked good (e.g. an implementation of the receiver component s528 is configured to electronically receive the controlled substance directions and engage with the processor component s102 to direct the material processing subsystem s700 to at least partially prepare a portion of the ingestible product such as a baked good, etc.). Furthermore, the receiving info baked electrical circuitry arrangement e1153 when activated will perform the operation o1153. In an implementation, the receiving info baked electrical circuitry arrangement e1153, when activated performs electronically receiving the controlled substance directions including directions for at least partial preparation of at least a portion of an ingestible product to be used as a baked good (e.g. an implementation of the receiver component s528 is configured to electronically receive the controlled substance directions and engage with the processor component s102 to direct the material processing subsystem s700 to at least partially prepare a portion of the ingestible product such as a baked good, etc.). In an implementation, the electronically receiving the controlled substance directions including directions for at least partial preparation of at least a portion of an ingestible product to be used as a baked good is carried out by electronically receiving the controlled substance directions including directions for at least partial preparation of at least a portion of an ingestible product to be used as a baked good (e.g. an implementation of the receiver component s528 is configured to electronically receive the controlled substance directions and engage with the processor component s102 to direct the material processing subsystem s700 to at least partially prepare a portion of the ingestible product such as a baked good, etc.).

In one or more implementations, operation o11 includes an operation o1154 for electronically receiving the controlled substance directions including directions for at least partial preparation of at least a portion of an ingestible product to be used as a deposited material. An exemplary version of the non-transitory signal bearing medium n100 is depicted as bearing one or more receiving info deposited instructions i1154 that when executed will direct performance of the operation o1154. In an implementation, the one or more receiving info deposited instructions i1154 when executed direct electronically receiving the controlled substance directions including directions for at least partial preparation of at least a portion of an ingestible product to be used as a deposited material (e.g. an implementation of the receiver component s528 is configured to electronically receive the controlled substance directions and engage with the processor component s102 to direct the material processing subsystem s700 to at least partially prepare a portion of the ingestible product as having deposited material such as a multi-layered cake, etc.). Furthermore, the receiving info deposited electrical circuitry arrangement e1154 when activated will perform the operation o1154. In an implementation, the receiving info deposited electrical circuitry arrangement e1154, when activated performs electronically receiving the controlled substance directions including directions for at least partial preparation of at least a portion of an ingestible product to be used as a deposited material (e.g. an implementation of the receiver component s528 is configured to electronically receive the controlled substance directions and engage with the processor component s102 to direct the material processing subsystem s700 to at least partially prepare a portion of the ingestible product as having deposited material such as a multi-layered cake, etc.). In an implementation, the electronically receiving the controlled substance directions including directions for at least partial preparation of at least a portion of an ingestible product to be used as a deposited material is carried out by electronically receiving the controlled substance directions including directions for at least partial preparation of at least a portion of an ingestible product to be used as a deposited material (e.g. an implementation of the receiver component s528 is configured to electronically receive the controlled substance directions and engage with the processor component s102 to direct the material processing subsystem s700 to at least partially prepare a portion of the ingestible product as having deposited material such as a multi-layered cake, etc.).

In one or more implementations, operation o11 includes an operation o1155 for electronically receiving the controlled substance directions including directions for at least partial preparation of at least a portion of an ingestible product to be used as an assembled concoction. An exemplary version of the non-transitory signal bearing medium n100 is depicted as bearing one or more receiving info assembled instructions i1155 that when executed will direct performance of the operation o1155. In an implementation, the one or more receiving info assembled instructions i1155 when executed direct electronically receiving the controlled substance directions including directions for at least partial preparation of at least a portion of an ingestible product to be used as an assembled concoction (e.g. an implementation of the receiver component s528 is configured to electronically receive the controlled substance directions and engage with the processor component s102 to direct the material processing subsystem s700 to at least partially prepare a portion of the ingestible product as an assembled concoction such as a decorated confection, etc.). Furthermore, the receiving info assembled electrical circuitry arrangement e1155 when activated will perform the operation o1155. In an implementation, the receiving info assembled electrical circuitry arrangement e1155, when activated performs electronically receiving the controlled substance directions including directions for at least partial preparation of at least a portion of an ingestible product to be used as an assembled concoction (e.g. an implementation of the receiver component s528 is configured to electronically receive the controlled substance directions and engage with the processor component s102 to direct the material processing subsystem s700 to at least partially prepare a portion of the ingestible product as an assembled concoction such as a decorated confection, etc.). In an implementation, the electronically receiving the controlled substance directions including directions for at least partial preparation of at least a portion of an ingestible product to be used as an assembled concoction is carried out by electronically receiving the controlled substance directions including directions for at least partial preparation of at least a portion of an ingestible product to be used as an assembled concoction (e.g. an implementation of the receiver component s528 is configured to electronically receive the controlled substance directions and engage with the processor component s102 to direct the material processing subsystem s700 to at least partially prepare a portion of the ingestible product as an assembled concoction such as a decorated confection, etc.).

Figure 36:
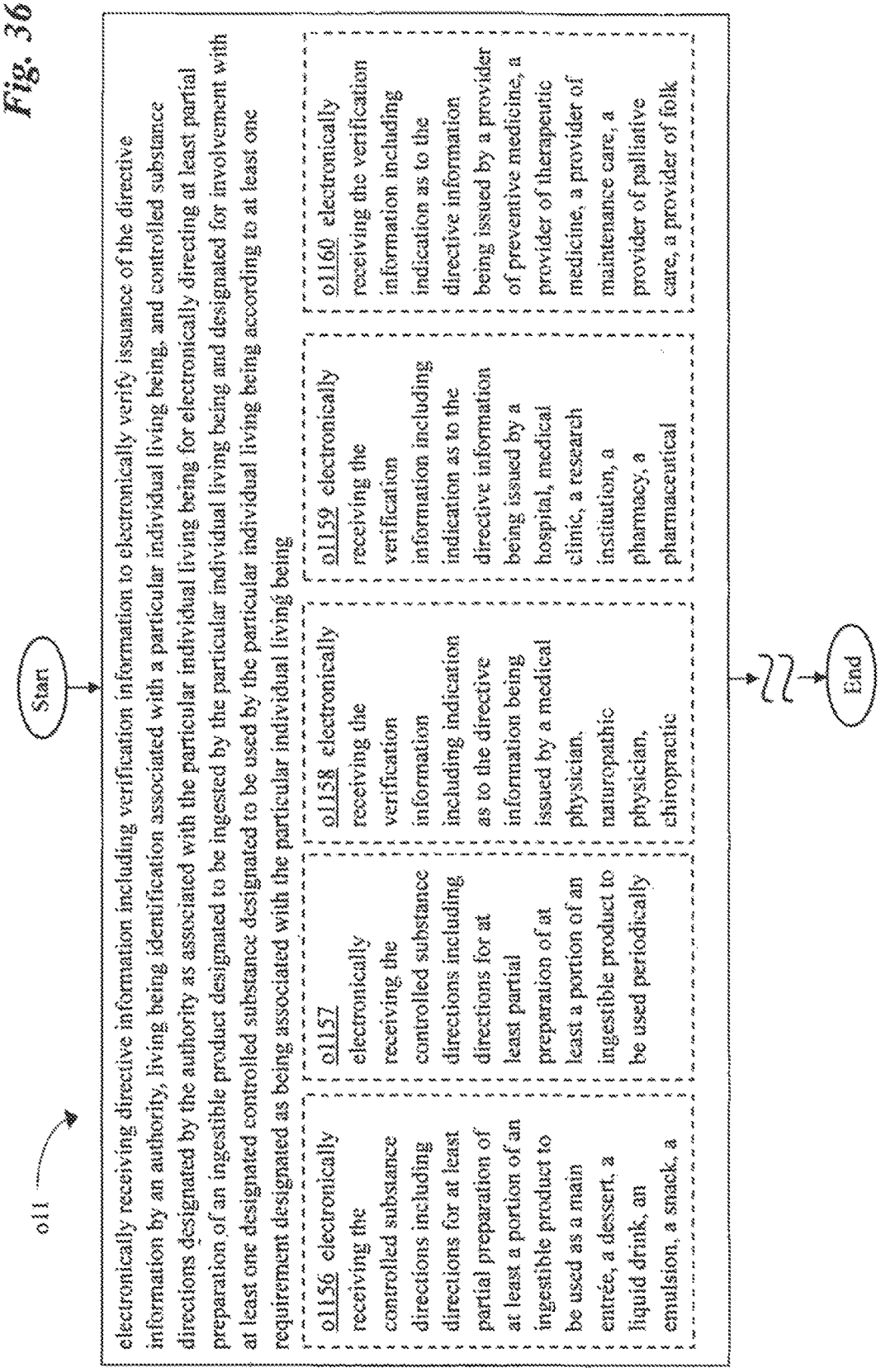
FIG. 36 is a high-level flowchart including exemplary implementations of operation O11 of FIG. 24.

In one or more implementations, as shown in FIG. 36, operation o11 includes an operation o1156 for electronically receiving the controlled substance directions including directions for at least partial preparation of at least a portion of an ingestible product to be used as a main entrée, a dessert, a liquid drink, an emulsion, a snack, a meal, or a combination thereof. An exemplary version of the non-transitory signal bearing medium n100 is depicted as bearing one or more receiving info uses instructions i1156 that when executed will direct performance of the operation o1156. In an implementation, the one or more receiving info uses instructions i1156 when executed direct electronically receiving the controlled substance directions including directions for at least partial preparation of at least a portion of an ingestible product to be used as a main entrée, a dessert, a liquid drink, an emulsion, a snack, a meal, or a combination thereof (e.g. an implementation of the receiver component s528 is configured to electronically receive the controlled substance directions and engage with the processor component s102 to direct the material processing subsystem s700 to at least partially prepare a portion of the ingestible product such as a steak, etc.). Furthermore, the receiving info uses electrical circuitry arrangement e1156 when activated will perform the operation o1156. In an implementation, the receiving info uses electrical circuitry arrangement e1156, when activated performs electronically receiving the controlled substance directions including directions for at least partial preparation of at least a portion of an ingestible product to be used as a main entrée, a dessert, a liquid drink, an emulsion, a snack, a meal, or a combination thereof (e.g. an implementation of the receiver component s528 is configured to electronically receive the controlled substance directions and engage with the processor component s102 to direct the material processing subsystem s700 to at least partially prepare a portion of the ingestible product such as a steak, etc.). In an implementation, the electronically receiving the controlled substance directions including directions for at least partial preparation of at least a portion of an ingestible product to be used as a main entrée, a dessert, a liquid drink, an emulsion, a snack, a meal, or a combination thereof is carried out by electronically receiving the controlled substance directions including directions for at least partial preparation of at least a portion of an ingestible product to be used as a main entrée, a dessert, a liquid drink, an emulsion, a snack, a meal, or a combination thereof (e.g. an implementation of the receiver component s528 is configured to electronically receive the controlled substance directions and engage with the processor component s102 to direct the material processing subsystem s700 to at least partially prepare a portion of the ingestible product such as a steak, etc.).

In one or more implementations, operation o11 includes an operation o1157 for electronically receiving the controlled substance directions including directions for at least partial preparation of at least a portion of an ingestible product to be used periodically. An exemplary version of the non-transitory signal bearing medium n100 is depicted as bearing one or more receiving info periods instructions i1157 that when executed will direct performance of the operation o1157. In an implementation, the one or more receiving info periods instructions i1157 when executed direct electronically receiving the controlled substance directions including directions for at least partial preparation of at least a portion of an ingestible product to be used periodically (e.g. an implementation of the receiver component s528 is configured to electronically receive the controlled substance directions and engage with the processor component s102 to direct the material processing subsystem s700 to at least partially prepare a portion of the ingestible product such as once a week, etc.). Furthermore, the receiving info periods electrical circuitry arrangement e1157 when activated will perform the operation o1157. In an implementation, the receiving info periods electrical circuitry arrangement e1157, when activated performs electronically receiving the controlled substance directions including directions for at least partial preparation of at least a portion of an ingestible product to be used periodically (e.g. an implementation of the receiver component s528 is configured to electronically receive the controlled substance directions and engage with the processor component s102 to direct the material processing subsystem s700 to at least partially prepare a portion of the ingestible product such as once a week, etc.). In an implementation, the electronically receiving the controlled substance directions including directions for at least partial preparation of at least a portion of an ingestible product to be used periodically is carried out by electronically receiving the controlled substance directions including directions for at least partial preparation of at least a portion of an ingestible product to be used periodically (e.g. an implementation of the receiver component s528 is configured to electronically receive the controlled substance directions and engage with the processor component s102 to direct the material processing subsystem s700 to at least partially prepare a portion of the ingestible product such as once a week, etc.).

In one or more implementations, operation o11 includes an operation o1158 for electronically receiving the verification information including indication as to the directive information being issued by a medical physician, naturopathic physician, chiropractic physician, physician, nurse practitioner, nurse, dentist, or a combination thereof. An exemplary version of the non-transitory signal bearing medium n100 is depicted as bearing one or more receiving info care giver instructions i1158 that when executed will direct performance of the operation o1158. In an implementation, the one or more receiving info care giver instructions i1158 when executed direct electronically receiving the verification information including indication as to the directive information being issued by a medical physician, naturopathic physician, chiropractic physician, physician, nurse practitioner, nurse, dentist, or a combination thereof (e.g. an implementation of the receiver component s528 is configured to electronically receive the verification information in a format for the processor component s102 to identify the issuer of the directive information as a health care provider such as a medical physician, etc.). Furthermore, the receiving info care giver electrical circuitry arrangement e1158 when activated will perform the operation o1158. In an implementation, the receiving info care giver electrical circuitry arrangement e1158, when activated performs electronically receiving the verification information including indication as to the directive information being issued by a medical physician, naturopathic physician, chiropractic physician, physician, nurse practitioner, nurse, dentist, or a combination thereof (e.g. an implementation of the receiver component s528 is configured to electronically receive the verification information in a format for the processor component s102 to identify the issuer of the directive information as a health care provider such as a medical physician, etc.). In an implementation, the electronically receiving the verification information including indication as to the directive information being issued by a medical physician, naturopathic physician, chiropractic physician, physician, nurse practitioner, nurse, dentist, or a combination thereof is carried out by electronically receiving the verification information including indication as to the directive information being issued by a medical physician, naturopathic physician, chiropractic physician, physician, nurse practitioner, nurse, dentist, or a combination thereof (e.g. an implementation of the receiver component s528 is configured to electronically receive the verification information in a format for the processor component s102 to identify the issuer of the directive information as a health care provider such as a medical physician, etc.).

In one or more implementations, operation o11 includes an operation o1159 for electronically receiving the verification information including indication as to the directive information being issued by a hospital, medical clinic, a research institution, a pharmacy, a pharmaceutical company, a computer software company, or a combination thereof. An exemplary version of the non-transitory signal bearing medium n100 is depicted as bearing one or more receiving info organization instructions i1159 that when executed will direct performance of the operation o1159. In an implementation, the one or more receiving info organization instructions i1159 when executed direct electronically receiving the verification information including indication as to the directive information being issued by a hospital, medical clinic, a research institution, a pharmacy, a pharmaceutical company, a computer software company, or a combination thereof (e.g. an implementation of the receiver component s528 is configured to electronically receive the verification information in a format for the processor component s102 to identify the issuer of the directive information as an institution such as a medical clinic, etc.). Furthermore, the receiving info organization electrical circuitry arrangement e1159 when activated will perform the operation o1159. In an implementation, the receiving info organization electrical circuitry arrangement e1159, when activated performs electronically receiving the verification information including indication as to the directive information being issued by a hospital, medical clinic, a research institution, a pharmacy, a pharmaceutical company, a computer software company, or a combination thereof (e.g. an implementation of the receiver component s528 is configured to electronically receive the verification information in a format for the processor component s102 to identify the issuer of the directive information as an institution such as a medical clinic, etc.). In an implementation, the electronically receiving the verification information including indication as to the directive information being issued by a hospital, medical clinic, a research institution, a pharmacy, a pharmaceutical company, a computer software company, or a combination thereof is carried out by electronically receiving the verification information including indication as to the directive information being issued by a hospital, medical clinic, a research institution, a pharmacy, a pharmaceutical company, a computer software company, or a combination thereof (e.g. an implementation of the receiver component s528 is configured to electronically receive the verification information in a format for the processor component s102 to identify the issuer of the directive information as an institution such as a medical clinic, etc.).

In one or more implementations, operation o11 includes an operation o1160 for electronically receiving the verification information including indication as to the directive information being issued by a provider of preventive medicine, a provider of therapeutic medicine, a provider of maintenance care, a provider of palliative care, a provider of folk medicine, or a combination thereof. An exemplary version of the non-transitory signal bearing medium n100 is depicted as bearing one or more receiving info preventive instructions i1160 that when executed will direct performance of the operation o1160. In an implementation, the one or more receiving info preventive instructions i1160 when executed direct electronically receiving the verification information including indication as to the directive information being issued by a provider of preventive medicine, a provider of therapeutic medicine, a provider of maintenance care, a provider of palliative care, a provider of folk medicine, or a combination thereof (e.g. an implementation of the receiver component s528 is configured to electronically receive the verification information in a format for the processor component s102 to identify the issuer of the directive information as a provider such as a provider of preventive medicine, etc.). Furthermore, the receiving info preventive electrical circuitry arrangement e1160 when activated will perform the operation o1160. In an implementation, the receiving info preventive electrical circuitry arrangement e1160, when activated performs electronically receiving the verification information including indication as to the directive information being issued by a provider of preventive medicine, a provider of therapeutic medicine, a provider of maintenance care, a provider of palliative care, a provider of folk medicine, or a combination thereof (e.g. an implementation of the receiver component s528 is configured to electronically receive the verification information in a format for the processor component s102 to identify the issuer of the directive information as a provider such as a provider of preventive medicine, etc.). In an implementation, the electronically receiving the verification information including indication as to the directive information being issued by a provider of preventive medicine, a provider of therapeutic medicine, a provider of maintenance care, a provider of palliative care, a provider of folk medicine, or a combination thereof is carried out by electronically receiving the verification information including indication as to the directive information being issued by a provider of preventive medicine, a provider of therapeutic medicine, a provider of maintenance care, a provider of palliative care, a provider of folk medicine, or a combination thereof (e.g. an implementation of the receiver component s528 is configured to electronically receive the verification information in a format for the processor component s102 to identify the issuer of the directive information as a provider such as a provider of preventive medicine, etc.).

Figure 37:
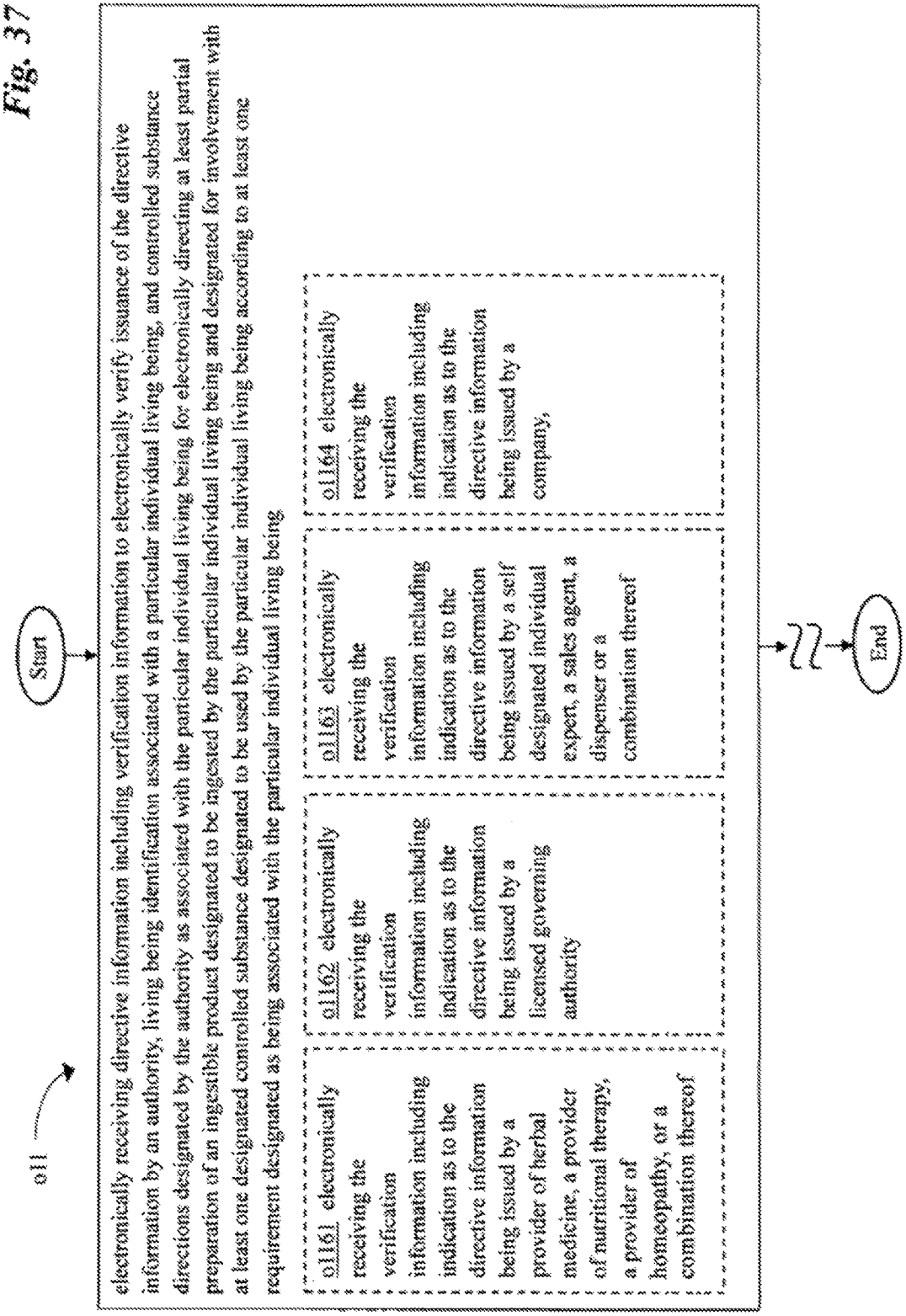
FIG. 37 is a high-level flowchart including exemplary implementations of operation O11 of FIG. 24.

In one or more implementations, as shown in FIG. 37, operation o11 includes an operation o1161 for electronically receiving the verification information including indication as to the directive information being issued by a provider of herbal medicine, a provider of nutritional therapy, a provider of homeopathy, or a combination thereof. An exemplary version of the non-transitory signal bearing medium n100 is depicted as bearing one or more receiving info alternative instructions i1161 that when executed will direct performance of the operation o1161. In an implementation, the one or more receiving info alternative instructions i1161 when executed direct electronically receiving the verification information including indication as to the directive information being issued by a provider of herbal medicine, a provider of nutritional therapy, a provider of homeopathy, or a combination thereof (e.g. an implementation of the receiver component s528 is configured to electronically receive the verification information in a format for the processor component s102 to identify the issuer of the directive information as a provider such as a provider of homeopathy, etc.). Furthermore, the receiving info alternative electrical circuitry arrangement e1161 when activated will perform the operation o1161. In an implementation, the receiving info alternative electrical circuitry arrangement e1161, when activated performs electronically receiving the verification information including indication as to the directive information being issued by a provider of herbal medicine, a provider of nutritional therapy, a provider of homeopathy, or a combination thereof (e.g. an implementation of the receiver component s528 is configured to electronically receive the verification information in a format for the processor component s102 to identify the issuer of the directive information as a provider such as a provider of homeopathy, etc.). In an implementation, the electronically receiving the verification information including indication as to the directive information being issued by a provider of herbal medicine, a provider of nutritional therapy, a provider of homeopathy, or a combination thereof is carried out by electronically receiving the verification information including indication as to the directive information being issued by a provider of herbal medicine, a provider of nutritional therapy, a provider of homeopathy, or a combination thereof (e.g. an implementation of the receiver component s528 is configured to electronically receive the verification information in a format for the processor component s102 to identify the issuer of the directive information as a provider such as a provider of homeopathy, etc.).

In one or more implementations, operation o11 includes an operation o1162 for electronically receiving the verification information including indication as to the directive information being issued by a licensed governing authority. An exemplary version of the non-transitory signal bearing medium n100 is depicted as bearing one or more receiving info authority instructions i1162 that when executed will direct performance of the operation o1162. In an implementation, the one or more receiving info authority instructions i1162 when executed direct electronically receiving the verification information including indication as to the directive information being issued by a licensed governing authority (e.g. an implementation of the receiver component s528 is configured to electronically receive the verification information in a format for the processor component s102 to identify the issuer of the directive information as a licensed governing authority such as a veterans administration hospital, etc.). Furthermore, the receiving info authority electrical circuitry arrangement e1162 when activated will perform the operation o1162. In an implementation, the receiving info authority electrical circuitry arrangement e1162, when activated performs electronically receiving the verification information including indication as to the directive information being issued by a licensed governing authority (e.g. an implementation of the receiver component s528 is configured to electronically receive the verification information in a format for the processor component s102 to identify the issuer of the directive information as a licensed governing authority such as a veterans administration hospital, etc.). In an implementation, the electronically receiving the verification information including indication as to the directive information being issued by a licensed governing authority is carried out by electronically receiving the verification information including indication as to the directive information being issued by a licensed governing authority (e.g. an implementation of the receiver component s528 is configured to electronically receive the verification information in a format for the processor component s102 to identify the issuer of the directive information as a licensed governing authority such as a veterans administration hospital, etc.).

In one or more implementations, operation o11 includes an operation o1163 for electronically receiving the verification information including indication as to the directive information being issued by a self designated individual expert, a sales agent, a dispenser or a combination thereof. An exemplary version of the non-transitory signal bearing medium n100 is depicted as bearing one or more receiving info individual instructions i1163 that when executed will direct performance of the operation o1163. In an implementation, the one or more receiving info individual instructions i1163 when executed direct electronically receiving the verification information including indication as to the directive information being issued by a self designated individual expert, a sales agent, a dispenser or a combination thereof (e.g. an implementation of the receiver component s528 is configured to electronically receive the verification information in a format for the processor component s102 to identify the issuer of the directive information as an individual such as a self designated individual expert, etc.). Furthermore, the receiving info individual electrical circuitry arrangement e1163 when activated will perform the operation o1163. In an implementation, the receiving info individual electrical circuitry arrangement e1163, when activated performs electronically receiving the verification information including indication as to the directive information being issued by a self designated individual expert, a sales agent, a dispenser or a combination thereof (e.g. an implementation of the receiver component s528 is configured to electronically receive the verification information in a format for the processor component s102 to identify the issuer of the directive information as an individual such as a self designated individual expert, etc.). In an implementation, the electronically receiving the verification information including indication as to the directive information being issued by a self designated individual expert, a sales agent, a dispenser or a combination thereof is carried out by electronically receiving the verification information including indication as to the directive information being issued by a self designated individual expert, a sales agent, a dispenser or a combination thereof (e.g. an implementation of the receiver component s528 is configured to electronically receive the verification information in a format for the processor component s102 to identify the issuer of the directive information as an individual such as a self designated individual expert, etc.).

In one or more implementations, operation o11 includes an operation o1164 for electronically receiving the verification information including indication as to the directive information being issued by a company. An exemplary version of the non-transitory signal bearing medium n100 is depicted as bearing one or more receiving info company instructions i1164 that when executed will direct performance of the operation o1164. In an implementation, the one or more receiving info company instructions i1164 when executed direct electronically receiving the verification information including indication as to the directive information being issued by a company (e.g. an implementation of the receiver component s528 is configured to electronically receive the verification information in a format for the processor component s102 to identify the issuer of the directive information as a company such as a pharmaceutical company, etc.). Furthermore, the receiving info company electrical circuitry arrangement e1164 when activated will perform the operation o1164. In an implementation, the receiving info company electrical circuitry arrangement e1164, when activated performs electronically receiving the verification information including indication as to the directive information being issued by a company (e.g. an implementation of the receiver component s528 is configured to electronically receive the verification information in a format for the processor component s102 to identify the issuer of the directive information as a company such as a pharmaceutical company, etc.). In an implementation, the electronically receiving the verification information including indication as to the directive information being issued by a company, is carried out by electronically receiving the verification information including indication as to the directive information being issued by a company (e.g. an implementation of the receiver component s528 is configured to electronically receive the verification information in a format for the processor component s102 to identify the issuer of the directive information as a company such as a pharmaceutical company, etc.).

As shown in FIG. 24, the operational flow o10 proceeds to operation o12 for electronically using the electronically received directive information to electronically direct control of the at least partial preparation of the ingestible product designated to be ingested by the particular individual living being upon electronically verifying, thru electronic use of the directive information that the authority is authorized to issue the controlled substance instruction and that the controlled substance instruction has been issued by the authority. An exemplary version of the non-transitory signal bearing medium n100 is depicted as bearing one or more controlling prep upon verify instructions i12 that when executed will direct performance of the operation o12. In an implementation, the one or more controlling prep upon verify instructions i12 when executed direct electronically using the electronically received directive information to electronically direct control of the at least partial preparation of the ingestible product designated to be ingested by the particular individual living being (e.g. an implementation of the processor component s102 controls the material processing subsystem s702 to execute at least partial preparation of, for instance, a meal replacement bar containing an sinus medication for a teenage human, etc.) upon electronically verifying, thru electronic use of the directive information that the authority is authorized to issue the controlled substance instruction and that the controlled substance instruction has been issued by the authority (e.g. an implementation of the processing component s102 runs a comparison analysis of data contained in the directive information to determine that a particular person is a physician authorized to issue directive information and that the received directive information has been issued by the particular person, etc.). Furthermore, the controlling prep upon verify electrical circuitry arrangement e12 when activated will perform the operation o12. In an implementation, the controlling prep upon verify electrical circuitry arrangement e12, when activated performs electronically using the electronically received directive information to electronically direct control of the at least partial preparation of the ingestible product designated to be ingested by the particular individual living being (e.g. an implementation of the processor component s102 controls the material processing subsystem s702 to execute at least partial preparation of, for instance, a meal replacement bar containing an sinus medication for a teenage human, etc.) upon electronically verifying, thru electronic use of the directive information that the authority is authorized to issue the controlled substance instruction and that the controlled substance instruction has been issued by the authority (e.g. an implementation of the processing component s102 runs a comparison analysis of data contained in the directive information to determine that a particular person is a physician authorized to issue directive information and that the received directive information has been issued by the particular person, etc.). In an implementation, the electronically using the electronically received directive information to electronically direct control of the at least partial preparation of the ingestible product designated to be ingested by the particular individual living being upon electronically verifying, thru electronic use of the directive information that the authority is authorized to issue the controlled substance instruction and that the controlled substance instruction has been issued by the authority is carried out by electronically using the electronically received directive information to electronically direct control of the at least partial preparation of the ingestible product designated to be ingested by the particular individual living being (e.g. an implementation of the processor component s102 controls the material processing subsystem s702 to execute at least partial preparation of, for instance, a meal replacement bar containing an sinus medication for a teenage human, etc.) upon electronically verifying, thru electronic use of the directive information that the authority is authorized to issue the controlled substance instruction and that the controlled substance instruction has been issued by the authority (e.g. an implementation of the processing component s102 runs a comparison analysis of data contained in the directive information to determine that a particular person is a physician authorized to issue directive information and that the received directive information has been issued by the particular person, etc.).

Figure 38:
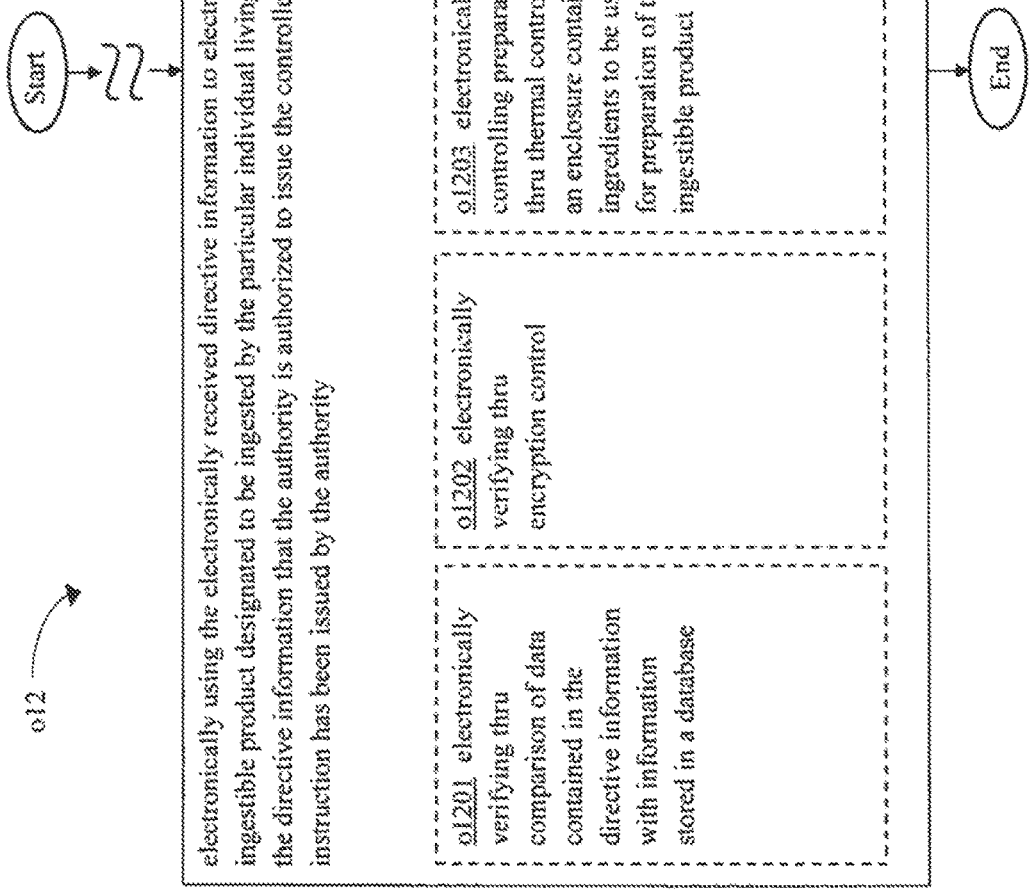
FIG. 38 is a high-level flowchart including exemplary implementations of operation O12 of FIG. 24.

In one or more implementations, as shown in FIG. 38, operation o12 includes an operation o1201 for electronically verifying thru comparison of data contained in the directive information with information stored in a database. An exemplary version of the non-transitory signal bearing medium n100 is depicted as bearing one or more verifying thru comparison instructions i1201 that when executed will direct performance of the operation o1201. In an implementation, the one or more verifying thru comparison instructions i1201 when executed direct electronically verifying thru comparison of data contained in the directive information with information stored in a database (e.g. an implementation of the processor component s102 is configured to electronically compare data contained in the directive information and received by the receiver component s528 with information stored in the hard drive component s222, etc.). Furthermore, the verifying thru comparison electrical circuitry arrangement e1201 when activated will perform the operation o1201. In an implementation, the verifying thru comparison electrical circuitry arrangement e1201, when activated performs electronically verifying thru comparison of data contained in the directive information with information stored in a database (e.g. an implementation of the processor component s102 is configured to electronically compare data contained in the directive information and received by the receiver component s528 with information stored in the hard drive component s222, etc.). In an implementation, the electronically verifying thru comparison of data contained in the directive information with information stored in a database is carried out by electronically verifying thru comparison of data contained in the directive information with information stored in a database (e.g. an implementation of the processor component s102 is configured to electronically compare data contained in the directive information and received by the receiver component s528 with information stored in the hard drive component s222, etc.).

In one or more implementations, operation o12 includes an operation o1202 for electronically verifying thru encryption control. An exemplary version of the non-transitory signal bearing medium n100 is depicted as bearing one or more verifying thru encryption instructions i1202 that when executed will direct performance of the operation o1202. In an implementation, the one or more verifying thru encryption instructions i1202 when executed direct electronically verifying thru encryption control (e.g. an implementation of the processor component s102 is configured to electronically implement an encryption key control that a physician was authorized to issue the controlled substance information pertaining to a pharmaceutical medication, etc.). Furthermore, the verifying thru encryption electrical circuitry arrangement e1202 when activated will perform the operation o1202. In an implementation, the verifying thru encryption electrical circuitry arrangement e1202, when activated performs electronically verifying thru encryption control (e.g. an implementation of the processor component s102 is configured to electronically implement an encryption key control that a physician was authorized to issue the controlled substance information pertaining to a pharmaceutical medication, etc.). In an implementation, the electronically verifying thru encryption control is carried out by electronically verifying thru encryption control (e.g. an implementation of the processor component s102 is configured to electronically implement an encryption key control that a physician was authorized to issue the controlled substance information pertaining to a pharmaceutical medication, etc.).

In one or more implementations, operation o12 includes an operation o1203 for electronically controlling preparation thru thermal control of an enclosure containing ingredients to be used for preparation of the ingestible product. An exemplary version of the non-transitory signal bearing medium n100 is depicted as bearing one or more control prep thermal instructions i1203 that when executed will direct performance of the operation o1203. In an implementation, the one or more control prep thermal instructions i1203 when executed direct electronically controlling preparation thru thermal control of an enclosure containing ingredients to be used for preparation of the ingestible product (e.g. an implementation of the processor component s102 is configured to electronically control the laser component s708 according to a temperature profile included in the directive information, etc.). Furthermore, the control prep thermal electrical circuitry arrangement e1203 when activated will perform the operation o1203. In an implementation, the control prep thermal electrical circuitry arrangement e1203, when activated performs electronically controlling preparation thru thermal control of an enclosure containing ingredients to be used for preparation of the ingestible product (e.g. an implementation of the processor component s102 is configured to electronically control the laser component s708 according to a temperature profile included in the directive information, etc.). In an implementation, the electronically controlling preparation thru thermal control of an enclosure containing ingredients to be used for preparation of the ingestible product is carried out by electronically controlling preparation thru thermal control of an enclosure containing ingredients to be used for preparation of the ingestible product (e.g. an implementation of the processor component s102 is configured to electronically control the laser component s708 according to a temperature profile included in the directive information, etc.).

In one or more implementations, operation o12 includes an operation o1204 for electronically controlling preparation thru heating control of an enclosure containing ingredients to be used for preparation of the ingestible product. An exemplary version of the non-transitory signal bearing medium n100 is depicted as bearing one or more control prep heating instructions i1204 that when executed will direct performance of the operation o1204. In an implementation, the one or more control prep heating instructions i1204 when executed direct electronically controlling preparation thru heating control of an enclosure containing ingredients to be used for preparation of the ingestible product (e.g. an implementation of the processor component s102 is configured to electronically control the heating component s702 according to a temperature profile included in the directive information, etc.). Furthermore, the verifying thru comparison electrical circuitry arrangement e1204 when activated will perform the operation o1204. In an implementation, the control prep heating electrical circuitry arrangement e1204, when activated performs electronically controlling preparation thru heating control of an enclosure containing ingredients to be used for preparation of the ingestible product (e.g. an implementation of the processor component s102 is configured to electronically control the heating component s702 according to a temperature profile included in the directive information, etc.). In an implementation, the electronically controlling preparation thru heating control of an enclosure containing ingredients to be used for preparation of the ingestible product is carried out by electronically controlling preparation thru heating control of an enclosure containing ingredients to be used for preparation of the ingestible product (e.g. an implementation of the processor component s102 is configured to electronically control the heating component s702 according to a temperature profile included in the directive information, etc.).

In one or more implementations, operation o12 includes an operation o1205 for electronically controlling preparation thru cooling control of an enclosure containing ingredients to be used for preparation of the ingestible product. An exemplary version of the non-transitory signal bearing medium n100 is depicted as bearing one or more control prep cooling instructions i1205 that when executed will direct performance of the operation o1205. In an implementation, the one or more control prep cooling instructions i1205 when executed direct electronically controlling preparation thru cooling control of an enclosure containing ingredients to be used for preparation of the ingestible product (e.g. an implementation of the processor component s102 is configured to electronically control the cooling component s704 according to a temperature profile included in the directive information, etc.). Furthermore, the control prep cooling electrical circuitry arrangement e1205 when activated will perform the operation o1205. In an implementation, the control prep cooling electrical circuitry arrangement e1205, when activated performs electronically controlling preparation thru cooling control of an enclosure containing ingredients to be used for preparation of the ingestible product (e.g. an implementation of the processor component s102 is configured to electronically control the cooling component s704 according to a temperature profile included in the directive information, etc.). In an implementation, the electronically controlling preparation thru cooling control of an enclosure containing ingredients to be used for preparation of the ingestible product is carried out by electronically controlling preparation thru cooling control of an enclosure containing ingredients to be used for preparation of the ingestible product (e.g. an implementation of the processor component s102 is configured to electronically control the cooling component s704 according to a temperature profile included in the directive information, etc.).

In one or more implementations, as shown in FIG. 39, operation o12 includes an operation o1206 for electronically controlling preparation thru portion size control of an amount of the controlled substance to be used in preparation of the ingestible product. An exemplary version of the non-transitory signal bearing medium n100 is depicted as bearing one or more control prep portion size instructions i1206 that when executed will direct performance of the operation o1206. In an implementation, the one or more control prep portion size instructions i1206 when executed direct electronically controlling preparation thru portion size control of an amount of the controlled substance to be used in preparation of the ingestible product (e.g. an implementation of the processor component s102 is configured to electronically control the sorting component s728 according to an ingredient size distribution profile included in the directive information, etc.). Furthermore, the control prep portion size electrical circuitry arrangement e1206 when activated will perform the operation o1205. In an implementation, the control prep portion size electrical circuitry arrangement e1206, when activated performs electronically controlling preparation thru portion size control of an amount of the controlled substance to be used in preparation of the ingestible product (e.g. an implementation of the processor component s102 is configured to electronically control the sorting component s728 according to an ingredient size distribution profile included in the directive information, etc.). In an implementation, the electronically controlling preparation thru portion size control of an amount of the controlled substance to be used in preparation of the ingestible product is carried out by electronically controlling preparation thru portion size control of an amount of the controlled substance to be used in preparation of the ingestible product (e.g. an implementation of the processor component s102 is configured to electronically control the sorting component s728 according to an ingredient size distribution profile included in the directive information, etc.).

In one or more implementations, operation o12 includes an operation o1207 for electronically controlling preparation thru controlling amount of ingredient mixing during preparation of the ingestible product. An exemplary version of the non-transitory signal bearing medium n100 is depicted as bearing one or more control prep mixing instructions i1207 that when executed will direct performance of the operation o1207. In an implementation, the one or more control prep mixing instructions i1207 when executed direct electronically controlling preparation thru controlling amount of ingredient mixing during preparation of the ingestible product (e.g. an implementation of the processor component s102 is configured to electronically control the mixer component s716 according to a mixing profile included in the directive information, etc.). Furthermore, the control prep mixing electrical circuitry arrangement e1207 when activated will perform the operation o1207. In an implementation, the control prep mixing electrical circuitry arrangement e1207, when activated performs electronically controlling preparation thru controlling amount of ingredient mixing during preparation of the ingestible product (e.g. an implementation of the processor component s102 is configured to electronically control the mixer component s716 according to a mixing profile included in the directive information, etc.). In an implementation, the electronically controlling preparation thru controlling amount of ingredient mixing during preparation of the ingestible product is carried out by electronically controlling preparation thru controlling amount of ingredient mixing during preparation of the ingestible product (e.g. an implementation of the processor component s102 is configured to electronically control the mixer component s716 according to a mixing profile included in the directive information, etc.).

In one or more implementations, operation o12 includes an operation o1208 for electronically controlling preparation thru control of radiation emitted within an enclosure containing ingredients to be used for preparation of the ingestible product. An exemplary version of the non-transitory signal bearing medium n100 is depicted as bearing one or more control prep radiation instructions i1208 that when executed will direct performance of the operation o1208. In an implementation, the one or more control prep radiation instructions i1208 when executed direct electronically controlling preparation thru control of radiation emitted within an enclosure containing ingredients to be used for preparation of the ingestible product (e.g. an implementation of the processor component s102 is configured to electronically control the energy emitting component s724 configured to emit radiation according to a radiation profile included in the directive information, etc.). Furthermore, the control prep radiation electrical circuitry arrangement e1208 when activated will perform the operation o1208. In an implementation, the control prep radiation electrical circuitry arrangement e1208, when activated performs electronically controlling preparation thru control of radiation emitted within an enclosure containing ingredients to be used for preparation of the ingestible product (e.g. an implementation of the processor component s102 is configured to electronically control the energy emitting component s724 configured to emit radiation according to a radiation profile included in the directive information, etc.). In an implementation, the electronically controlling preparation thru control of radiation emitted within an enclosure containing ingredients to be used for preparation of the ingestible product is carried out by electronically controlling preparation thru control of radiation emitted within an enclosure containing ingredients to be used for preparation of the ingestible product (e.g. an implementation of the processor component s102 is configured to electronically control the energy emitting component s724 configured to emit radiation according to a radiation profile included in the directive information, etc.).

In one or more implementations, operation o12 includes an operation o1209 for electronically controlling preparation thru control of sound emitted within an enclosure containing ingredients to be used for preparation of the ingestible product. An exemplary version of the non-transitory signal bearing medium n100 is depicted as bearing one or more control prep sound instructions i1209 that when executed will direct performance of the operation o1209. In an implementation, the one or more control prep sound instructions i1209 when executed direct electronically controlling preparation thru control of sound emitted within an enclosure containing ingredients to be used for preparation of the ingestible product (e.g. an implementation of the processor component s102 is configured to electronically control the acoustic energy component s718 according to an acoustic energy profile included in the directive information, etc.). Furthermore, the control prep sound electrical circuitry arrangement e1209 when activated will perform the operation o1209. In an implementation, the control prep sound electrical circuitry arrangement e1209, when activated performs electronically controlling preparation thru control of sound emitted within an enclosure containing ingredients to be used for preparation of the ingestible product (e.g. an implementation of the processor component s102 is configured to electronically control the acoustic energy component s718 according to an acoustic energy profile included in the directive information, etc.). In an implementation, the electronically controlling preparation thru control of sound emitted within an enclosure containing ingredients to be used for preparation of the ingestible product is carried out by electronically controlling preparation thru control of sound emitted within an enclosure containing ingredients to be used for preparation of the ingestible product (e.g. an implementation of the processor component s102 is configured to electronically control the acoustic energy component s718 according to an acoustic energy profile included in the directive information, etc.).

In one or more implementations, operation o12 includes an operation o1210 for electronically controlling preparation thru control of infrared radiation emitted within an enclosure containing ingredients to be used for preparation of the ingestible product. An exemplary version of the non-transitory signal bearing medium n100 is depicted as bearing one or more control prep infrared instructions i1210 that when executed will direct performance of the operation o1210. In an implementation, the one or more control prep infrared instructions i1210 when executed direct electronically controlling preparation thru control of infrared radiation emitted within an enclosure containing ingredients to be used for preparation of the ingestible product (e.g. an implementation of the processor component s102 is configured to electronically control the infrared component s730 according to a temperature profile included in the directive information, etc.). Furthermore, the control prep infrared electrical circuitry arrangement e1210 when activated will perform the operation o1210. In an implementation, the control prep infrared electrical circuitry arrangement e1210, when activated performs electronically controlling preparation thru control of infrared radiation emitted within an enclosure containing ingredients to be used for preparation of the ingestible product (e.g. an implementation of the processor component s102 is configured to electronically control the infrared component s730 according to a temperature profile included in the directive information, etc.). In an implementation, the electronically controlling preparation thru control of infrared radiation emitted within an enclosure containing ingredients to be used for preparation of the ingestible product is carried out by electronically controlling preparation thru control of infrared radiation emitted within an enclosure containing ingredients to be used for preparation of the ingestible product (e.g. an implementation of the processor component s102 is configured to electronically control the infrared component s730 according to a temperature profile included in the directive information, etc.).

In one or more implementations, as shown in FIG. 40, operation o12 includes an operation o1211 for electronically controlling preparation thru control of microwave radiation emitted within an enclosure containing ingredients to be used for preparation of the ingestible product. An exemplary version of the non-transitory signal bearing medium n100 is depicted as bearing one or more control prep microwave instructions i1211 that when executed will direct performance of the operation o1211. In an implementation, the one or more control prep microwave instructions i1211 when executed direct electronically controlling preparation thru control of microwave radiation emitted within an enclosure containing ingredients to be used for preparation of the ingestible product (e.g. an implementation of the processor component s102 is configured to electronically control the microwave component s706 according to a temperature profile included in the directive information, etc.). Furthermore, the control prep microwave electrical circuitry arrangement e1211 when activated will perform the operation o1211. In an implementation, the control prep microwave electrical circuitry arrangement e1211, when activated performs electronically controlling preparation thru control of microwave radiation emitted within an enclosure containing ingredients to be used for preparation of the ingestible product (e.g. an implementation of the processor component s102 is configured to electronically control the microwave component s706 according to a temperature profile included in the directive information, etc.). In an implementation, the electronically controlling preparation thru control of microwave radiation emitted within an enclosure containing ingredients to be used for preparation of the ingestible product is carried out by electronically controlling preparation thru control of microwave radiation emitted within an enclosure containing ingredients to be used for preparation of the ingestible product (e.g. an implementation of the processor component s102 is configured to electronically control the microwave component s706 according to a temperature profile included in the directive information, etc.).

In one or more implementations, operation o12 includes an operation o1212 for electronically controlling preparation thru control of an outlet of an ingredient container holding an ingredient used for preparation of the ingestible product. An exemplary version of the non-transitory signal bearing medium n100 is depicted as bearing one or more control prep container instructions i1212 that when executed will direct performance of the operation o1212. In an implementation, the one or more control prep container instructions i1212 when executed direct electronically controlling preparation thru control of an outlet of an ingredient container holding an ingredient used for preparation of the ingestible product (e.g. an implementation of the processor component s102 is configured to electronically control an outlet of the material storage component s734 configured as an ingredient container according to an access profile included in the directive information, etc.). Furthermore, the control prep container electrical circuitry arrangement e1212 when activated will perform the operation o1212. In an implementation, the control prep container electrical circuitry arrangement e1212, when activated performs electronically controlling preparation thru control of an outlet of an ingredient container holding an ingredient used for preparation of the ingestible product (e.g. an implementation of the processor component s102 is configured to electronically control an outlet of the material storage component s734 configured as an ingredient container according to an access profile included in the directive information, etc.). In an implementation, the electronically controlling preparation thru control of an outlet of an ingredient container holding an ingredient used for preparation of the ingestible product is carried out by electronically controlling preparation thru control of an outlet of an ingredient container holding an ingredient used for preparation of the ingestible product (e.g. an implementation of the processor component s102 is configured to electronically control an outlet of the material storage component s734 configured as an ingredient container according to an access profile included in the directive information, etc.).

In one or more implementations, operation o12 includes an operation o1213 for electronically controlling preparation thru control of an outlet of an ingredient syringe holding an ingredient used for preparation of the ingestible product. An exemplary version of the non-transitory signal bearing medium n100 is depicted as bearing one or more control prep syringe instructions i1213 that when executed will direct performance of the operation o1213. In an implementation, the one or more control prep syringe instructions i1213 when executed direct electronically controlling preparation thru control of an outlet of an ingredient syringe holding an ingredient used for preparation of the ingestible product (e.g. an implementation of the processor component s102 is configured to electronically control an outlet of the material storage component s734 configured as an ingredient syringe according to an access profile included in the directive information, etc.). Furthermore, the control prep syringe electrical circuitry arrangement e1213 when activated will perform the operation o1213. In an implementation, the control prep syringe electrical circuitry arrangement e1213, when activated performs electronically controlling preparation thru control of an outlet of an ingredient syringe holding an ingredient used for preparation of the ingestible product (e.g. an implementation of the processor component s102 is configured to electronically control an outlet of the material storage component s734 configured as an ingredient syringe according to an access profile included in the directive information, etc.). In an implementation, the electronically controlling preparation thru control of an outlet of an ingredient syringe holding an ingredient used for preparation of the ingestible product is carried out by electronically controlling preparation thru control of an outlet of an ingredient syringe holding an ingredient used for preparation of the ingestible product (e.g. an implementation of the processor component s102 is configured to electronically control an outlet of the material storage component s734 configured as an ingredient syringe according to an access profile included in the directive information, etc.).

In one or more implementations, operation o12 includes an operation o1214 for electronically controlling preparation thru control of mixing of at least some of the ingredients used to prepare the ingestible product before thermal treatment of the ingredients. An exemplary version of the non-transitory signal bearing medium n100 is depicted as bearing one or more control prep mix before thermal instructions i1214 that when executed will direct performance of the operation o1214. In an implementation, the one or more control prep mix before thermal instructions i1214 when executed direct electronically controlling preparation thru control of mixing of at least some of the ingredients used to prepare the ingestible product before thermal treatment of the ingredients (e.g. an implementation of the processor component s102 is configured to electronically control the mixer component s716 according to a mixing profile included in the directive information, etc.). Furthermore, the control prep mix before thermal electrical circuitry arrangement e1214 when activated will perform the operation o1214. In an implementation, the control prep mix before thermal electrical circuitry arrangement e1214, when activated performs electronically controlling preparation thru control of mixing of at least some of the ingredients used to prepare the ingestible product before thermal treatment of the ingredients (e.g. an implementation of the processor component s102 is configured to electronically control the mixer component s716 according to a mixing profile included in the directive information, etc.). In an implementation, the electronically controlling preparation thru control of mixing of at least some of the ingredients used to prepare the ingestible product before thermal treatment of the ingredients is carried out by electronically controlling preparation thru control of mixing of at least some of the ingredients used to prepare the ingestible product before thermal treatment of the ingredients (e.g. an implementation of the processor component s102 is configured to electronically control the mixer component s716 according to a mixing profile included in the directive information, etc.).

In one or more implementations, operation o12 includes an operation o1215 for electronically controlling preparation thru control of blending of at least some of the ingredients used to prepare the ingestible product after thermal treatment of the ingredients. An exemplary version of the non-transitory signal bearing medium n100 is depicted as bearing one or more control prep re mix after thermal instructions i1215 that when executed will direct performance of the operation o1215. In an implementation, the one or more control prep re mix after thermal instructions i1215 when executed direct electronically controlling preparation thru control of blending of at least some of the ingredients used to prepare the ingestible product after thermal treatment of the ingredients (e.g. an implementation of the processor component s102 is configured to electronically control the blending component s714 according to a blending profile involving some of the ingredients used to prepare the ingestible product included in the directive information, etc.). Furthermore, the control prep re mix after thermal electrical circuitry arrangement e1215 when activated will perform the operation o1215. In an implementation, the control prep re mix after thermal electrical circuitry arrangement e1215, when activated performs electronically controlling preparation thru control of blending of at least some of the ingredients used to prepare the ingestible product after thermal treatment of the ingredients (e.g. an implementation of the processor component s102 is configured to electronically control the blending component s714 according to a blending profile involving some of the ingredients used to prepare the ingestible product included in the directive information, etc.). In an implementation, the electronically controlling preparation thru control of blending of at least some of the ingredients used to prepare the ingestible product after thermal treatment of the ingredients is carried out by electronically controlling preparation thru control of blending of at least some of the ingredients used to prepare the ingestible product after thermal treatment of the ingredients (e.g. an implementation of the processor component s102 is configured to electronically control the blending component s714 according to a blending profile involving some of the ingredients used to prepare the ingestible product included in the directive information, etc.).

In one or more implementations, as shown in FIG. 41, operation o12 includes an operation o1216 for electronically controlling preparation thru control of thermal treatment of ingredients used to prepare the ingestible product, the thermal treatment including heating, cooling, or a combination thereof of the ingredients. An exemplary version of the non-transitory signal bearing medium n100 is depicted as bearing one or more control prep heating cooling instructions i1216 that when executed will direct performance of the operation o1216. In an implementation, the one or more control prep heating cooling instructions i1216 when executed direct electronically controlling preparation thru control of thermal treatment of ingredients used to prepare the ingestible product, the thermal treatment including heating, cooling, or a combination thereof of the ingredients (e.g. an implementation of the processor component s102 is configured to electronically control the heating component s702 and/or the cooling component s704 according to a thermal profile included in the directive information, etc.). Furthermore, the control prep heating cooling electrical circuitry arrangement e1216 when activated will perform the operation o1216. In an implementation, the control prep heating cooling electrical circuitry arrangement e1216, when activated performs electronically controlling preparation thru control of thermal treatment of ingredients used to prepare the ingestible product, the thermal treatment including heating, cooling, or a combination thereof of the ingredients (e.g. an implementation of the processor component s102 is configured to electronically control the heating component s702 and/or the cooling component s704 according to a thermal profile included in the directive information, etc.). In an implementation, the electronically controlling preparation thru control of thermal treatment of ingredients used to prepare the ingestible product, the thermal treatment including heating, cooling, or a combination thereof of the ingredients is carried out by electronically controlling preparation thru control of thermal treatment of ingredients used to prepare the ingestible product, the thermal treatment including heating, cooling, or a combination thereof of the ingredients (e.g. an implementation of the processor component s102 is configured to electronically control the heating component s702 and/or the cooling component s704 according to a thermal profile included in the directive information, etc.).

In one or more implementations, operation O12 includes an operation o1217 for electronically controlling preparation thru control of amount of time spent for a particular step in preparation of the ingestible product. An exemplary version of the non-transitory signal bearing medium n100 is depicted as bearing one or more control prep time control instructions i1217 that when executed will direct performance of the operation o1217. In an implementation, the one or more control prep time control instructions i1217 when executed direct electronically controlling preparation thru control of amount of time spent for a particular step in preparation of the ingestible product (e.g. an implementation of the processor component s102 is configured to electronically control components of the material processing subsystem s700 based upon an internal clock of the processor according to a time profile included in the directive information, etc.). Furthermore, the control prep time control electrical circuitry arrangement e1217 when activated will perform the operation o1217. In an implementation, the control prep time control electrical circuitry arrangement e1217, when activated performs electronically controlling preparation thru control of amount of time spent for a particular step in preparation of the ingestible product (e.g. an implementation of the processor component s102 is configured to electronically control components of the material processing subsystem s700 based upon an internal clock of the processor according to a time profile included in the directive information, etc.). In an implementation, the electronically controlling preparation thru control of amount of time spent for a particular step in preparation of the ingestible product is carried out by electronically controlling preparation thru control of amount of time spent for a particular step in preparation of the ingestible product (e.g. an implementation of the processor component s102 is configured to electronically control components of the material processing subsystem s700 based upon an internal clock of the processor according to a time profile included in the directive information, etc.).

In one or more implementations, operation o12 includes an operation o1218 for electronically controlling preparation thru electronically excluding ingredients from being included in the preparation of the ingestible product. An exemplary version of the non-transitory signal bearing medium n100 is depicted as bearing one or more control prep ingredient exclusion instructions i1218 that when executed will direct performance of the operation o1218. In an implementation, the one or more control prep ingredient exclusion instructions i1218 when executed direct electronically controlling preparation thru electronically excluding ingredients from being included in the preparation of the ingestible product (e.g. an implementation of the processor component s102 is configured to electronically control the sorting component s728 to exclude one or more ingredients from being included in the ingestible product according to an exclusion profile included in the directive information, etc.). Furthermore, the control prep ingredient exclusion electrical circuitry arrangement e1218 when activated will perform the operation o1218. In an implementation, the control prep ingredient exclusion electrical circuitry arrangement e1218, when activated performs electronically controlling preparation thru electronically excluding ingredients from being included in the preparation of the ingestible product (e.g. an implementation of the processor component s102 is configured to electronically control the sorting component s728 to exclude one or more ingredients from being included in the ingestible product according to an exclusion profile included in the directive information, etc.). In an implementation, the electronically controlling preparation thru electronically excluding ingredients from being included in the preparation of the ingestible product is carried out by electronically controlling preparation thru electronically excluding ingredients from being included in the preparation of the ingestible product (e.g. an implementation of the processor component s102 is configured to electronically control the sorting component s728 to exclude one or more ingredients from being included in the ingestible product according to an exclusion profile included in the directive information, etc.).

In one or more implementations, operation o12 includes an operation o1219 for electronically controlling preparation thru electronically including ingredients in the preparation of the ingestible product. An exemplary version of the non-transitory signal bearing medium n100 is depicted as bearing one or more control prep ingredient inclusion instructions i1219 that when executed will direct performance of the operation o1219. In an implementation, the one or more control prep ingredient inclusion instructions i1219 when executed direct electronically controlling preparation thru electronically including ingredients in the preparation of the ingestible product (e.g. an implementation of the processor component s102 is configured to electronically control the sorting component s728 to include one or more ingredients in the ingestible product according to an inclusion profile included in the directive information, etc.). Furthermore, the control prep ingredient inclusion electrical circuitry arrangement e1219 when activated will perform the operation o1219. In an implementation, the control prep ingredient inclusion electrical circuitry arrangement e1219, when activated performs electronically controlling preparation thru electronically including ingredients in the preparation of the ingestible product (e.g. an implementation of the processor component s102 is configured to electronically control the sorting component s728 to include one or more ingredients in the ingestible product according to an inclusion profile included in the directive information, etc.). In an implementation, the electronically controlling preparation thru electronically including ingredients in the preparation of the ingestible product is carried out by electronically controlling preparation thru electronically including ingredients in the preparation of the ingestible product (e.g. an implementation of the processor component s102 is configured to electronically control the sorting component s728 to include one or more ingredients in the ingestible product according to an inclusion profile included in the directive information, etc.).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof (the virtually any combination being limited to patentable subject matter under 35 U.S.C. 101). In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof (the virtually any combination being limited to patentable subject matter under 35 U.S.C. 101) can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A method for preparing controlled substance ingestible products upon electronically verifying at least two information aspects stored by mobile device computer audio files, comprising:

providing a vending machine, the vending machine including at least one production machine;
engaging at least one electronic memory of a mobile device associated with a particular individual living being during a swipe of the mobile device within a proximity of the vending machine;
receiving at least one computer audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device;
accessing a database bearing at least one electronic voice print associated with at least one known issuer;
comparing at least a portion of the received at least one audio file with one or more electronic voice prints of the accessed database to verify an identity of the issuer of the controlled substance directive;
confirming that the identified issuer is authorized by a verifying authority to issue the controlled substance directive, including at least receiving verification from the verifying authority via at least one network connection of the vending machine; and
controlling the at least one production machine to at least partially prepare an ingestible product designated to be ingested by the particular individual living being associated with the at least one controlled substance directive at least partially based on the comparing and the confirming.

2. A system for preparing controlled substance ingestible products upon electronically verifying at least two information aspects stored by mobile device computer audio files, comprising:

a vending machine, including at least:
at least one production machine;
means for engaging at least one electronic memory of a mobile device associated with a particular individual living being during a swipe of the mobile device within a proximity of the vending machine;
means for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device;
means for accessing a database bearing at least one electronic voice print associated with at least one known issuer;
means for comparing at least a portion of the received at least one audio file with one or more electronic voice prints of the accessed database to verify an identity of the issuer of the controlled substance directive;
means for confirming that the identified issuer is authorized by a verifying authority to issue the controlled substance directive, including at least receiving verification from the verifying authority via at least one network connection of the vending machine; and
means for controlling the at least one production machine to at least partially prepare an ingestible product designated to be ingested by the particular individual living being associated with the at least one controlled substance directive at least partially based on the comparing and the confirming. from the at least one electronic memory during the swipe of the mobile device.

3. A system for preparing controlled substance ingestible products upon electronically verifying at least two information aspects stored by mobile device audio files, comprising:
a vending machine, including at least:
at least one production machine;
circuitry for engaging at least one electronic memory of a mobile device associated with a particular individual living being during a swipe of the mobile device within a proximity of the vending machine;
circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device;
circuitry for accessing a database bearing at least one electronic voice print associated with at least one known issuer;
circuitry for comparing at least a portion of the received at least one audio file with one or more electronic voice prints of the accessed database to verify an identity of the issuer of the controlled substance directive;
circuitry for confirming that the identified issuer is authorized by a verifying authority to issue the controlled substance directive, including at least circuitry for receiving verification from the verifying authority via at least one network connection of the vending machine; and
circuitry for controlling the at least one production machine to at least partially prepare an ingestible product designated to be ingested by the particular individual living being associated with the at least one controlled substance directive, the circuitry for controlling at least partially based on the circuitry for comparing and the circuitry for confirming.

4. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:
an audio in/out component; and
circuitry for receiving the at least one audio file associated with directive information from the at least one electronic memory during the swipe of the mobile device, the mobile device wirelessly coupled with the audio in/out component during the swipe of the mobile device.

5. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:
circuitry for receiving the at least one audio file associated with the directive information sent by an authority, the at least one audio file including at least some data facilitating determination of (a) verification information operable to allow verification that issuance of the directive information involved an authority and (b) confirmation information operable to allow confirmation that the authority is authorized to issue controlled substance directives.

6. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:
circuitry for receiving at least one audio file associated with directive information sent by an authority, the receiving at least one audio file via a swipe of a mobile device identified with an issuer of the controlled substance directive and provided to the particular individual living being previous to the swipe of the mobile device.

7. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:
circuitry for receiving at least one audio file associated with the directive information sent by the authority; and
circuitry for verifying (a) that the at least one controlled substance directive has been issued by the authority and (b) that the authority is authorized to issue the at least one controlled substance directive at least partially via verifying at least one encryption key associated with the authority.

8. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:
circuitry for reading the at least one audio file associated with the directive information sent by the authority from the at least one electronic memory during the swipe of the mobile device, the at least one audio file recorded by the issuer via at least one recording function of the mobile device previous to the swipe of the mobile device.

9. The system of claim 3, wherein circuitry for comparing at least a portion of the received at least one audio file with one or more electronic voice prints of the accessed database to verify an identity of the issuer of the controlled substance directive comprises:
circuitry for running a comparison analysis of at least a portion of the at least one audio file and one or more electronic voice prints of the accessed database to verify an identity of the issuer of the at least one controlled substance directive.

10. The system of claim 3, wherein circuitry for confirming that the identified issuer is authorized by a verifying authority to issue the controlled substance directive, including at least circuitry for receiving verification from the verifying authority via at least one network connection of the vending machine comprises:
circuitry for accessing, via at least one network connection of the vending machine, a database associated with a verifying authority to confirm that the identified issuer is authorized by the verifying authority to issue the at least one controlled substance directive.

11. The system of claim 3, further comprising:
circuitry for receiving living being identification associated with a particular individual living being designated by the at least one controlled substance directive; and
circuitry for dispensing the ingestible product at least partially based on the circuitry for receiving living being identification.

12. The system of claim 11, wherein circuitry for receiving living being identification associated with a particular individual living being designated by the at least one controlled substance directive comprises:
circuitry for engaging with at least one electronic memory of a mobile device associated with the particular individual living being designated by the at least one controlled substance directive during a swipe of the mobile device within a proximity of the machine; and
circuitry for reading the living being identification from the at least one electronic memory during the swipe of the mobile device.

13. The system of claim 11, wherein circuitry for receiving living being identification associated with a particular individual living being designated by the at least one controlled substance directive comprises:
circuitry for receiving at least one indication of an identity of a user of the vending machine at least partially via reading at least a portion of an electronic identification card proffered by the user of the vending machine.

14. The system of claim 11, wherein circuitry for receiving living being identification associated with a particular individual living being designated by the at least one controlled substance directive comprises:
circuitry for receiving at least one indication of an identity of a user of the vending machine at least partially via reading at least a portion of an electronic memory stripe integrated into a card proffered by the user of the vending machine.

15. The system of claim 11, wherein circuitry for receiving living being identification associated with a particular individual living being designated by the at least one controlled substance directive comprises:
circuitry for receiving at least one indication of an identity of a user of the vending machine at least partially via reading at least a portion of an RFID tag proffered by the user of the vending machine.

16. The system of claim 3, wherein circuitry for engaging at least one electronic memory of a mobile device associated with a particular individual living being during a swipe of the mobile device within a proximity of the vending machine comprises:
circuitry for detecting a swipe of a mobile device within a proximity of the machine by a user of the vending machine;
circuitry for engaging with at least one electronic memory of the mobile device to receive at least one audio file associated with at least one controlled substance directive issued by an issuer, the at least one audio file received from the at least one electronic memory of the mobile device during the swipe of the mobile device;
circuitry for receiving an identity of the user of the vending machine at least partially via reading at least a portion of an electronic memory stripe integrated into a credit card proffered by the user of the vending machine;
circuitry for obtaining an identification of a designated particular individual living being within the at least one controlled substance directive; and
circuitry for dispensing an ingestible product by the vending machine if the identification of the designated particular individual living being matches the received identity of the user of the vending machine.

17. The system of claim 3, wherein circuitry for engaging at least one electronic memory of a mobile device associated with a particular individual living being during a swipe of the mobile device within a proximity of the vending machine comprises:
circuitry for engaging at least one electronic memory of a cell phone associated with a particular individual living being during a cell phone swipe of the cell phone within a proximity of the vending machine.

18. The system of claim 3, wherein circuitry for engaging at least one electronic memory of a mobile device associated with a particular individual living being during a swipe of the mobile device within a proximity of the vending machine comprises:
a weight sensing component of the vending machine; and
circuitry for engaging at least one electronic memory of a cell phone associated with a particular individual living being during a cell phone swipe of the cell phone at least partially based on sensing the particular individual living being upon the weight sensing component of the vending machine.

19. The system of claim 18, further comprising:
circuitry for detecting, using the weight sensing component of the vending machine, a signal associated with the particular individual living being departing the proximity of the vending machine; and
circuitry for signaling to prevent at least one of preparation or dispensing of the ingestible product at least partially based on the signal associated with the particular individual living being departing the proximity of the vending machine.

20. The system of claim 3, wherein circuitry for controlling the at least one production machine to at least partially prepare an ingestible product designated to be ingested by the particular individual living being associated with the at least one controlled substance directive, the circuitry for controlling at least partially based on the circuitry for comparing and the circuitry for confirming comprises:
at least one internal clock of the vending machine; and circuitry for controlling at least partial preparation of the ingestible product in accordance with a time profile of the at least one controlled substance directive, including at least controlling the preparation at one or more times associated with the time profile.

21. The system of claim 3, further comprising:

circuitry for receiving at least one indication of an identity of a user of the vending machine via engaging with an electronic memory stripe integrated into a credit card during a credit card swipe by the user of the vending machine.

22. The system of claim 3, further comprising:

circuitry for receiving at least one indication of an identity of a user of the vending machine via reading a bar code proffered by the user of the vending machine.

23. The system of claim 3, wherein circuitry for engaging at least one electronic memory of a mobile device associated with a particular individual living being during a swipe of the mobile device within a proximity of the vending machine comprises:

circuitry for engaging at least one memory card of a mobile device during a swipe of the mobile device within a proximity of the vending machine to obtain a computer audio file stored by the memory card.

24. The system of claim 3, wherein circuitry for engaging at least one electronic memory of a mobile device associated with a particular individual living being during a swipe of the mobile device within a proximity of the vending machine comprises:

circuitry for engaging at least one electronic memory of a mobile device during a swipe of the mobile device within a proximity of the vending machine to wirelessly obtain a computer audio file stored by the electronic memory.

25. The system of claim 3, wherein circuitry for engaging at least one electronic memory of a mobile device associated with a particular individual living being during a swipe of the mobile device within a proximity of the vending machine comprises:

circuitry for engaging at least one electronic memory of a mobile device associated with a particular individual living being during a swipe of the mobile device within a proximity of the vending machine, the proximity of the vending machine including at least a network proximity.

26. The system of claim 3, wherein circuitry for engaging at least one electronic memory of a mobile device associated with a particular individual living being during a swipe of the mobile device within a proximity of the vending machine comprises:

circuitry for engaging at least one electronic memory of a mobile device associated with a particular individual living being during a swipe of the mobile device within a proximity of the vending machine, the proximity of the vending machine including at least within an international region of the vending machine.

27. The system of claim 3, wherein circuitry for controlling the at least one production machine to at least partially prepare an ingestible product designated to be ingested by the particular individual living being associated with the at least one controlled substance directive, the circuitry for controlling at least partially based on the circuitry for comparing and the circuitry for confirming comprises:

circuitry for receiving control signals from a foreign country to control the at least one production machine to at least partially prepare the ingestible product.

28. The system of claim 3, wherein circuitry for controlling the at least one production machine to at least partially prepare an ingestible product designated to be ingested by the particular individual living being associated with the at least one controlled substance directive, the circuitry for controlling at least partially based on the circuitry for comparing and the circuitry for confirming comprises:

circuitry for receiving control signals from a distal location to control the at least one production machine to at least partially prepare the ingestible product.

29. The system of claim 3, wherein circuitry for controlling the at least one production machine to at least partially prepare an ingestible product designated to be ingested by the particular individual living being associated with the at least one controlled substance directive, the circuitry for controlling at least partially based on the circuitry for comparing and the circuitry for confirming comprises:

circuitry for providing control signals from a local location to control the at least one production machine to at least partially prepare the ingestible product.

30. The system of claim 3, wherein circuitry for confirming that the identified issuer is authorized by a verifying authority to issue the controlled substance directive, including at least circuitry for receiving verification from the verifying authority via at least one network connection of the vending machine comprises:

circuitry for confirming that the identified issuer is authorized by at least one license governing authority to issue the controlled substance directive.

31. The system of claim 30, wherein circuitry for confirming that the identified issuer is authorized by at least one license governing authority to issue the controlled substance directive comprises:

circuitry for confirming that the identified issuer is authorized by at least one of a state medical board, a state osteopathic board, a state medical licensing authority, a state pharmacy board, a state dental board, or a state veterinary board to issue the controlled substance directive.

32. The system of claim 3, wherein circuitry for accessing a database bearing at least one electronic voice print associated with at least one known issuer comprises:

circuitry for accessing a database stored distally to the vending machine via the at least one network connection of the vending machine, the database bearing at least one electronic voice print associated with at least one known issuer.

33. The system of claim 3, wherein circuitry for accessing a database bearing at least one electronic voice print associated with at least one known issuer comprises:

circuitry for accessing a database stored locally to the vending machine, the database bearing at least one electronic voice print associated with at least one known issuer.

34. The system of claim 3, wherein circuitry for comparing at least a portion of the received at least one audio file with one or more electronic voice prints of the accessed database to verify an identity of the issuer of the controlled substance directive comprises:

circuitry for transmitting a request via the at least one network connection of the vending machine for a comparison result of comparing the at least a portion of the received at least one audio file with the one or more electronic voice prints of the accessed database.

35. The system of claim 3, wherein circuitry for comparing at least a portion of the received at least one audio file with one or more electronic voice prints of the accessed database to verify an identity of the issuer of the controlled substance directive comprises:

circuitry for transmitting the at least a portion of the received at least one audio file via the at least one network connection of the vending machine; and circuitry for receiving an apparent identity of the issuer of the controlled substance directive at least partially determined using the at least a portion of the received at least one audio file, the receiving via the at least one network connection of the vending machine.

36. The system of claim 3, wherein circuitry for comparing at least a portion of the received at least one audio file with one or more electronic voice prints of the accessed database to verify an identity of the issuer of the controlled substance directive comprises:

circuitry for utilizing a voice recognition module accessible to the vending machine to obtain a comparison result of the comparing at least a portion of the received at least one audio file with the one or more electronic voice prints of the accessed database.

37. The system of claim 3, wherein the at least one production machine comprises:

at least one automated or semi-automated machine configured to at least one of make, manufacture, fabricate, or otherwise prepare one or more ingestible products to be ingested by one or more living beings.

38. The system of claim 3, wherein the at least one production machine comprises:

at least one machine configured for at least one of energy addition, energy extraction, deposition, or combination in association with one or more ingredients to prepare one or more ingestible products.

39. The system of claim 3, wherein the at least one production machine comprises:

at least one machine configured for at least one of energy addition, energy extraction, deposition, or combination in association with one or more ingredients to prepare one or more ingestible products, the at least one machine internal to the vending machine.

40. The system of claim 3, wherein the at least one production machine comprises:

at least one machine configured for at least one of energy addition, energy extraction, deposition, or combination in association with one or more ingredients to prepare one or more ingestible products, the at least one machine operably coupleable with the vending machine.

41. The system of claim 3, wherein the at least one production machine comprises:

at least one machine configured for at least one of energy addition, energy extraction, deposition, or combination in association with one or more ingredients to prepare one or more ingestible products, the at least one machine networkably coupleable with the vending machine.

42. The system of claim 3, wherein the at least one production machine comprises:

at least one machine configured for at least one of energy addition, energy extraction, deposition, or combination in association with one or more ingredients to prepare one or more ingestible products, the at least one machine wirelessly networkably coupleable with the vending machine.

43. The system of claim 3, wherein circuitry for comparing at least a portion of the received at least one audio file with one or more electronic voice prints of the accessed database to verify an identity of the issuer of the controlled substance directive comprises:

circuitry for comparing at least a portion of the received at least one audio file with one or more electronic voice prints of the accessed database for verification, including at least one of authorship or distribution control, associated with issuance of the controlled substance directive.

44. The system of claim 3, wherein circuitry for engaging at least one electronic memory of a mobile device associated with a particular individual living being during a swipe of the mobile device within a proximity of the vending machine comprises:

circuitry for engaging at least one electronic memory of a mobile device associated with a particular individual living being during a swipe of the mobile device within a proximity of the vending machine, the mobile device including at least a mobile device capable of storing one or more audio recordings via at least one electronic memory.

45. The system of claim 44, wherein circuitry for engaging at least one electronic memory of a mobile device associated with a particular individual living being during a swipe of the mobile device within a proximity of the vending machine, the mobile device including at least a mobile device capable of storing one or more audio recordings via at least one electronic memory comprises:

circuitry for engaging at least one electronic memory of a mobile device associated with a particular individual living being during a swipe of the mobile device within a proximity of the vending machine, the mobile device including at least a digital voice recorder.

46. The system of claim 3, wherein circuitry for engaging at least one electronic memory of a mobile device associated with a particular individual living being during a swipe of the mobile device within a proximity of the vending machine comprises:

circuitry for engaging at least one electronic memory of a mobile device associated with a particular individual living being during a swipe of the mobile device within a proximity of the vending machine, the mobile device including at least one of a cell phone, a smartphone, a tablet, a portable information storage device, or a portable computing device.

47. The system of claim 3, wherein circuitry for engaging at least one electronic memory of a mobile device associated with a particular individual living being during a swipe of the mobile device within a proximity of the vending machine comprises:

circuitry for engaging, using at least one RFID reader of the vending machine, at least one RFID portion of a mobile device associated with a particular individual living being during a swipe of the mobile device within a proximity of the vending machine.

48. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:

circuitry for receiving at least one prescription serial number to obtain at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device.

49. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:
   circuitry for receiving at least one audio file associated with directive information sent by an authority, the directive information including at least one prescription serial number indicative of (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device.

50. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:
   circuitry for receiving at least one audio file received in real-time and associated with directive information provided by the authority in conjunction with an electronic connection of the mobile device with the vending machine.

51. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:
   circuitry for receiving at least one audio file, the at least one audio file including at least one recording of directive information recorded by the authority, the at least one recording received by the mobile device previous to the mobile device swipe.

52. The system of claim 3, wherein circuitry for engaging at least one electronic memory of a mobile device associated with a particular individual living being during a swipe of the mobile device within a proximity of the vending machine comprises:
   circuitry for engaging at least one electronic memory of a mobile device swiped by the particular individual living being, the particular individual living being within a proximity of the vending machine, the mobile device at least one of owned by or provided to the particular individual living being.

53. The system of claim 3, wherein circuitry for receiving living being identification associated with a particular individual living being designated by the at least one controlled substance directive comprises:
   circuitry for receiving at least one indication of an identity of a user of the vending machine at least partially via engaging with an iris scanner to scan an iris of the user of the vending machine.

54. The system of claim 3, wherein circuitry for receiving living being identification associated with a particular individual living being designated by the at least one controlled substance directive comprises:
   circuitry for receiving at least one indication of an identity of a user of the vending machine at least partially via identifying the user of the vending machine via an electronic voice print.

55. The system of claim 3, wherein circuitry for receiving at least one audio file associated with directive information sent by an authority, the directive information including at least (i) living being identification associated with the particular individual living being and (ii) at least one controlled substance directive related to at least one controlled substance designated to be ingested by the particular individual living being, the at least one audio file associated with directive information received from the at least one electronic memory during the swipe of the mobile device comprises:
   circuitry for receiving the directive information including at least directions for at least partial preparation of at least a portion of at least one ingestible product to incorporate the at least one controlled substance therein during the at least partial preparation thereof.

* * * * *